(12) United States Patent
Oda et al.

(10) Patent No.: US 11,844,750 B2
(45) Date of Patent: Dec. 19, 2023

(54) SYRINGE PUMPS FOR AUTOMATIC DRUG COMPOUNDERS

(71) Applicant: CareFusion 303, Inc., San Diego, CA (US)

(72) Inventors: Todd Oda, Torrance, CA (US); Dereck S. Ferdaws, San Diego, CA (US); Tomas Frausto, Walnut, CA (US)

(73) Assignee: CAREFUSION 303, INC., San Diego, CA (US)

( * ) Notice: Subject to any disclaimer, the term of this patent is extended or adjusted under 35 U.S.C. 154(b) by 0 days.

(21) Appl. No.: 18/083,258

(22) Filed: Dec. 16, 2022

(65) Prior Publication Data

US 2023/0121893 A1    Apr. 20, 2023

Related U.S. Application Data

(63) Continuation of application No. 16/497,192, filed as application No. PCT/US2018/024122 on Mar. 23, 2018, now Pat. No. 11,559,468.

(Continued)

(51) Int. Cl.
*A61J 3/00* (2006.01)
*A61M 5/315* (2006.01)
*A61M 39/22* (2006.01)
*A61J 1/20* (2006.01)
*A61M 5/31* (2006.01)
(Continued)

(52) U.S. Cl.
CPC ............... *A61J 3/002* (2013.01); *A61J 1/201* (2015.05); *A61J 1/2096* (2013.01); *A61M 5/31576* (2013.01); *A61M 39/22* (2013.01); *A61J 1/10* (2013.01); *A61M 2005/3114* (2013.01); *A61M 2039/229* (2013.01); *B65B 3/003* (2013.01); *B65B 57/12* (2013.01); *B65B 57/145* (2013.01)

(58) Field of Classification Search
CPC . A61J 1/201; A61J 1/2096; A61J 1/10; B65B 3/003; A61M 5/31576; A61M 39/22; A61M 2005/3114; A61M 2039/229
See application file for complete search history.

(56) References Cited

U.S. PATENT DOCUMENTS

| 5,062,774 A | 11/1991 | Kramer et al. |
| 6,508,791 B1 | 1/2003 | Guerrero |

(Continued)

FOREIGN PATENT DOCUMENTS

| CN | 1077112 A | 10/1993 |
| CN | 1250366 A | 4/2000 |

(Continued)

OTHER PUBLICATIONS

Japanese Office Action for Application No. 2019-552153, dated Mar. 29, 2023, 5 pages including translation.

(Continued)

*Primary Examiner* — Timothy P. Kelly
(74) *Attorney, Agent, or Firm* — Morgan, Lewis & Bockius LLP

(57) ABSTRACT

Various aspects of the subject disclosure relate to a compounder system having a cartridge that includes controllable fluid pathways. The cartridge may include a syringe pump for moving fluid and/or gas, and one or more syringe valves or rotary valves for controlling which of the controllable fluid pathways is open for flow of the fluid and/or gas.

7 Claims, 48 Drawing Sheets

Related U.S. Application Data

(60) Provisional application No. 62/476,683, filed on Mar. 24, 2017.

(51) Int. Cl.

| | | |
|---|---|---|
| *A61J 1/10* | (2006.01) | |
| *B65B 3/00* | (2006.01) | |
| *B65B 57/12* | (2006.01) | |
| *B65B 57/14* | (2006.01) | |

(56) References Cited

U.S. PATENT DOCUMENTS

| | | | |
|---|---|---|---|
| 8,523,816 B2 | 9/2013 | Kirkpatrick | |
| 11,559,468 B2 * | 1/2023 | Oda | A61M 5/31576 |
| 2008/0110458 A1 | 5/2008 | Srinivasan | |
| 2012/0053521 A1 | 3/2012 | Kirkpatrick | |
| 2014/0228762 A1 * | 8/2014 | Capone | A61M 5/16881 604/152 |
| 2014/0343492 A1 | 11/2014 | Kamen | |
| 2015/0087868 A1 | 3/2015 | Lee et al. | |
| 2015/0374585 A1 | 12/2015 | Mansour et al. | |
| 2021/0121363 A1 | 4/2021 | Oda et al. | |

FOREIGN PATENT DOCUMENTS

| | | |
|---|---|---|
| CN | 1338972 A | 3/2002 |
| CN | 1756523 A | 4/2006 |
| CN | 204840286 U | 12/2015 |
| EP | 2446875 A | 5/2012 |
| JP | S4913705 A | 2/1974 |
| JP | H03124976 A | 5/1991 |
| JP | 2013144114 A | 7/2013 |
| WO | WO-2013049783 A1 | 4/2013 |
| WO | WO-2016112163 A1 | 7/2016 |

OTHER PUBLICATIONS

Chinese Office Action for Application No. 201880033640.9, dated Apr. 19, 2021, 14 pages including translation.

International Search Report and Written Opinion for Application No. PCT/US2018/024119, dated Sep. 5, 2018, 15 pages.

Extended European Search Report for Application No. 21191031.0, dated Nov. 16, 2021, 8 pages.

Japanese Office Action for Application No. 2019-552153, dated Jan. 18, 2022, 7 pages including translation.

Japanese Office Action for Application No. 2019-552153, dated Sep. 13, 2022, 6 pages including translation.

Israeli Office Action for Application No. 269452, dated Nov. 24, 2022, 3 pages.

Israeli Office Action for Application No. 269473, dated Nov. 24, 2022, 4 pages.

Japanese Office Action for Application No. 2022-159188, dated Jul. 12, 2023, 4 pages including translation.

* cited by examiner

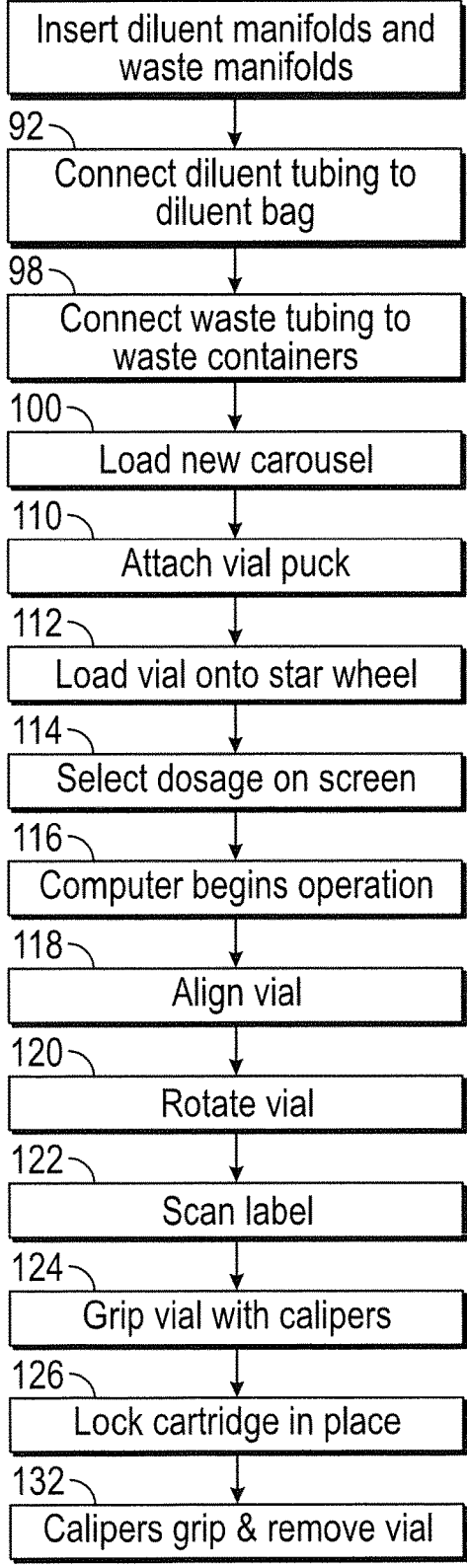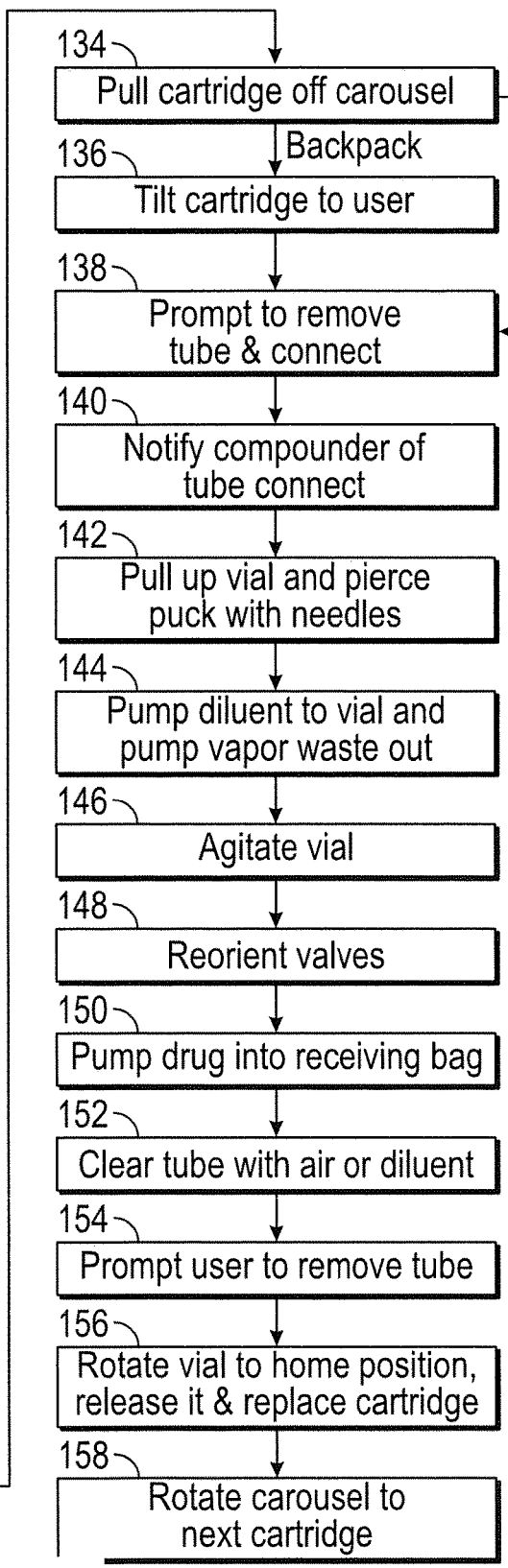
FIG. 8

| Operation | Valve 1 Diluent | | | Valve 2 RC | | |
|---|---|---|---|---|---|---|
| | P1 | P2 | P3 | P1 | P2 | P3 |
| Diluent to Receiving Container | Closed | Open | Closed | Closed | Closed | Open |
| Diluent to Vial | Closed | Open | Closed | Open | Closed | Closed |
| Vial to Receiving Container | Closed | Closed | Open | Closed | Closed | Open |
| Pull Air Back from Receiving Container | Open | Closed | Closed | Closed | Open | Closed |

FIG. 28

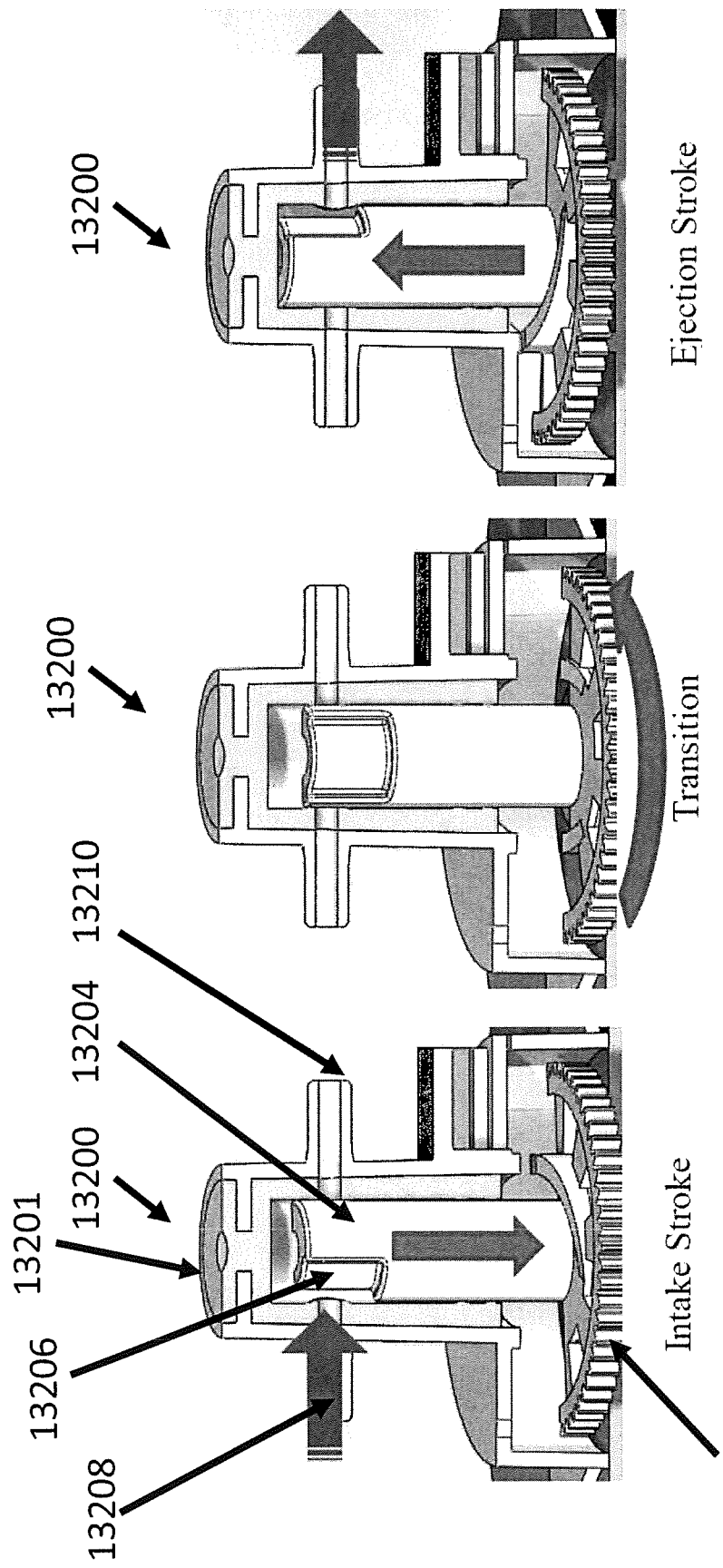

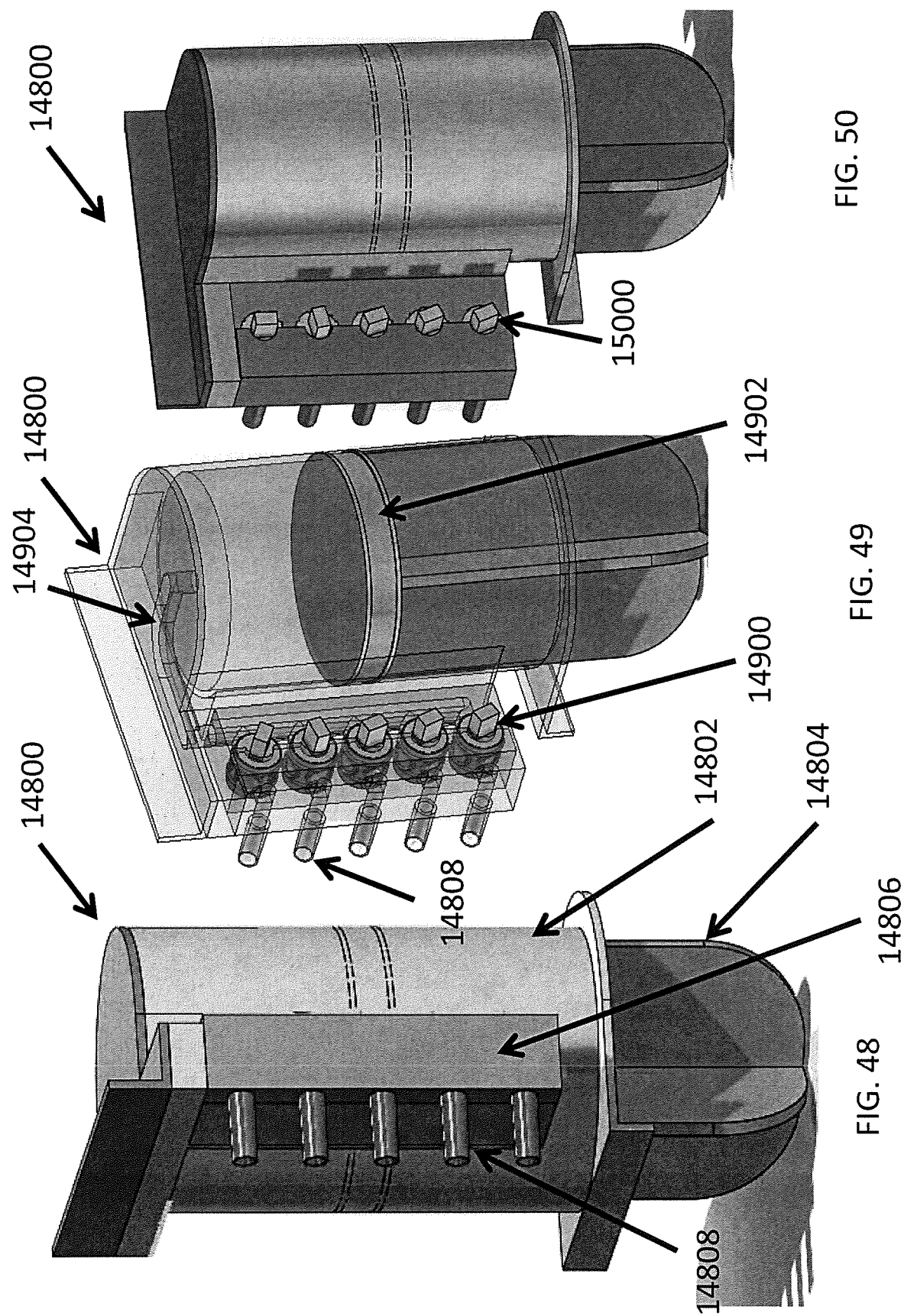

SYRINGE PUMPS FOR AUTOMATIC DRUG COMPOUNDERS

CROSS-REFERENCE TO RELATED APPLICATIONS

The present application is a continuation of U.S. patent application Ser. No. 16/497,192 entitled "SYRINGE PUMP FOR AUTOMATIC DRUG COMPOUNDERS," filed on Sep. 24, 2019, issued as U.S. Pat. No. 11,559,468 on Jan. 24, 2023, which is a 371 of PCT Application No. PCT/US2018/024122 entitled "SYRINGE PUMPS FOR AUTOMATIC DRUG COMPOUNDERS," filed on Mar. 23, 2018, which claims priority to U.S. Provisional Patent Application Ser. No. 62/476,683 entitled "Automatic Drug Compounder," filed on Mar. 24, 2017, the disclosure of each which is hereby incorporated by reference in its entirety for all purposes.

TECHNICAL FIELD

The present disclosure generally relates to an apparatus that reconstitutes, mixes, and delivers a drug from a vial to a receiving container. Specifically, the present disclosure relates to pumping and valving features of a closed system automatic drug compounder.

BACKGROUND

Pharmaceutical compounding is the practice of creating a specific pharmaceutical product to fit the unique need of a patient. In practice, compounding is typically performed by a pharmacist, tech or a nurse who combines the appropriate ingredients using various tools. One common form of compounding comprises the combination of a powdered drug formulation with a specific diluent to create a suspended pharmaceutical composition. These types of compositions are commonly used in intravenous/parenteral medications. It is vital that the pharmaceuticals and diluents are maintained in a sterile state during the compounding process, and there exists a need for automating the process while maintaining the proper mixing characteristics (i.e., certain pharmaceuticals must be agitated in specific ways so that the pharmaceutical is properly mixed into solution but the solution is not frothed and air bubbles are not created). There exists a need for a compounding system that is easy to use, may be used frequently, efficiently, is reliable, and reduces user error.

SUMMARY

A compounder system may pump diluent from a diluent container to a vial containing a drug, and then pump the reconstituted drug to a receiving container. In order to ensure each medication is correctly and safely reconstituted and moved to the receiving container without mixing of medications or leakage, a disposable cartridge is provided that couples the diluent container and the receiving container to the vial and includes fluid pathways controllable by valves of the cartridge for pumping fluids to and from the vial and the container.

Pump components of the cartridge are actuable to move fluid and control fluid motion through the controllable fluid pathways. The pump components may include a syringe pump and rotary valve assembly or a syringe pump and syringe valve assembly, in some examples.

In accordance with various aspects of the disclosure, a compounder system is provided that includes a cartridge having a plurality of controllable fluid pathways fluidly coupled to at least one diluent port, a waste port, and a receiving container port, and a syringe pump/syringe valve apparatus having a plurality of syringes operable to control movement of one or more fluids through the plurality of controllable fluid pathways.

In accordance with other aspects of the disclosure, a compounder system is provided that includes a cartridge having a plurality of controllable fluid pathways fluidly coupled to at least one diluent port, a waste port, and a receiving container port, and a syringe pump/rotary valve apparatus having a syringe and a plurality of rotary valves operable to control movement of one or more fluids through the plurality of controllable fluid pathways.

In accordance with other aspects of the disclosure, a compounder system is provided that includes a cartridge having a plurality of controllable fluid pathways, a syringe pump, and a plurality of valves operable to selectively couple the syringe pump to one or more of the plurality of controllable fluid pathways.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings:

FIG. 8 is a flow chart illustrating an exemplary embodiment of the steps of a process in accordance with aspects of the present disclosure.

FIG. 28 is a chart showing the positioning of certain valves in accordance with aspects of the present disclosure.

FIG. 32 illustrates a partial cross-sectional view of a rotary piston pump/valve in accordance with aspects of the present disclosure.

FIG. 33 illustrates a partial cross-sectional view of the rotary piston pump/valve of FIG. 32 during a transition between an intake stroke and an ejection stroke in accordance with aspects of the present disclosure.

FIG. 34 illustrates a partial cross-sectional view of the rotary piston pump/valve of FIG. 32 during an ejection stroke in accordance with aspects of the present disclosure.

FIG. 48 illustrates a perspective view of a syringe pump/rotary valve apparatus in accordance with aspects of the present disclosure.

FIG. 49 illustrates another perspective view of a syringe pump/rotary valve apparatus in accordance with aspects of the present disclosure.

FIG. 50 illustrates another perspective view of a syringe pump/rotary valve apparatus in accordance with aspects of the present disclosure.

DETAILED DESCRIPTION

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions may be provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

The present system comprises multiple features and technologies that in conjunction form a compounding system that can efficiently reconstitute pharmaceuticals in a sterile environment and deliver the compounded pharmaceutical to a delivery bag for use on a patient.

Figure 1:
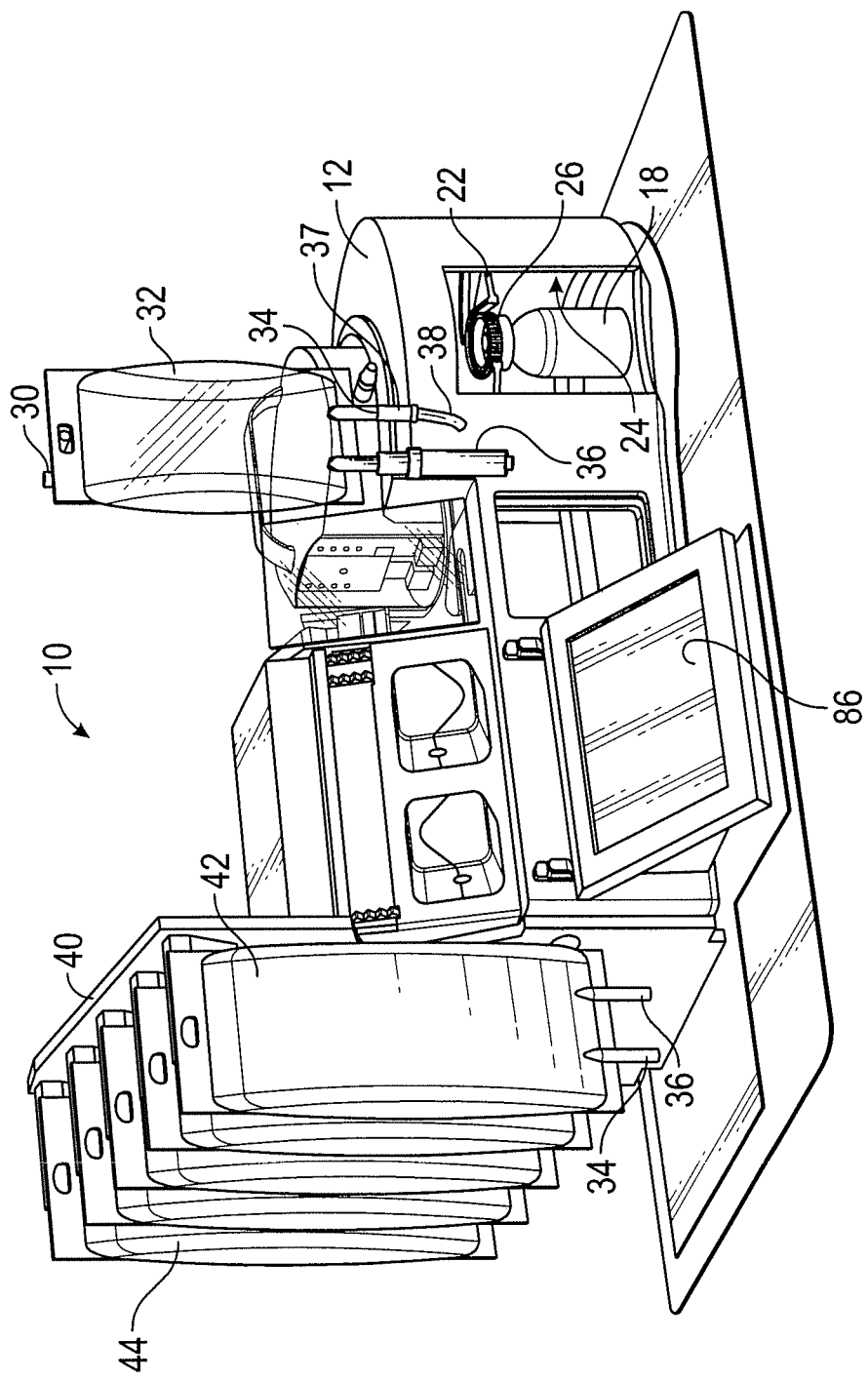
FIG. 1 illustrates a front perspective view of an example of an exemplary embodiment of a compounding system in accordance with aspects of the present disclosure.
Figure 2:
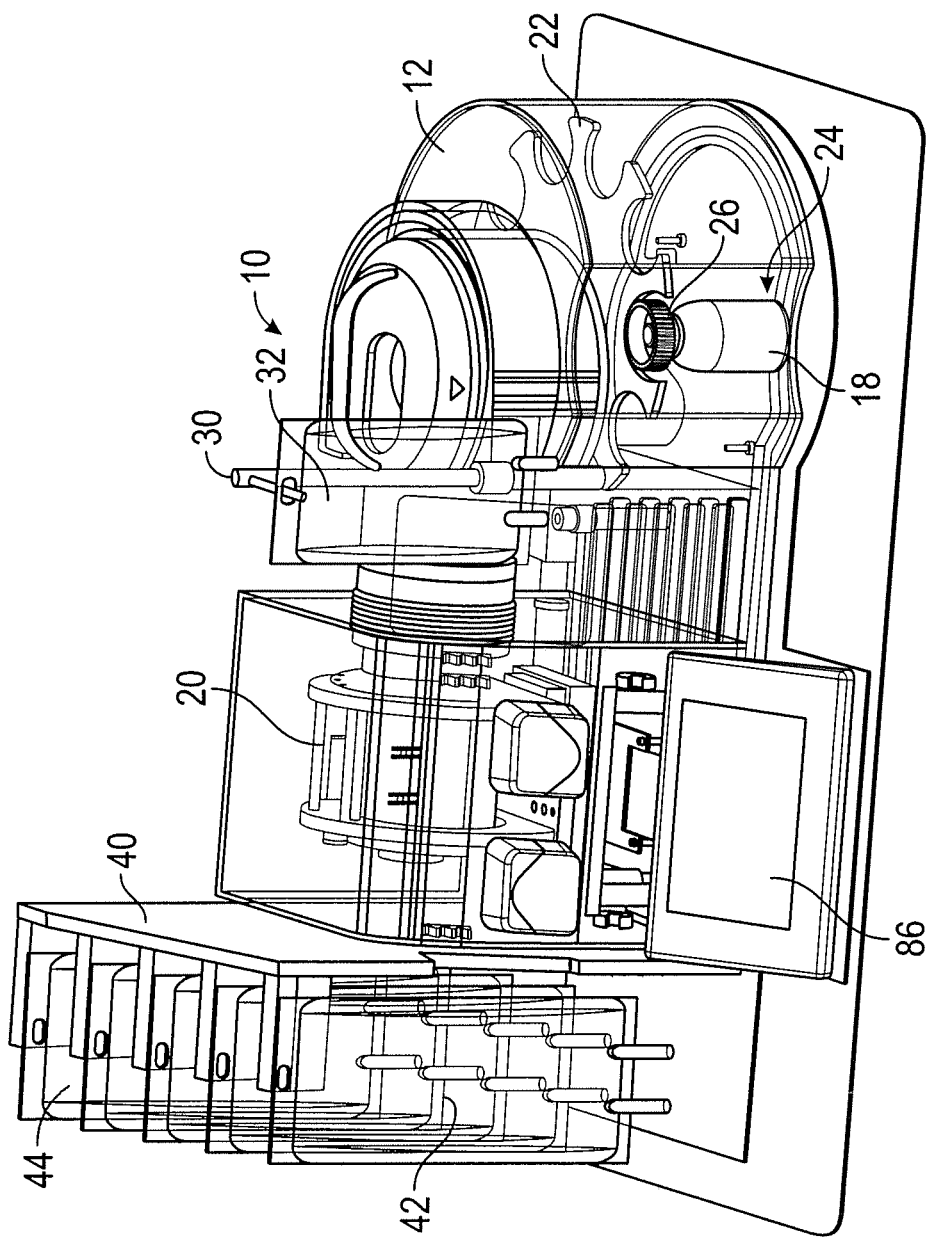
FIG. 2 illustrates a front perspective view of the compounding system of FIG. 1 with a transparent housing in accordance with aspects of the present disclosure.
Figure 3:
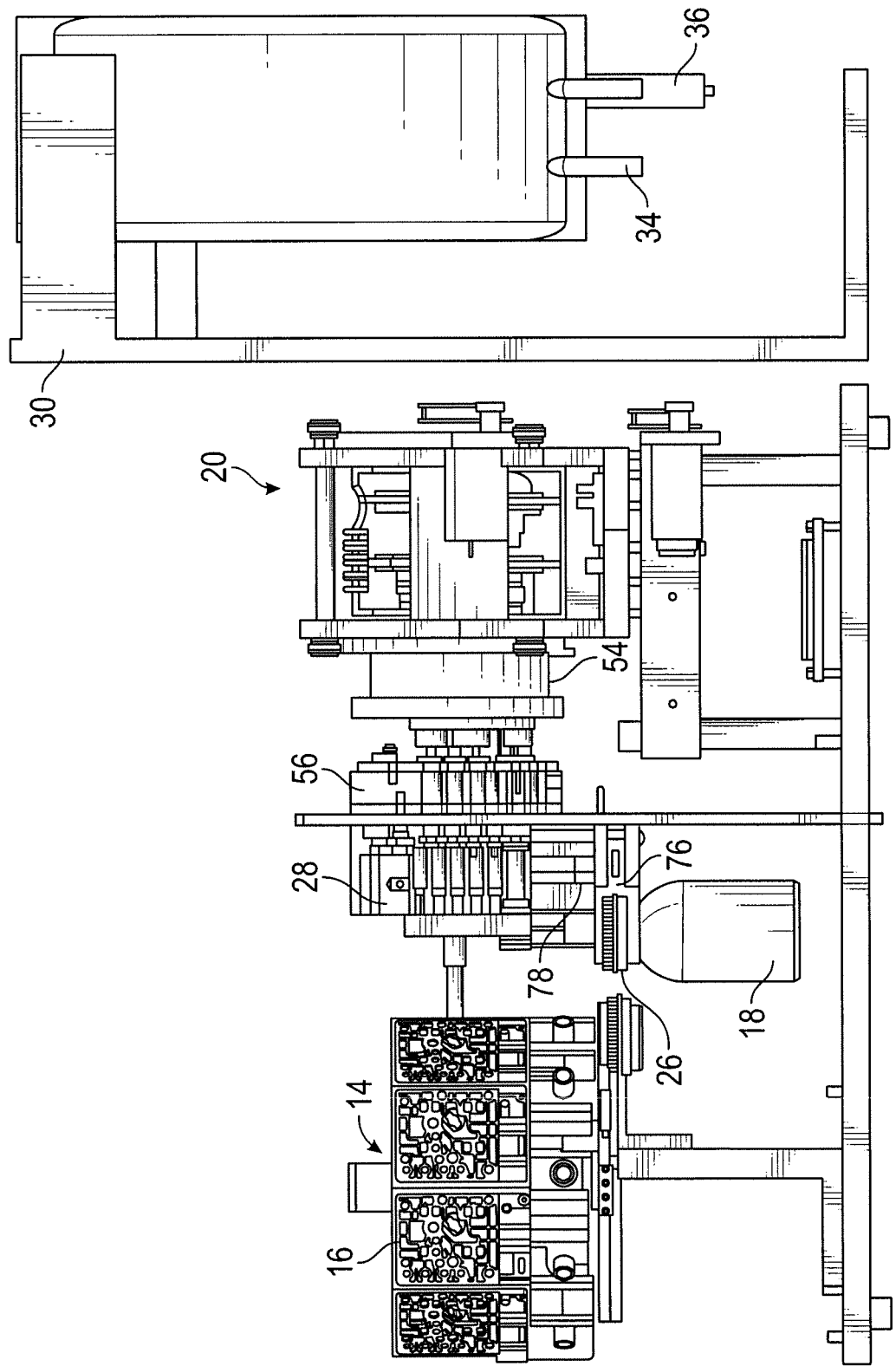
FIG. 3 illustrates a side view of the compounding system of FIG. 1 with the housing removed in accordance with aspects of the present disclosure.

FIG. 1 illustrates a compounder system 10 according to an embodiment. FIG. 2 illustrates the system 10 with a transparent outer housing 12 and FIG. 3 illustrates the system with the housing removed. The system comprises a carousel assembly 14 that contains up to 10 individual cartridges 16. The carousel 14 can hold more or less cartridges 16 if desired. The cartridges 16 are disposable and provide unique fluid paths between a vial 18 containing a powdered drug (or concentrated liquid drug), multiple diluents, and a receiving container. The cartridges 16 may, if desired, also provide a fluid path to a vapor waste container. However, in other embodiments, filtered or unfiltered non-toxic waste may be vented from the compounder to the environment reducing or eliminating the need for a waste port. Each cartridge contains a piston pump and valves that control the fluid intake, outtake, and fluid path selection during the steps of the compounding process as the fluid moves through the cartridge and into a receiving container.

The carousel assembly 14 is mounted on the apparatus such that it can rotate to bring different cartridges 16 into alignment with the pump drive mechanism 20. The carousel 14 is typically enclosed within a housing 12 that can be opened in order to replace the carousel 14 with a new carousel 14 after removing a used one. As illustrated, the carousel 14 can contain up to 10 cartridges 16, allowing a particular carousel to be used up to 10 times. In this configuration, each carousel assembly can support, for example, 10 to 100 receiving containers, depending on the type of compounding to be performed. For example, for hazardous drug compounding, a carousel assembly can support compounding to ten receiving containers. In another example, for non-hazardous drug compounding such as antibiotic or pain medication compounding, a carousel assembly can support compounding to 100 receiving containers. The housing 12 also includes a star wheel 22 positioned underneath the carousel 14. The star wheel 22 rotates vials 18 of pharmaceuticals into position either in concert with, or separate from, the specific cartridges 16 on the carousel 14. The housing 12 may also include an opening 24 for loading the vials 18 into position on the star wheel 22.

Each one of the cartridges 16 in the carousel 14 is a disposable unit that includes multiple pathways for the diluent and vapor waste. These pathways will be described in detail with reference to, for example, FIG. 39 et seq. Each cartridge 16 is a small, single disposable unit that may also include a "backpack" in which a tube for connection to the receiving container (e.g., an IV bag, a syringe, or an elastomeric bag) may be maintained. Each cartridge 16 also may include a pumping mechanism such as a piston pump for moving fluid and vapor through the cartridge 16 as well as a dual lumen needle in a housing that can pierce a vial puck 26 on top of a vial 18 once the vial 18 has been moved into position by the pump drive mechanism 20. For example, the needle may pierce the vial puck 26 via the compressive action of the vial puck 26, which is moved towards the needle. Each cartridge 16 also includes a plurality of ports designed to match up with the needles of a plurality of diluent manifolds. Each cartridge 16 also includes openings to receive mounting posts and a locking bayonet from the pump head assembly 28. Although a locking bayonet is described herein as an example, other locking mechanisms may be used to retrieve and lock a cartridge to the pump head (e.g., grippers, clamps, or the like may extend from the pump head). Each cartridge 16 also includes openings allowing valve actuators from the pump motor mechanism to interact with the valves on each cartridge 16.

Adjacent the housing 12 that holds the vials 18 and the carousel 14 is an apparatus 30 for holding at least one container 32, such as an IV bag 32 as shown in the figures. The IV bag 32 typically has two ports such as ports 34 and 36. For example, in one implementation, port 34 is an intake port 34 and port 36 is an outlet port 36. Although this implementation is sometimes discussed herein as an example, either of ports 34 and 36 may be implemented as an input and/or outlet port for container 32. For example, in another implementation, an inlet 34 for receiving a connector at the end of tubing 38 may be provided on the outlet port 36. In the embodiment shown, the IV bag 32 hangs from the holding apparatus 30, which, in one embodiment is a post with a hook as illustrated in FIGS. 1-3. As discussed in further detail hereinafter, one or more of the hooks for hanging containers such as diluent containers, receiving containers, or waste containers may be provided with a weight sensor such as a load cell that detects and monitors the weight of a hung container. The holding apparatus 30 can take any other form necessary to position the IV bag 32 or other pharmaceutical container. Once the IV bag 32 is positioned on the holding apparatus 30, a first tube 38 (a portion of which is shown in FIG. 1) is connected from a cartridge 16 on the carousel 14 to the inlet 34 of the IV bag 32. For example, the first tube may be housed in a backpack attached to the cartridge and extended from within the backpack (e.g., by an operator or automatically) to reach the IV bag 32. A connector 37 such as a Texium® connector may be provided on the end of tube 38 for connecting to inlet 34 of receiving container 32.

On the opposite side of the compounder 10 is an array of holding apparatuses 40 for holding multiple IV bags 32 or other containers. In the illustrated version of the compounder 10, five IV bags 42, 44 are pictured. Three of these bags 42 may contain diluents, such as saline, D5W or sterile water, although any diluent known in the art may be utilized. An additional bag in the array may be an empty vapor waste bag 44 for collecting waste such as potentially hazardous or toxic vapor waste from the mixing process. An additional bag 44 may be a liquid waste bag. The liquid waste bag may be configured to receive non-toxic liquid waste such as saline from a receiving container. As discussed in further detail hereinafter, liquid waste may be pumped to the waste bag via dedicated tubing using a mechanical pump. In operation, diluent lines and a vapor waste line from the corresponding containers 42 and 44 may each be connected to a cartridge 16 through a disposable manifold.

The compounding system 10 also includes a specialized vial puck 26 designed to attach to multiple types of vials 18. In operation, the vial puck 26 is placed on top of the vial 18 containing the drug in need of reconstitution. Once the vial puck 26 is in place, the vial 18 is loaded into the star wheel 22 of the compounder 10. Mating features on the vial puck 26 provide proper alignment both while the vial puck 26 is in the star wheel 22 and when the vial puck 26 is later rotated into position so that the compounder 10 can remove it from the star wheel 22 for further processing.

Figure 4:
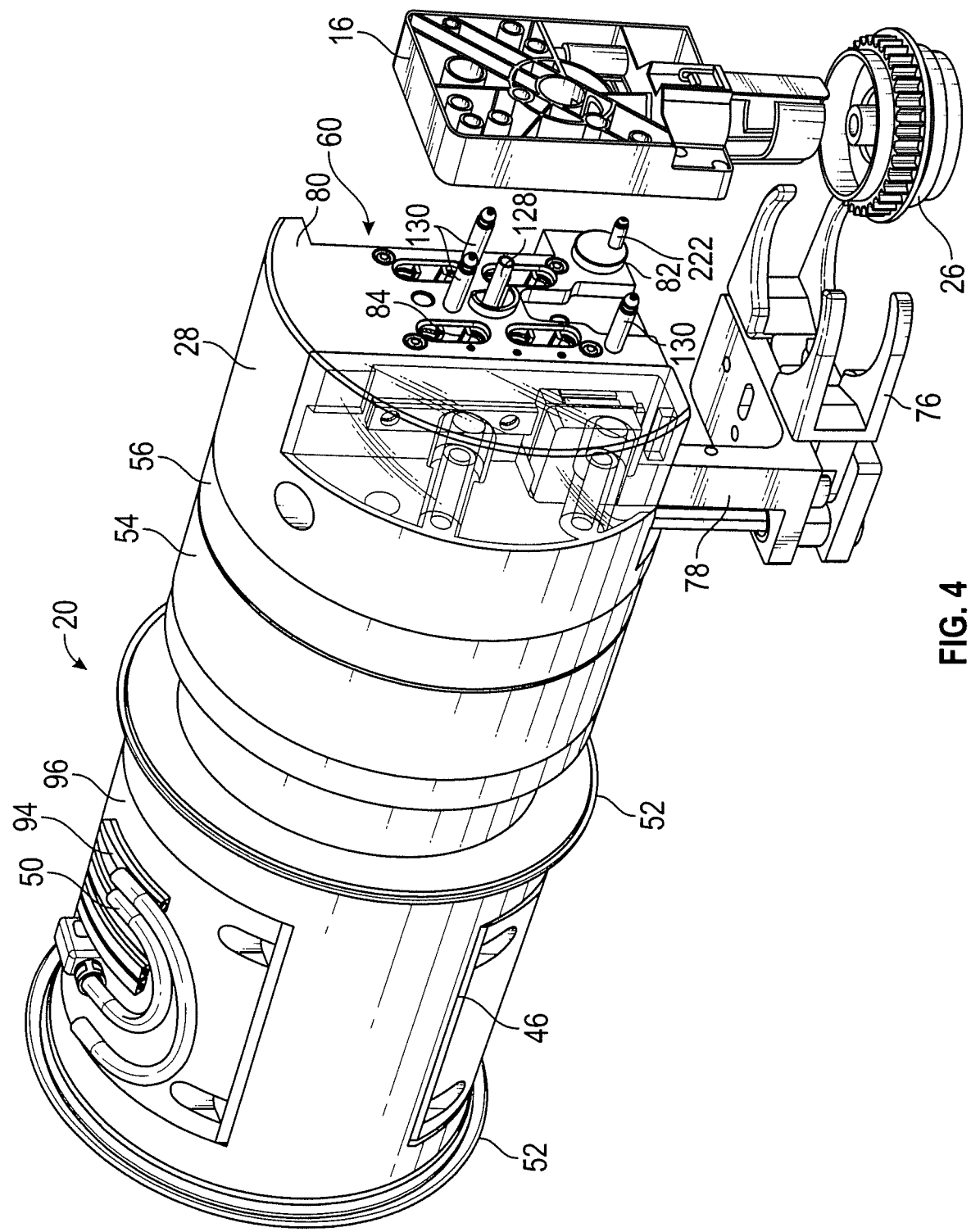
FIG. 4 illustrates a perspective view of an exemplary embodiment of a pump drive mechanism in accordance with aspects of the present disclosure.
Figure 5:
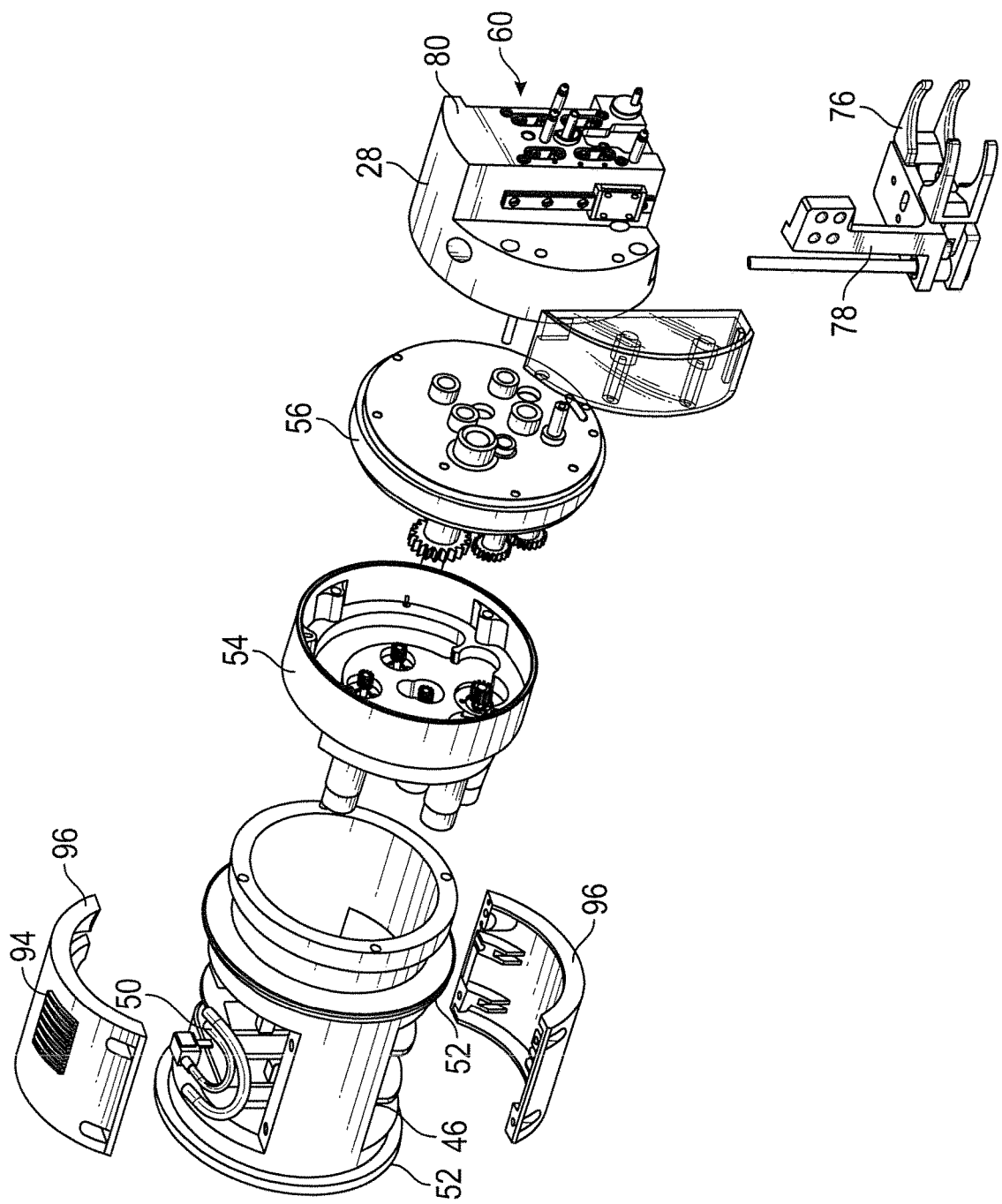
FIG. 5 illustrates an exploded view of the pump drive mechanism of FIG. 4 in accordance with aspects of the present disclosure.

The pump drive mechanism 20 is illustrated in FIG. 4, and in an exploded view in FIG. 5, according to an embodiment. In the embodiment shown in FIGS. 4 and 5, the pump drive mechanism 20 comprises a multitude of sections. At one end of the pump drive mechanism 20 is the rotation housing 46, which holds the drive electronics and includes locking flanges 94 on its housing 96 for flexible tubing 50 which may run from one or more diluent containers and/or waste containers to one or more corresponding manifolds. The rotation housing 46 is capable of rotating around its axis to rotate the rest of the pump drive mechanism 20. The rotation housing 46 includes bearing ribs 52 on its ends, which allow it to rotate. For example, the pump drive mechanism may be configured to rotate through any suitable angle such as up to and including 180°, or more than 180°.

The compounder system also includes a diluent magazine that mounts in a slot 60 located on the side of the pump drive mechanism. The diluent magazine may be a disposable piece configured to receive any number of individual diluent manifolds operable as diluent ports. The diluent manifolds may be modular so they can easily and removably connect to each other, the magazine, and/or connect to the pump drive mechanism 20.

Pump drive mechanism 20 also includes pump head assembly 28. The pump head assembly 28 includes the vial grasping arms 76, the vial lift 78, the pump cartridge grasp 80, the pump piston eccentric drive shaft 82 with drive pin 222, the valve actuation mechanisms 84, as well as the motors that allow the pump drive mechanism 20 to move forward and back and to rotate in order to mix the pharmaceutical in the vial 18 once the diluent has been added to it. The compounder 10 may also include an input screen 86 such as a touch screen 86 as shown in the figures to provide data entry by the user and notifications, instructions, and feedback to the user.

The operation of the compounder system 10 will now be generally described in the flowchart illustrated at FIG. 8, according to an embodiment. In the first step 88, a user inserts a new diluent manifold magazine having a plurality of manifolds (e.g., diluent manifolds and waste manifolds) into the slot 60 on the side of the pump head assembly 28. Manifolds may be loaded into the magazine before or after installing the magazine in the slot 60. The manifolds maintain needles inside the housing of the manifold until the cartridge 16 is later locked in place. The magazine may contain any number of diluent manifolds and vapor waste manifolds. In one illustrative system, there may be three diluent manifolds and one vapor waste manifold. In the next step 92, diluent tubing is connected to corresponding diluent bags. The tubes may be routed through locking flanges on a surface (e.g., the front surface) of the compounder frame to hold them in place. For example, in the illustrated embodiment of FIG. 11, the tubes are held in place with locking flanges 2402 on the frame of the compounder. Alternatively, other types of clips or locking mechanisms known in the art may be used to hold the tubes securely in place. In the illustrated embodiment of FIG. 4, the additional flanges 94 positioned on the outside housing 96 of the pump drive mechanism 20 are provided for securing internal wiring of the compounder. In the next step 98, waste tubing may be connected to the vapor waste bag 44. In other embodiments, tubing may be pre-coupled between the manifolds and associated containers such as diluent containers and/or waste containers and the operations of steps 92 and 98 may be omitted.

If desired, in the next step 100, a new carousel 14 may be loaded into a carousel mounting station such as a carousel hub of the compounder system. The carousel 14 may contain any number of disposable cartridges 16 arranged in a generally circular array. In the next step 110, a vial puck 26 is attached to the top of a vial 18 of a powdered or liquid pharmaceutical for reconstitution and the vial 18 is loaded into the star wheel 22 under the carousel 14 in the next step 112. Step 110 may include loading multiple vials 18 into multiple vial puck recesses in star wheel 22. After one or more vials are loaded into the star wheel, the vials are rotated into position to enable and initiate scanning of the vial label of each vial. In one embodiment, the user will be allowed to load vials into the star wheel until all vial slots are occupied with vials before the scanning is initiated. A sensor may be provided that detects the loading of each vial after which a next vial puck recess is rotated into the loading position for the user. Allowing the user to load all vials into the star wheel prior to scanning of the vial labels helps increase the efficiency of compounding. However, in other implementations, scanning of vial labels may be performed after each vial is loaded or after a subset of vials is loaded. Following these setup steps, the next step 114 is for a user to select the appropriate dosage on the input screen.

After the selection on the input screen 86, the compounder 10 begins operation 116. The star wheel 22 rotates the vial into alignment 118 with the vial grasping calipers 76 of the pump head assembly 28. The vial puck 26 includes, for example, gears that interface with gears coupled to a rotational motor that allow the vial 18 to rotate 120 so that a scanner (e.g., a bar code scanner or one or more cameras) can scan 122 a label on the vial 18. The scanner or camera (and associated processing circuitry) may determine a lot number and an expiration date for the vial. The lot number and expiration date may be compared with other information such as the current date and/or recall or other instructions associated with the lot number. Once the vial 18 is scanned and aligned, in the next step 124 the pump drive mechanism 20 moves forward into position to grip the vial 18 with the calipers 76. The forward movement also brings the mounting posts 130 and locking bayonet 128 on the front of the pump head assembly 28 into matching alignment with corresponding openings on a cartridge 16. In the next step 126 the cartridge 16 is locked in place on the pump head assembly 28 with the locking bayonet 128 and the calipers 76 grip 132 the vial puck 26 on the top of the vial 18. The calipers 76 then remove 132 the vial 18 from the star wheel 22 by moving backward, while at the same time pulling 134 the cartridge 16 off of the carousel 14.

In some embodiments, the cartridge 16 includes a backpack that includes a coiled tube. In this embodiment, in step 136 the pump drive mechanism 20 tilts the cartridge 16 toward the user to expose the end of the tube and prompts 138 the user to pull the tube out of the backpack and connect it to the receiving bag 32. In an alternative embodiment, the tube 38 is exposed on the side of the carousel 14 once the cartridge 16 is pulled away from the carousel 14. In another alternative embodiment, the tube 38 is automatically pushed out (e.g., out of the backpack) thus allowing the user to grab onto the connector located at the end of the tube and connect to the receiving container. The system prompts 138 the user to pull the tube out from the carousel 14 and connect it to the input 34 of the IV bag 32. Once the tube 38 is connected, in step 140 the user may notify the compounder 10 to continue the compounding process by interacting with the input screen 86.

At step 142, the vial 18 is pulled up towards the cartridge 16 so that one or more needles such as a coaxial dual lumen needle of the cartridge 16 pierce the top of the vial puck 26 and enter the interior of the vial 18. Although the example of FIG. 8 shows engagement of the needle with the vial puck after the user attaches the tube from the cartridge to the receiving container, this is merely illustrative. In another embodiment, steps 138 and 140 may be performed after step 142 such that engagement of the needle with the vial puck occurs before the user attaches the tube from the cartridge to the receiving container.

Diluent is pumped at step 144 into the vial 18 through the cartridge 16 and a first needle in the proper dosage. If necessary, a second or third diluent may be added to the vial 18 via a second or third diluent manifold attached to the cartridge 16. Simultaneously, vapor waste is pumped 144 out of the vial 18, through a second needle, through the cartridge 16 and the vapor waste manifold, and into the vapor waste bag 44. The valve actuators 84 on the pump head assembly 28 open and close the valves of the cartridge 16 in order to change the fluid flow paths as necessary during the process. Once the diluent is pumped into the vial 18, the pump drive mechanism 20 agitates the vial 18 in the next step 146 by rotating the vial lift 78 up to, for example 180 degrees such that the vial 18 is rotated between right-side-up and upside-down positions. The agitation process may be repeated for as long as necessary, depending on the type of pharmaceutical that is being reconstituted. Moreover, different agitation patterns may be used depending on the type of drugs being reconstituted. For example, for some drugs, rather than rotating by 180 degrees, a combination of forward-backward, and left-right motion of the pump head may be performed to generate a swirling agitation of the vial. A plurality of default agitation patterns for specific drugs or other medical fluids may be included in the drug library stored in (and/or accessible by) the compounder control circuitry. Once the agitation step is complete, the pump drive mechanism rotates the vial to an upside down position or other suitable position and holds it in place. In some embodiments, a fluid such as a diluent already in the receiving container 32 may be pumped (e.g., through the cartridge or via a separate path) into a liquid waste container to allow room in the receiving container for receiving the reconstituted medicine.

In the next step 148, the valve actuators 84 reorient the valves of the cartridge and the pumping mechanism of the cartridge 16 is activated to pump 150 the reconstituted drug into the receiving bag 32 through the attached tube. Once the drug is pumped into the receiving bag 32, in the next step 152 the pump drive mechanism 20 clears the tube 38 by either pumping filtered air or more diluent through the tube 38 into the receiving bag 32 after another valve adjustment to ensure that all of the reconstituted drug is provided to the receiving bag 32. In some scenarios, a syringe may be used as a receiving container 32. In scenarios in which a syringe is used as the receiving container 32, following delivery of the reconstituted drug to the syringe, a vacuum may be generated in tube 38 by pump drive mechanism 20 to remove any air or other vapors that may have been pushed into the syringe so that, when the syringe is removed from tube 38, the reconstituted drug is ready for delivery to a patient and no air or other unwanted gasses are present in the syringe.

The system then prompts 154 the user to remove the tube 38 from the receiving container 32. The user may then insert the connector (e.g., a Texium® or SmartSite® connector) into its slot in the backpack or carousel and an optical sensor in the pump head may sense the presence of the connector and automatically retract the tube into either the carousel or the backpack. The tube is pulled back into either the carousel 14 or the backpack, depending on which type of system is in use. In the next step 156, the compounder 10 rotates the vial 18 back into alignment with the star wheel 22 and releases it. The used cartridge 16 may also be replaced on the carousel 14. The used cartridge may be released when a sensor in the pump drive determines that the tube has been replaced in the cartridge (e.g., by sensing the presence of a connector such as a Texium® connector at the end of the tube in the backpack of the cartridge through a window of the cartridge). The carousel 14 and/or star wheel 22 then may rotate 158 to a new unused cartridge 16 and/or a new unused vial 18 and the process may be replicated for a new drug. In some circumstances (e.g., multiple reconstitutions of the same drug), a single cartridge may be used more than once with more than one vial.

The cartridges 16 are designed to be disposable, allowing a user to utilize all the cartridges 16 in a given carousel 14 before replacing the carousel 14. After a cartridge 16 is used, the carousel 14 rotates to the next cartridge 16, and the system software updates to note that the cartridge 16 has been used, thus preventing cross-contamination from other reconstituted drugs. Each cartridge 16 is designed to contain all the necessary flow paths, valves, filters and pumps to reconstitute a drug with multiple diluents if necessary, pump the reconstituted drug into the receiving container, pump vapor waste out of the system into a waste container, and perform a final QS step in order to make sure that the proper amount of drug and diluent is present in the receiving container. This complete package is made possible by the specific and unique construction of the cartridge 16, its flow paths, and its valve construction.

Figure 9:
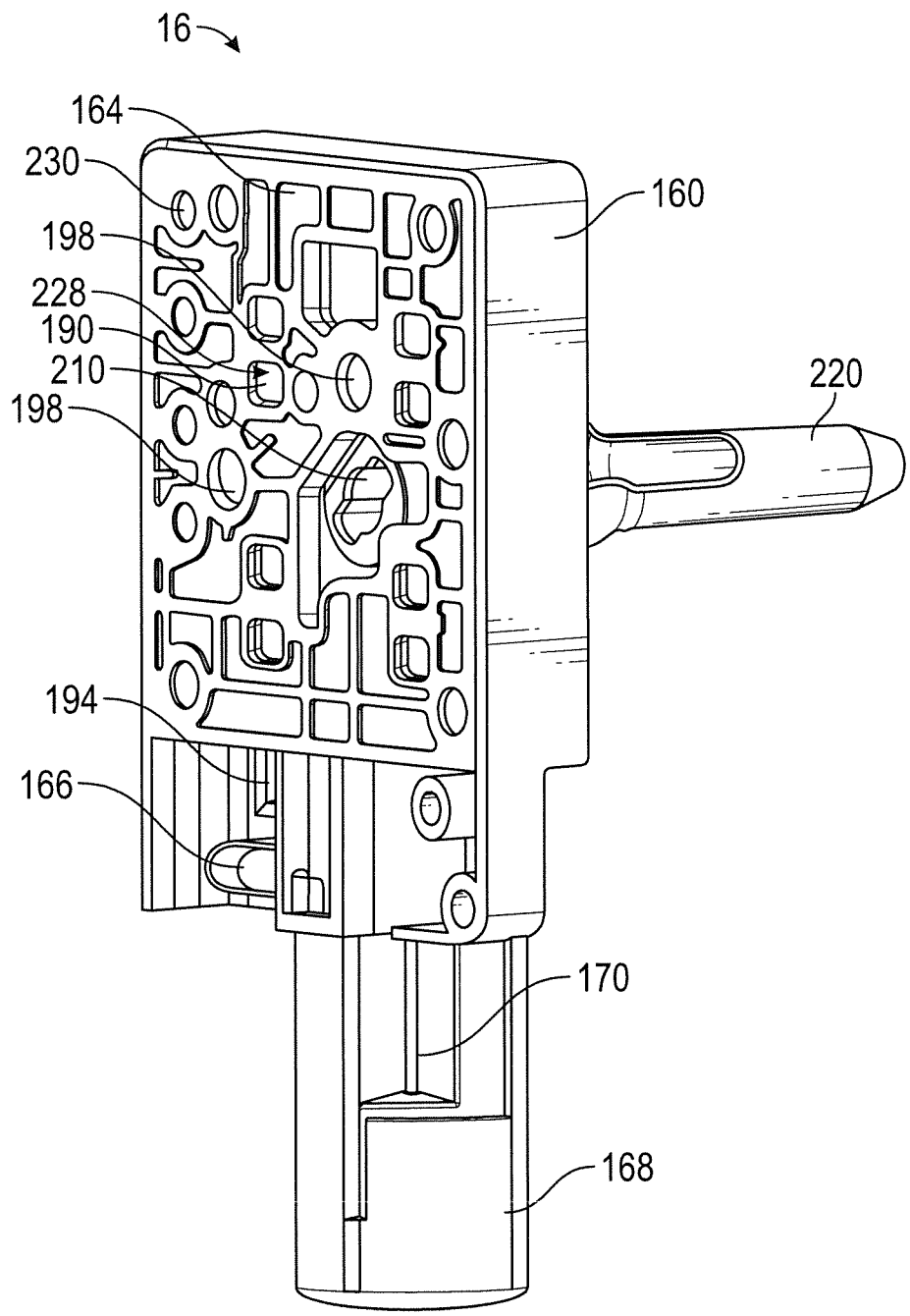
FIG. 9 illustrates a perspective view of an exemplary embodiment of a cartridge in accordance with aspects of the present disclosure.

An embodiment of a cartridge 16 is illustrated in FIG. 9. As shown in FIG. 9, cartridge 16 may include a cartridge frame 160, a cartridge bezel 164, as well as a piston pump 166, a needle housing 168 and a needle assembly 170. The cartridge frame 160 provides the main support for each cartridge 16 and includes diluent chambers, a vapor waste chamber, a pumping chamber, a hydrophobic vent, an exit port, and/or other features as described hereinafter that can be connected to a tube that connects to the receiving container 32.

The frame 160 of the cartridge 16 also includes locating features that allow each cartridge 16 to be removably mounted to the pump head assembly 28. These features include, for example, three openings 198 to receive mounting posts 130 from the pump head assembly 28, and a keyhole 210 that allows a locking bayonet 128 to be inserted therein and turned to lock the cartridge 16 to the pump head assembly 28 for removal from the carousel 14. An outlet port extension 220 may be present in some embodiments. The piston pump 166 is mounted within a chamber with a rod 194 positioned within a silicone piston boot. Furthermore, the bezel 164 includes openings 228 in which the valves 190 of the sealing membrane are located and be accessed by the valve actuators 84. Moreover, the bezel 164 includes openings 230 that allow a fluid manifold to be connected to the diluent and vapor waste chambers in the cartridge 16. As discussed in further detail hereinafter, bezel 164 may also include an opening that facilitates the detection of a connector (e.g., a Texium® or SmartSite® connector) when the user inserts the connector into the provided slot when compounding is complete. In operation, the needles of the fluid manifold enter through the openings 230 in the bezel 164 and pierce the sealing membrane to gain fluidic access to the diluent and vapor waste chambers defined in the cartridge 16 between the sealing membrane and the cartridge frame 160. Further details of various embodiments of the cartridge 16 will be discussed hereinafter.

Figure 10:
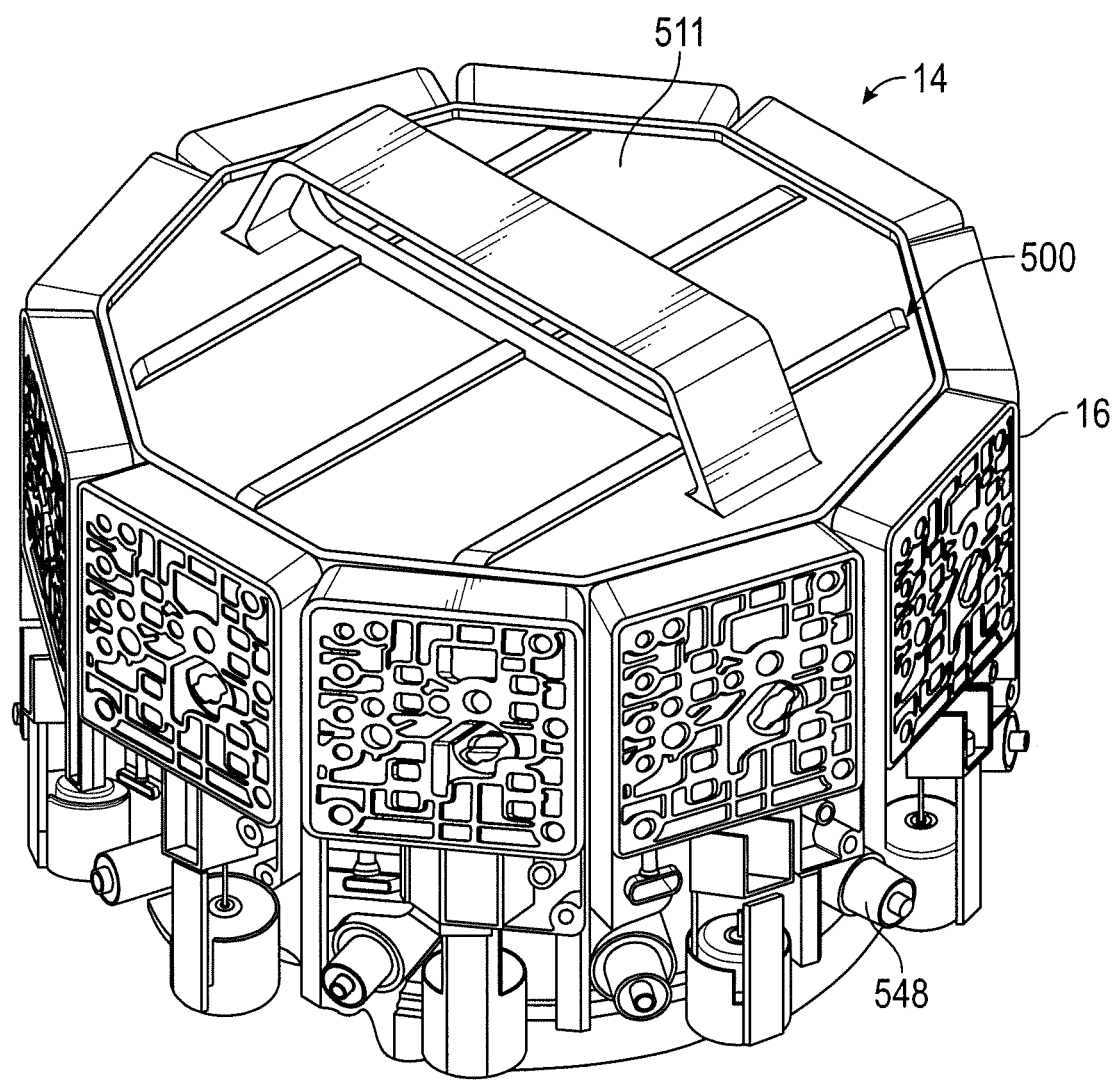
FIG. 10 illustrates a perspective view of an exemplary embodiment of a carousel with a cover in accordance with aspects of the present disclosure.

Referring to FIG. 10, an exemplary embodiment of a carousel 14 removed from the compounder 10 is illustrated, according to an embodiment. The carousel 14 of FIG. 10 includes an array of ten cartridges 16 in this embodiment, but it should be understood that more or fewer cartridges 16 can be present on the carousel 14, leaving some of the carousel 14 pockets 500 empty, or the frame 510 of the carousel can be designed to have more or fewer cartridge pockets 500. In some implementations, the carousel 14 may also, optionally, include a cover 511 that prevents a user from accessing the tubes coupled to each of the cartridges 16 directly. In these implementations, the cover 511 may be removed if necessary to access the backs of the cartridges 16. In the example implementation of FIG. 10, a connector such as a Texium® attachment 548 is disposed adjacent each cartridge 16, the attachment 548 being attached to the tube 38 that runs from the extension 220 on each cartridge 16.

Figure 11:
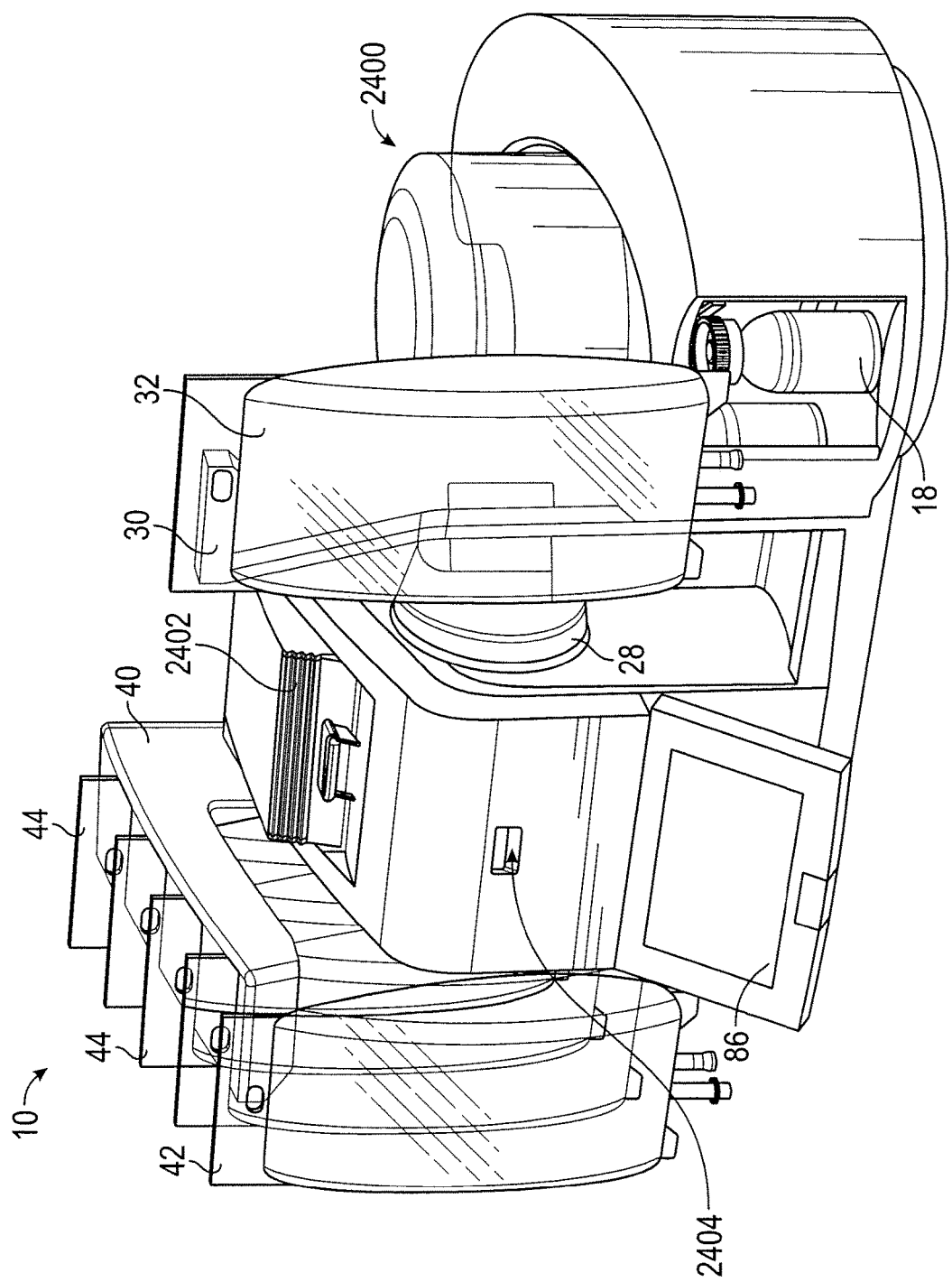
FIG. 11 illustrates a front perspective view of another exemplary embodiment of a compounding system in accordance with aspects of the present disclosure.

FIGS. 11-14 show the compounder 10 according to another embodiment. As shown in FIG. 11, holding apparatus 40 may be implemented as an extended arm providing support for mounting devices for each of containers 42 and 44. Holding apparatus 40 and holding apparatus 30 may each include one or more sensors such as weight sensors configured to provide weight measurements for determining whether an appropriate amount of fluid has been added to or removed from a container or to confirm that fluid is being transferred to and/or from the appropriate container (e.g., that the appropriate diluent is being dispensed). A scanner 2404 may be provided with which each diluent container and/or the receiving container can be scanned before and/or after attachment to compounder 10. As shown in FIG. 11, a carousel cover 2400 and tube management structures 2402 may also be provided on compounder 10 in various embodiments. For example, tubes connected between containers 42 and/or 44 and corresponding manifolds can each be mounted in a groove of tube management structure 2402 to prevent tangling or catching of the tubes during operation of compounder 10.

An opening may be provided by which vials 18 can be installed in the star wheel. Additionally, an exterior pump 2500 may be provided for pumping non-toxic liquid waste from, for example, receiving container 32 to a waste container 44 (e.g., for pumping a desired amount of saline out of receiving container 32 quickly and without passing the liquid waste through a cartridge and/or other portions of the compounder).

A fluidics module 2504 may be provided that includes several container mounts which may be used for hanging diluent and waste containers and may include sensor circuitry for sensing when a container has been hung and/or sensing the weight of the container. In this way, the operation of compounder 10 can be monitored to ensure that the correct diluent contain has been scanned and hung in the correct location and that the waste is being provided in an expected amount to the appropriate waste container.

Figure 12:
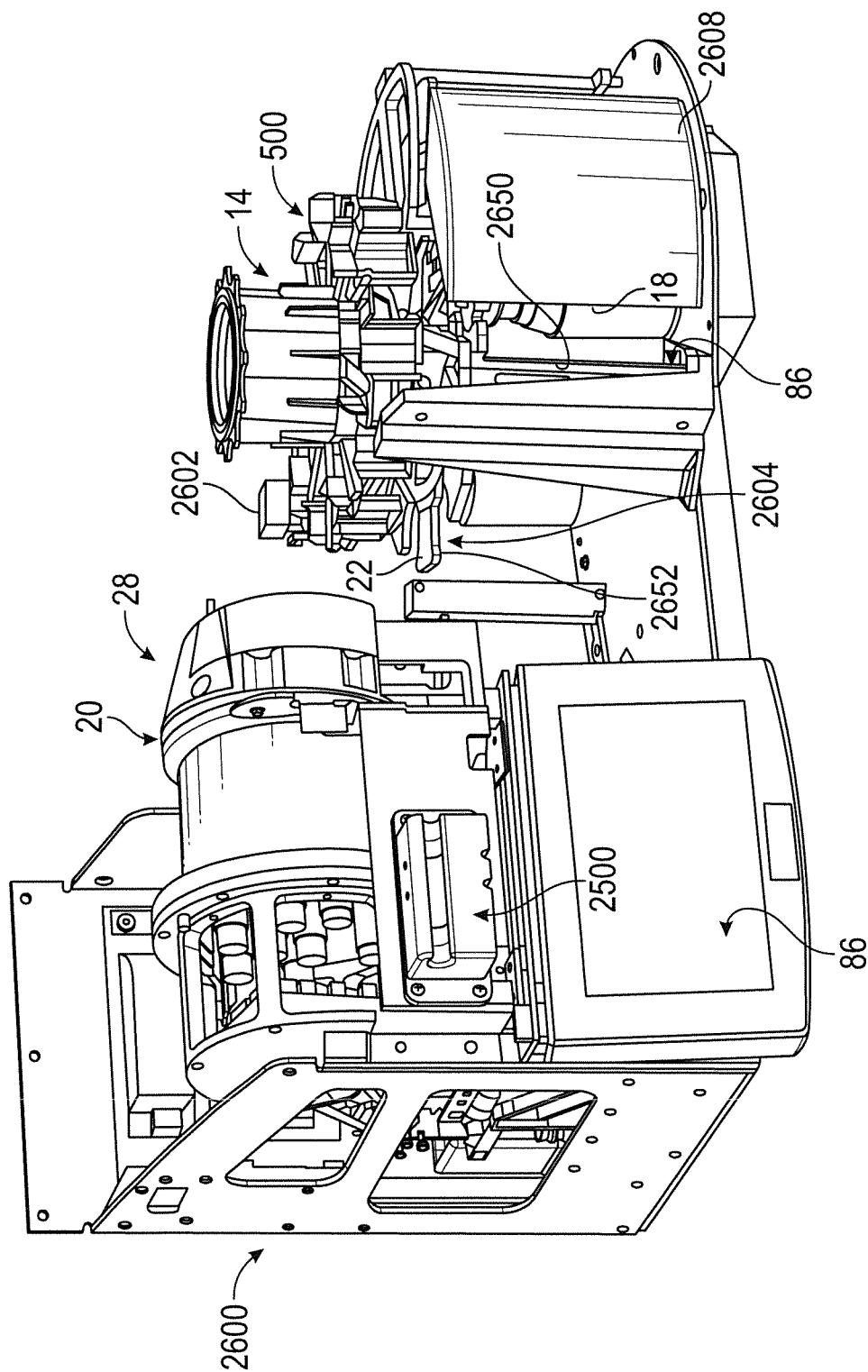
FIG. 12 illustrates a front perspective view of the compounding system of FIG. 11 with portions of the housing removed in accordance with aspects of the present disclosure.

As shown in FIG. 12, pump 2500 and display 86 may be mounted to a chassis 2600. Pump drive 20 may be mounted partially within the chassis 2600 with pump head assembly 28 extending from the chassis to a position which allows the pump head assembly to rotate (e.g., to turn over or agitate a vial). Carousel 14 is also shown in FIG. 12 without any cartridges mounted therein so that cartridge mounting recesses 500 can be seen.

Star wheel 22 (sometimes referred to herein as a vial tray) is shown in FIG. 12 with several empty vial puck recesses 2604. Vial tray 22 may be rotated and an actuating door 2608 may be opened to facilitate loading of vials 18 into the vial puck recesses 2604 in vial tray 22. In some embodiments, door 2608 may be closed before rotation of vial tray 22 to ensure that the operator's fingers are not in danger of injury from the rotating tray. However, this is merely illustrative. In other embodiments a sensor such as sensor 2650 (e.g., a light curtain) may be provided instead of (or in addition to) door 2608 to sense the presence of an operator in the vicinity of tray 22 and prevent rotation of the tray if the operator or any other obstruction is detected.

Similarly, a lid may be provided for carousel 14 to prevent contamination of cartridges 16 loaded therein, and to prevent injury to an operator due to rotation of the carousel. A lid sensor (not shown) may also be provided to detect the position (e.g., an open position or a closed position) of the lid. Rotation of carousel 14 may be prevented if the lid is not detected in a closed position by the lid sensor.

Each vial 18 that is inserted may be detected using a sensor such as sensor 2652 (e.g., a load sensor or an optical sensor) when placed in a vial puck recess 2604. When detected, the inserted vial may be moved to a scanning position by rotating vial tray 22 and then the inserted vial 18 may be rotated within its position in vial tray 22 using a vial rotation motor 2602 to allow the vial label to be scanned.

Figure 13:
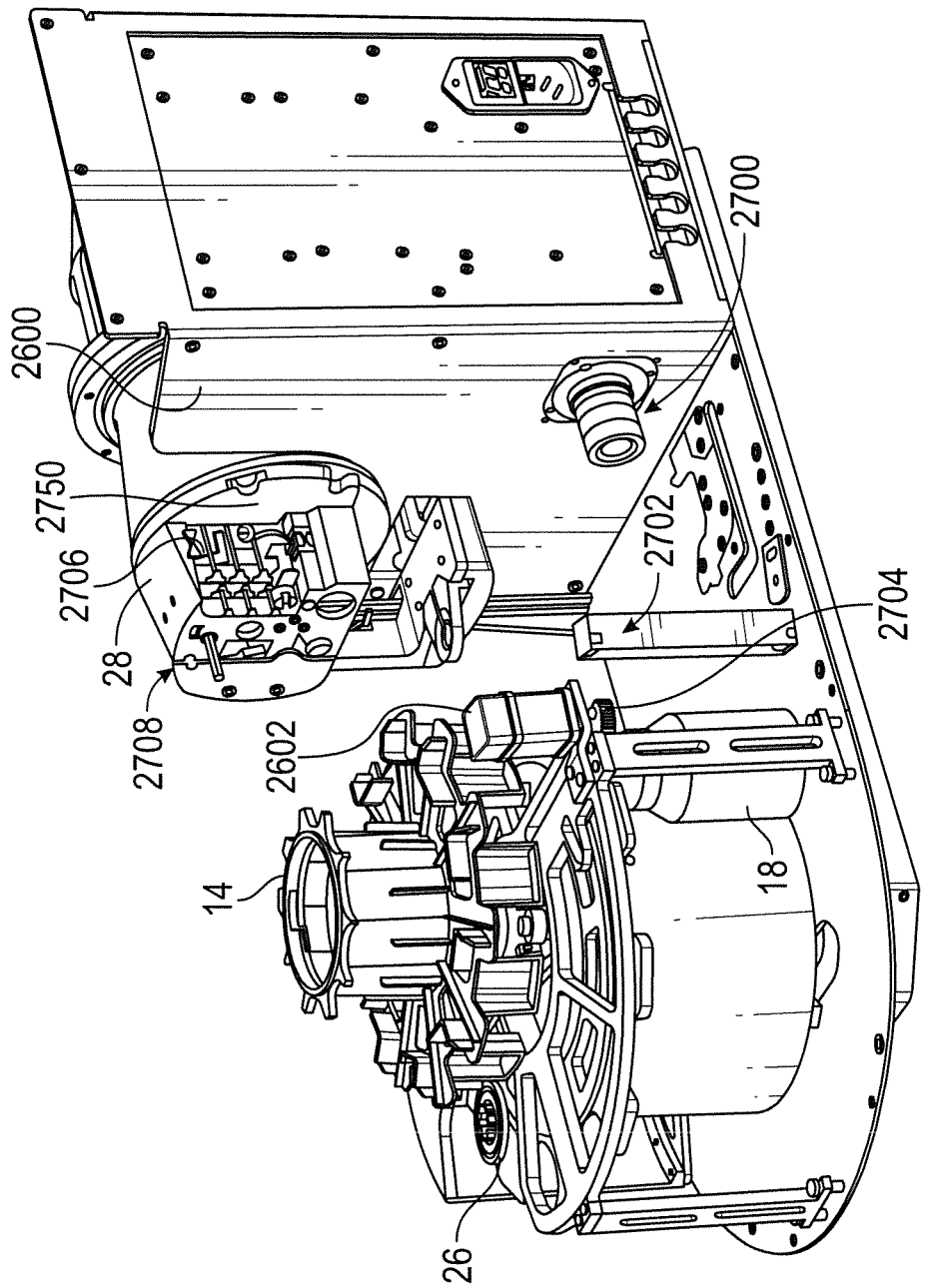
FIG. 13 illustrates a rear perspective view of the compounding system of FIG. 11 with portions of the housing removed in accordance with aspects of the present disclosure.

A reverse perspective view of compounder 10 is shown in FIG. 13 in which scanning components can be seen. In particular, a camera 2700 is mounted in an opening in chassis 2600 and configured to view a vial 18 in a scanning position. Motor 2602 may rotate vial 18 through one or more full rotations so that camera 2700 can capture images of the vial label. In some embodiments, an illumination device 2702 (e.g., a light-emitting diode or other light source) may be provided that illuminates vial 18 for imaging with camera 2700.

As shown in FIG. 13 one or more gears 2704 coupled to motor 2602 may be provided that engage corresponding gears on a vial puck 26 to which a vial 18 is attached at the scanning position. The vial tray 22 may be rotated so that the vial puck gears engage the rotation motor gears so that when the motor 2602 is operated the vial 18 is rotated.

FIG. 13 also shows how a magazine 2706 containing one or more manifolds may be mounted in a recess in pump head assembly 28. A magazine slot in magazine 2706 for the vapor waste manifold may be keyed to prevent accidental connection of a diluent manifold in that slot (or a waste manifold in a diluent slot in the magazine). Other diluent slots in magazine 2706 may have a common geometry and thus any diluent manifold can fit in the magazine diluent slots. One or more manifold sensors such as manifold sensor 2750 (e.g., an optical sensor) may be provided in the manifold recess in pump head assembly 28. Manifold sensor 2750 may be configured to detect the presence (or absence) of a manifold in a manifold recess (slot) in magazine 2706 to ensure that an appropriate manifold (e.g., a diluent manifold or waste manifold) is loaded at the expected position for compounding operations. In this way, the pump head may detect a manifold presence. The pump head and/or manifold sensors may communicate with the diluent load sensors to ensure proper positioning of the diluent manifolds. Various operational components 2708 such as valve actuators, needle actuators, mounting posts, a locking bayonet, and a drive pin can also be seen extended from pump head assembly 28 which are configured to secure and operate a pump cartridge 16.

Compounder 10 may include additional components such as a chassis base and chassis housing, and an internal electronics assembly. Pump drive 20 may be seated in an opening in the chassis housing that allows pump head assembly 28 to protrude from the chassis housing. Processing circuitry for managing operations of compounder system 10 may be included in the electronics assembly.

Carousel 14 may be placed onto a carousel hub and rotated by a vial tray and carousel drive assembly operating to rotate the hub to move a selected cartridge in the carousel into position to be retrieved and operated by pump drive 20. The vial tray and carousel drive assembly may include separate drive assemblies for the vial tray and for the carousel such that vial tray 22 and carousel 14 may be rotated independently.

Figure 14:
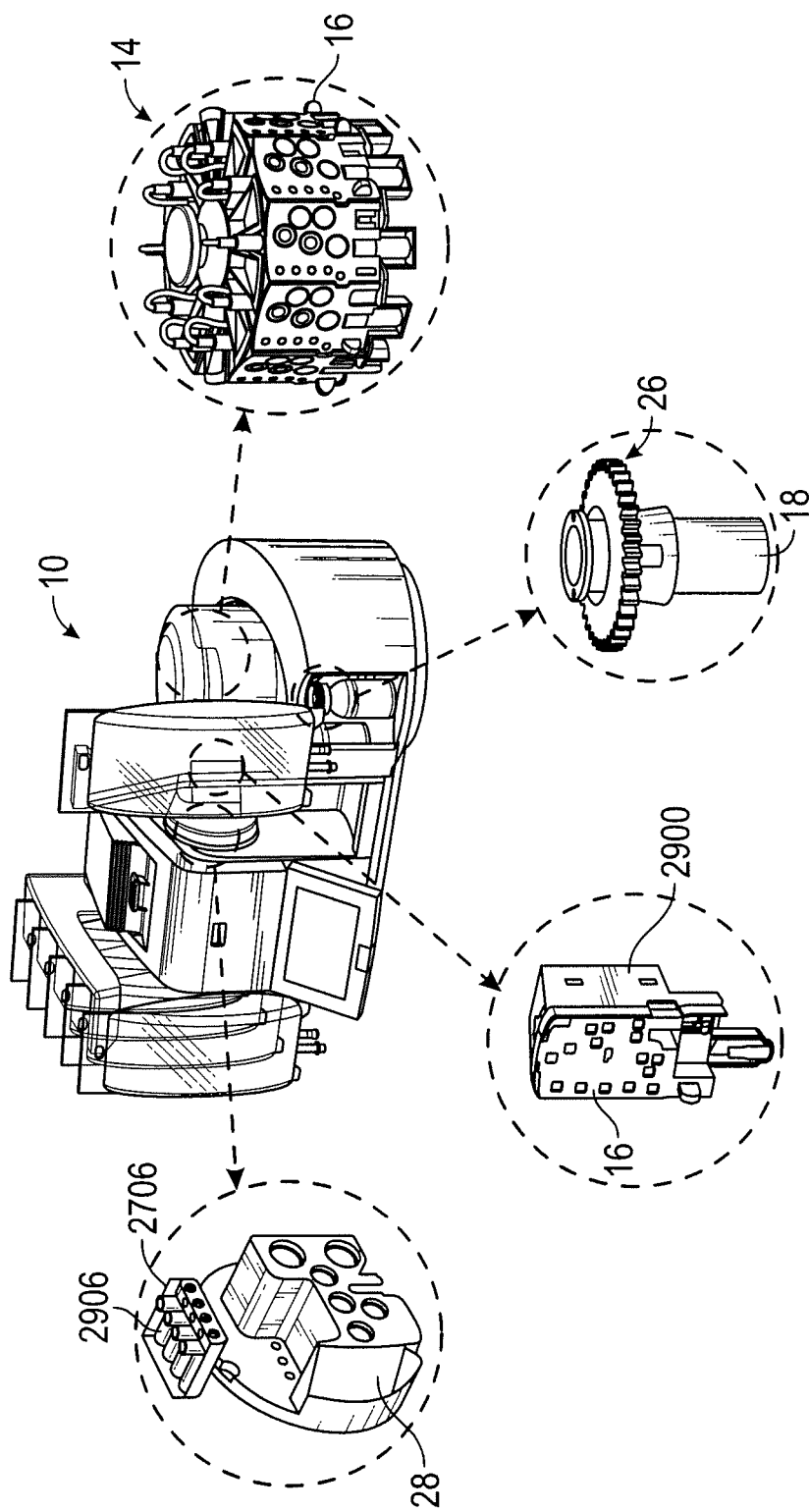
FIG. 14 illustrates a perspective view of the compounding system of FIG. 11 with various components shown in enlarged views for clarity in accordance with aspects of the present disclosure.

FIG. 14 shows another perspective view of compounder 10 highlighting the locations of various particular components such as the carousel 14 with cartridges 16 mounted therein, a cartridge 16 having a backpack 2900, a vial puck 26 for mounting vials 18, and pump head assembly 28 with a diluent magazine 2706 containing a plurality of manifolds 2906 in accordance with an embodiment. Further features of compounder 10 will be described hereinafter in connection with FIG. 15 et seq.

The cartridges 16 are designed to be disposable, allowing a user to utilize all the cartridges 16 in a given carousel 14 before replacing the carousel 14. After a cartridge 16 is used, the carousel 14 rotates to the next cartridge 16, and the system software updates to note that the cartridge 16 has been used, thus preventing cross-contamination from other reconstituted drugs. Each cartridge 16 is designed to contain all the necessary flow paths, valves, filters, pistons, and pumps to reconstitute a drug with multiple diluents if necessary, pump the reconstituted drug into the receiving container, pump vapor waste out of the system into a waste container, and perform a final QS step in order to make sure that he proper amount of drug and diluent is present in the receiving container. The amount of diluent pumped into vials for reconstitution and the amount of medication pumped out of vials to the receiving container are controlled by the volumetric piston pump in the cartridge which can be compared against weights obtained by the gravimetric scales (e.g., one or more diluent load cells and a receiving container load cell) of the compounder for quality control. This complete package is made possible by the specific and unique construction of the cartridge 16, its flow paths, and its valve construction.

Figure 15:
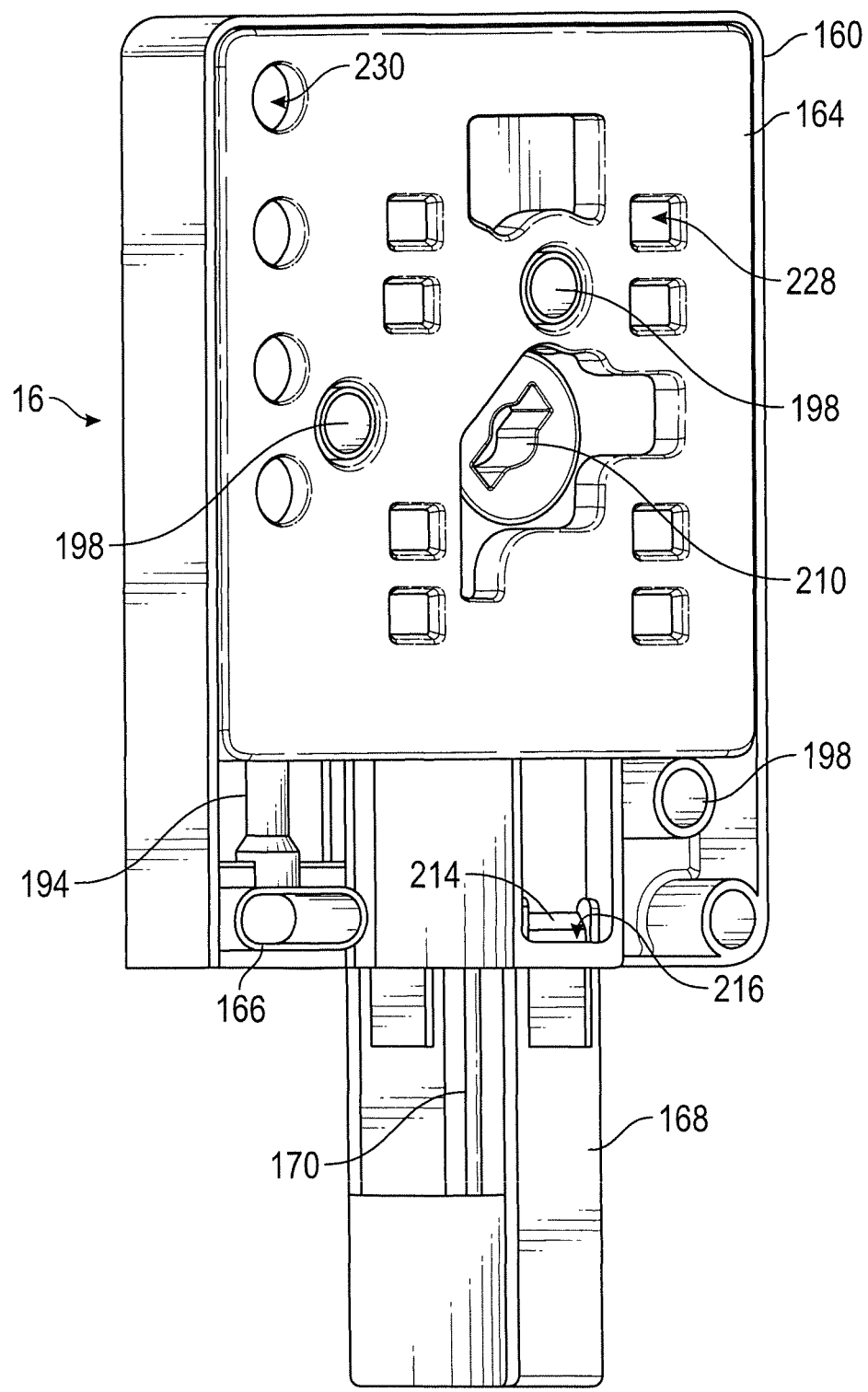
FIG. 15 illustrates a perspective view of the cartridge of FIG. 9 in accordance with aspects of the present disclosure.
Figure 16:
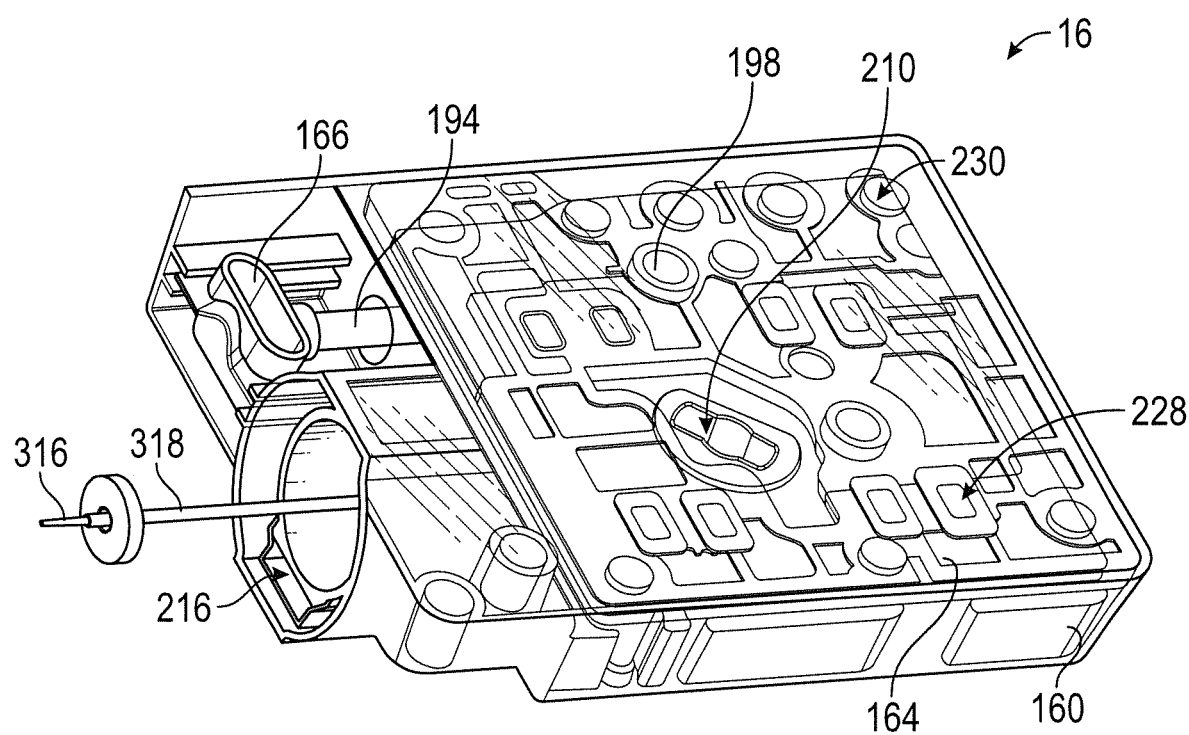
FIG. 16 illustrates a perspective view of the cartridge of FIG. 9 with a transparent bezel in accordance with aspects of the present disclosure.
Figure 17:
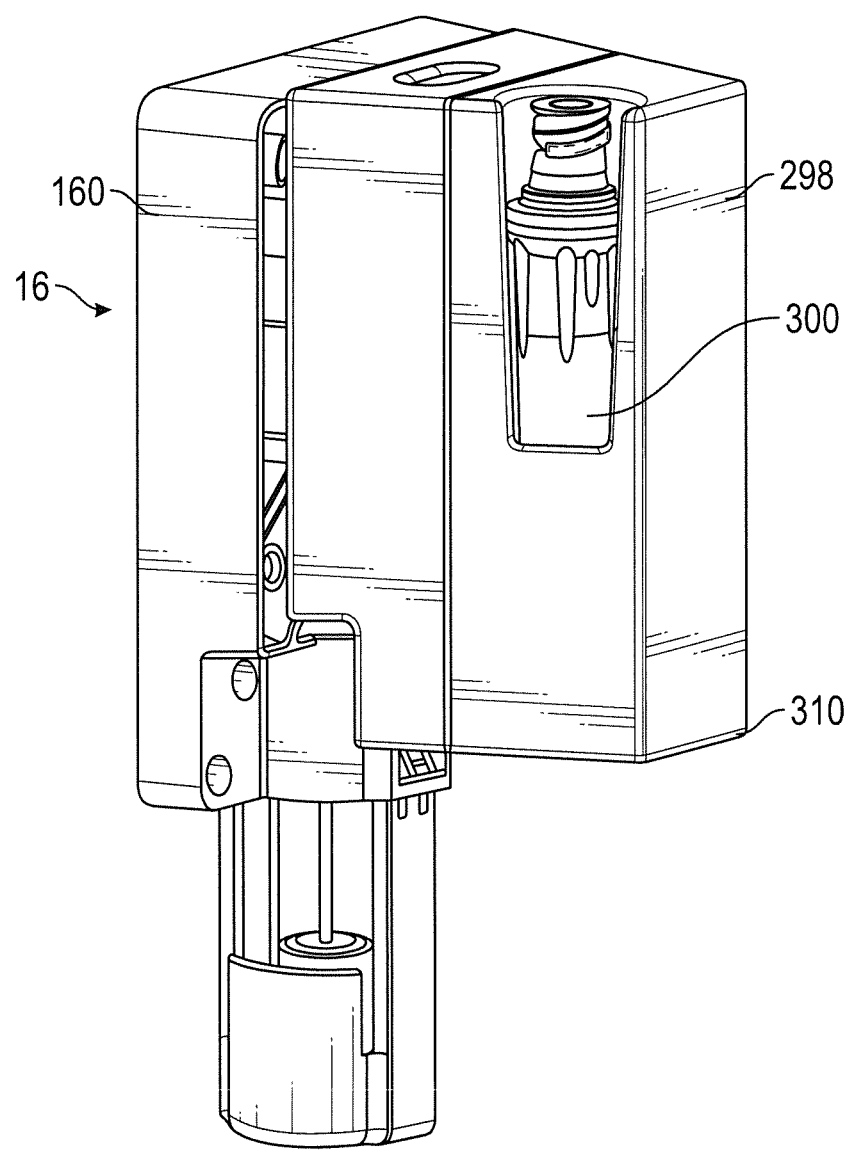
FIG. 17 illustrates a perspective view of an exemplary embodiment of a cartridge with a backpack attachment in accordance with aspects of the present disclosure.
Figure 18:
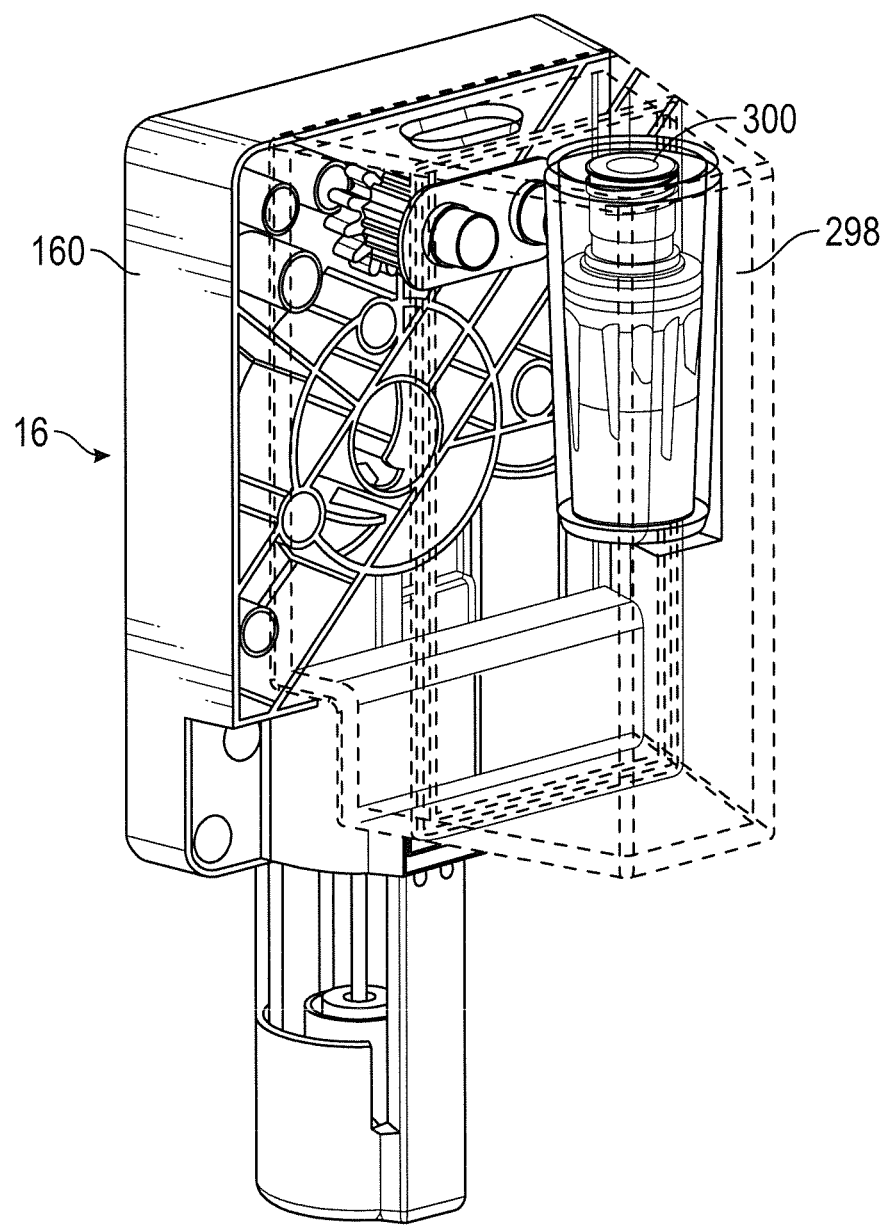
FIG. 18 illustrates a perspective view of the cartridge of FIG. 17 with a transparent backpack attachment in accordance with aspects of the present disclosure.
Figure 19:
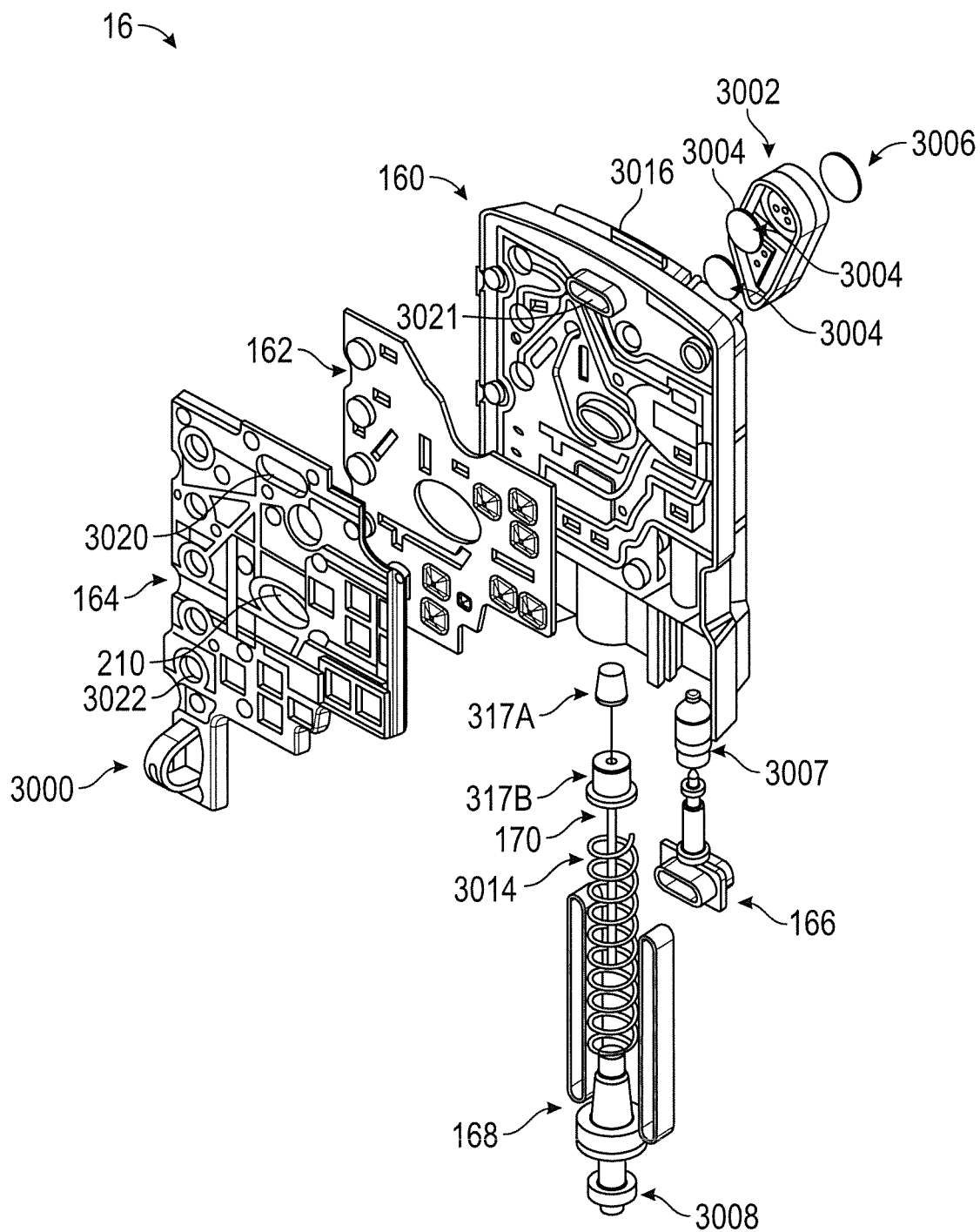
FIG. 19 illustrates an exploded perspective view of another embodiment of a pump cartridge in accordance with aspects of the present disclosure.

Various embodiments of a cartridge 16 are illustrated in FIG. 15-20B. A fully constructed cartridge 16 is shown in FIGS. 15 and 16 in one embodiment. A cartridge 16 having a tube management structure implemented as a backpack for the cartridge is shown in FIGS. 17 and 18. An exploded version of a cartridge 16 is illustrated in FIG. 19 and shows three main portions of the cartridge 16: the cartridge frame 160, the cartridge sealing membrane 162, the cartridge bezel 164, as well as the piston pump 166, the needle housing 168 and the needle assembly 170 according to an embodiment.

Figure 20A:
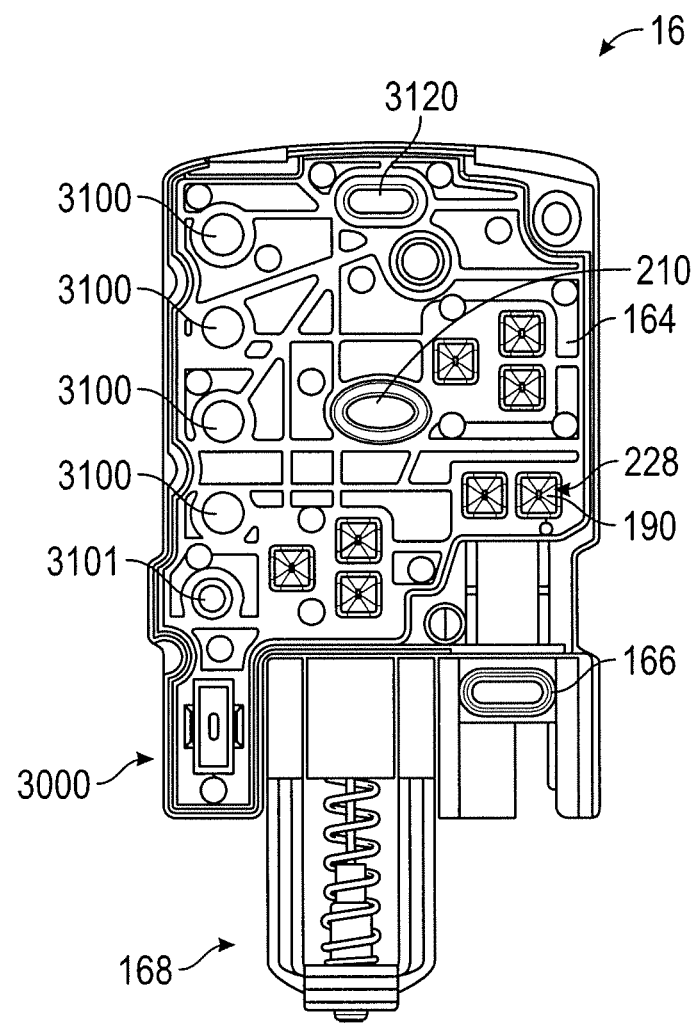
FIG. 20A illustrates a rear plan view of the cartridge of FIG. 19 in accordance with aspects of the present disclosure.
Figure 20B:
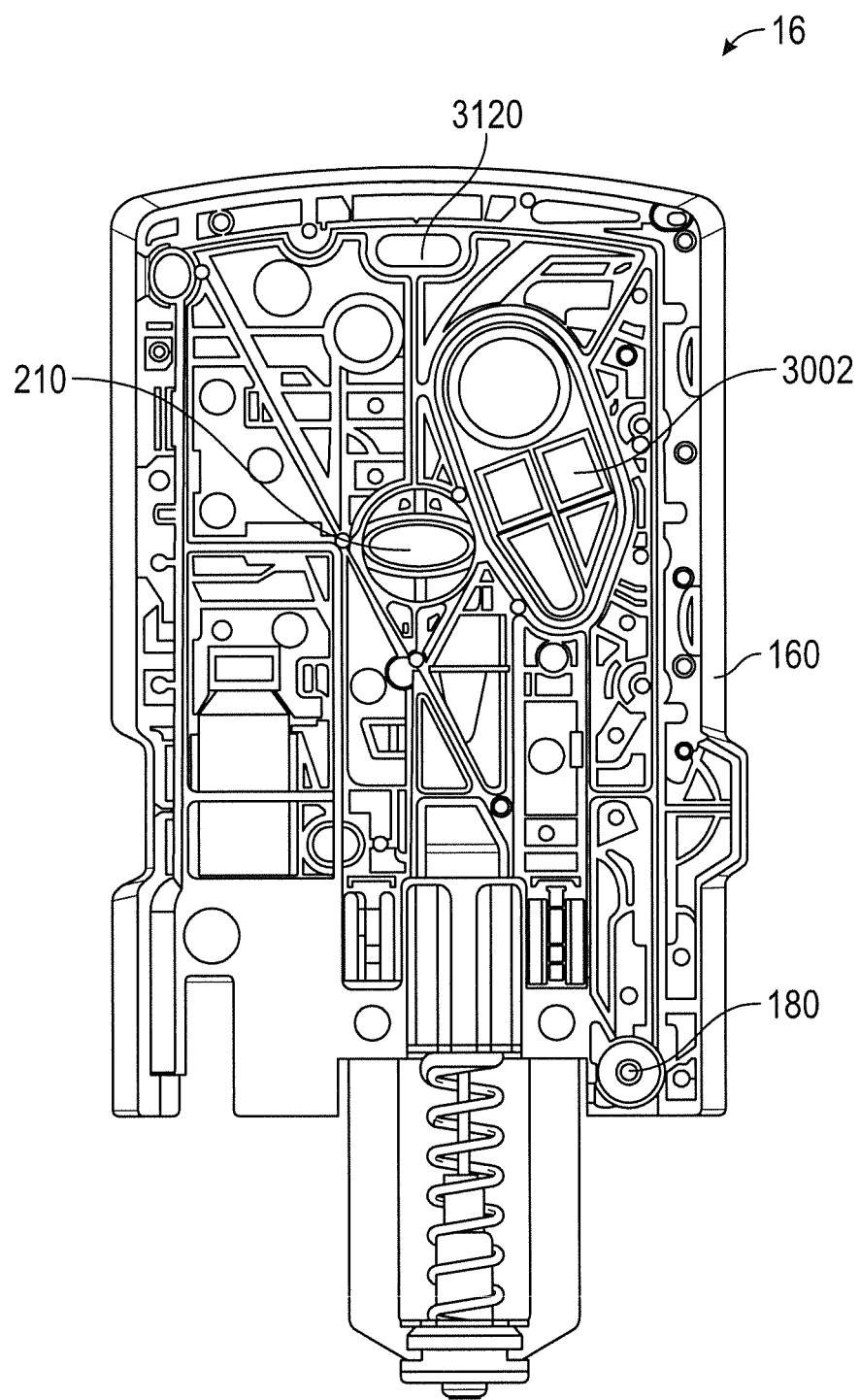
FIG. 20B illustrates a front plan view of the cartridge of FIG. 19 in accordance with aspects of the present disclosure.

A fully constructed cartridge 16 is shown in FIGS. 20A and 20B in one embodiment. Various features of the cartridge of FIGS. 19, 20A, and 20B are shown in FIGS. 21-31.

As shown in FIG. 15, a front view of the cartridge 16 is illustrated. Cartridge frame 160 provides the main support for each cartridge 16. Piston pump 166 and a cartridge needle housing 168 to hold the needle assembly 170 are provided that can be operated to move liquids and waste vapor to and from vial 18 during reconstitution and filling of receiving container 32. Valves 190 are positioned with respect to various internal flow paths within cartridge 16 for diluents, vapor waste, filtered air, and reconstituted drugs and are operable to modify and control the internal flow paths when desired.

Frame 160 of the cartridge 16 also includes locating features that allow each cartridge 16 to be removably mounted to the pump head assembly 28. These features include three openings 198 to receive mounting posts 130 from the pump head assembly 28, and a keyhole 210 that allows a locking bayonet 128 to be inserted therein and turned to lock the cartridge 16 to the pump head assembly 28 for removal from the carousel 14.

The cartridge needle housing 168 extends from the bottom of the cartridge frame 160 and may be designed to be removable by snapping a pair of locking flanges 214 on the needle housing 168 into flange openings 216 in the cartridge frame 160. The cartridge needle housing 168 is designed to prevent accidental user contact with the needle assembly 170 and to maintain the sterility of one or more needles of the needle assembly (see, e.g., needles 316 and 318 of FIG. 31). The needle housing 168 also receives the vial puck 26 in a position to allow the needles to pierce the vial puck 26.

A sealing membrane may be disposed between frame 160 and bezel 164 to form sealed internal flow paths in cartridge 16 in cooperation with internal features of frame 160 and bezel 164 as described in further detail hereinafter.

Before describing the various fluid flow paths in the cartridge 16, the operation of the pumping and valve mechanisms will be described with reference to FIGS. 3, 4, 6 and 7. A piston pump such as piston pump 166 acts as a positive displacement pump that has significant advantages over a traditional peristaltic pump mechanism. First, it has the best rate accuracy and flow continuity regardless of the pump's orientation or environmental conditions. Second, it is able to push an excess of 50 psi into elastomeric pumps. The piston pump 166 may be positioned within the cartridge 16 in a silicone piston pump boot. The pump mechanism is driven by a motor in the pump motor mechanism 20 which rotates an eccentric drive shaft 82 and drive pin 222 on the pump head assembly 28 which controls the movement of the piston 166 as well as the valve actuators 84. In operation, the cartridge 16 is placed on the cartridge grasp 80 on the locating posts 130 and locked in place by the locking bayonet 128. This aligns the valves disposed in openings 228 of bezel 164 with the valve actuators 84 and the eccentric drive shaft 82 and pin 222 with the piston pump 166. The piston 166 is driven by the eccentric drive pin 222. The pin 222 is parallel to but offset from the rotational axis of the drive shaft, which produces sinusoidal motion that is converted to an axial movement of the piston 166.

Figure 6:
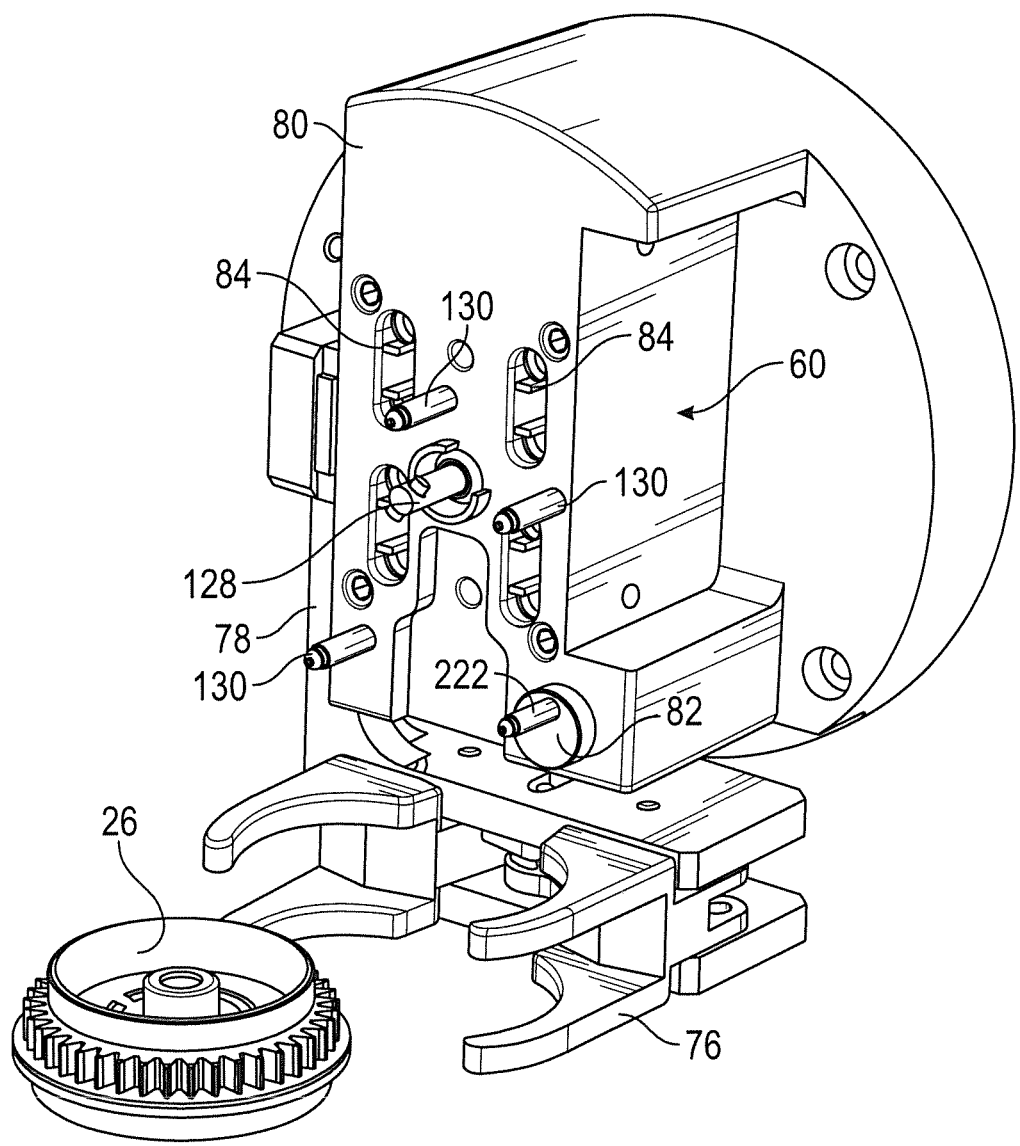
FIG. 6 illustrates a perspective view of a pump head assembly with an exemplary embodiment of a gripping system and vial puck in accordance with aspects of the present disclosure.
Figure 7:
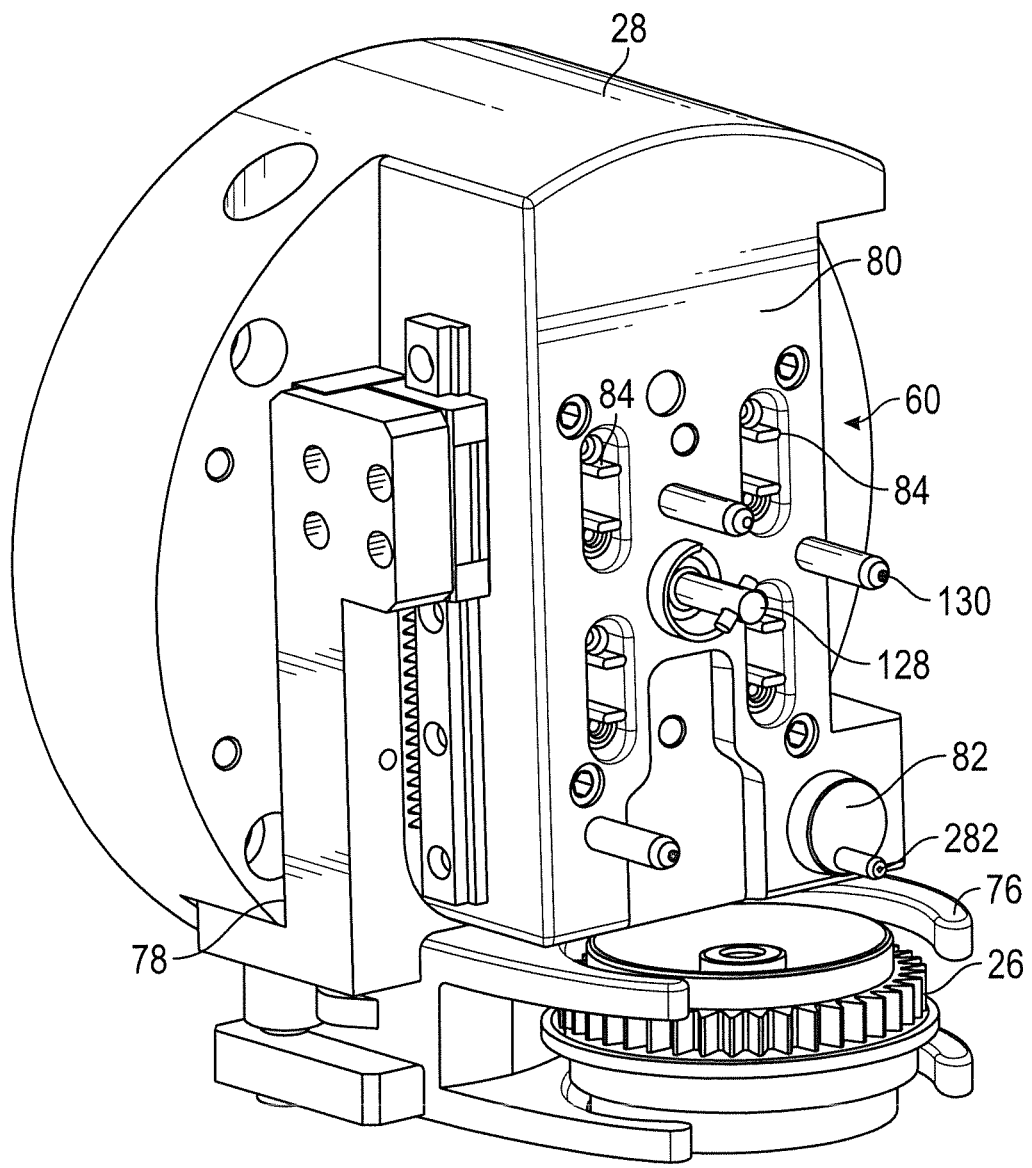
FIG. 7 illustrates a perspective view of the pump head assembly, gripping system and vial puck of FIG. 6 in accordance with aspects of the present disclosure.

The valve actuators 84 are illustrated in FIGS. 6 and 7, which show the pump head assembly 28 removed from the rest of the pump motor mechanism 20. Each one of the valves in openings 228 has a corresponding valve actuator 84 that is controlled by a geared cam to cause axial movement of the valve actuator 84 into contact with the valve to close the valve and away from the valve to open the valve.

In one embodiment, eight valve actuators 84 are provided, one for each valve, and they are aligned with the positions of the valves so they can extend through the openings 228 in the bezel 164 of the cartridge 16 and contact the valves. The valve actuators 84 are software controlled so that they can automatically cause the valves to open and close depending on which internal flow paths within cartridge 16 are to be opened and closed.

The valve actuators 84 are operated at different times in the pumping cycle depending on the required fluid flow path. The fill portion of the piston 166 starts as the piston rod 194 moves, and the inlet valve is opened and the outlet valve is closed. Other valves will be opened and closed depending on the necessary fluid flow paths. At the end of the fill portion of the cycle when the piston 166 is at the bottom dead center position, the valve actuation changes to close the inlet and open the outlet valves. At this point, the delivery portion of the cycle starts and the piston 166 moves in the opposite direction. The delivery portion of the cycle ends when the piston 166 reaches the top dead center location, which is the home location. When the piston 166 reaches this position, a new cycle is started.

The movement of the eccentric drive shaft 82 can be in a clockwise direction under normal conditions when delivering fluid and counter clockwise when pulling fluid. The pump mechanism can be made to pump backwards depending on the required flow path. The drive may be prevented from being inadvertently back driven in either direction by the effects of pressure in the disposable line up to 50 psi.

An alternative embodiment of the cartridge 16 utilizing a "backpack" to coil the flexible tubing 38 is illustrated in FIGS. 17 and 18. The backpack 298 is attached to the back of the cartridge frame 160 and one end of the flexible tube 38 is attached to an outlet port on the back of the cartridge frame 16. The backpack 298 comprises a housing 310 and may include a tube control mechanism defined in a chamber that can rotate or otherwise operate to coil the flexible tubing 38. At the opposite end of the tubing from the outlet port is a connector 300 (e.g., an ISO Luer connector such as a Texium® attachment) that a user can pull out of the backpack 298 and attach to the receiving bag 32. In some embodiments, the tubing attached to the connector 300 may be automatically extended from within backpack 298 to facilitate attachment by the user. Upon completion of the filling of the bag 32, the tube control mechanism can draw the flexible tubing 38 back into the backpack 298 and out of the way so that the next cartridge 16 in the carousel 14 can be utilized. Retraction of the flexible tubing may be automatic once the ISO Luer is placed into the opening in the backpack.

Turning now to FIG. 19, an exploded perspective view of another embodiment of cartridge 16 shows three main portions of the cartridge 16: the cartridge frame 160, the cartridge sealing membrane 162, the cartridge bezel 164, as well as the piston pump 166, the needle housing 168 and the needle assembly 170. In the example of FIG. 19, cartridge bezel 164 includes an additional opening 3022 to provide access to a pressure dome formed on membrane 162 to allow sensing of pressure in the fluid pathways of cartridge 16. An air-in-line sensor fitment 3000 is also provided that is configured to mate with an air-in-line (AIL) sensor in the compounder.

In order to control the flow of gasses such as vapor waste and sterile air within the cartridge, cartridge 16 may be provided with gas flow control structures such as an air filter 3006 and one or more check valve discs 3004 that mount to frame 160 with a check valve cover 3002. Air filter 3006, check valve discs 3004, and check valve cover 3002 may cooperate to allow vapor waste to flow in only one direction from the vial to the waste port and to allow sterile (filtered) air to flow in only one direction into the cartridge from a vent adjacent the air filter to the vial. In this way, unwanted vapor waste may be prevented from flowing out of the pump cartridge and may be instead guided to a vapor waste container.

As shown in FIG. 19, piston 166 may include a piston boot 3007 that, for example, provides one or more moveable seals (e.g., two moveable seals) for controlling the volume of a pump chamber when piston 166 is actuated. FIG. 19 also shows various structures for control of another embodiment of needle housing 168 in which needle assembly 170 includes a dual lumen needle with a first needle overmold 317A, a second needle overmold 317B, a needle spring 3014, and a needle membrane 3008. An opening 3020 in bezel 164 may be provided that aligns with a corresponding opening 3021 in frame 160 to allow a view through cartridge 16 (e.g., by a sensor of the pump drive mechanism) into a backpack that is mounted to cartridge 16 as will be described in further detail hereinafter. A protrusion 3016 formed on a top side of cartridge frame 160 may be provided as a mounting structure for the backpack.

FIGS. 20A and 20B show assembled views of the cartridge embodiment shown in FIG. 67 from the bezel side and frame side respectively in which an opening 3120 (formed by openings 3020 and 3021 of FIG. 19) that allows a view completely through cartridge 16 can be seen. As shown in FIG. 20A, in some embodiments, cartridge 16 may include four diluent and waste ports 3100 and a pressure dome 3101. For example, three of the ports 3100 may be configured as diluent ports and one of the ports 3100 may be configured as a waste port. A pressure sensor in the pump head assembly 28 may determine pressure within the fluid pathways in cartridge 16 by contacting pressure dome 3101. Each of the ports 3100 may be formed from an opening in bezel 164 and a chamber located behind a portion of membrane 162 in frame 160.

Figure 21:
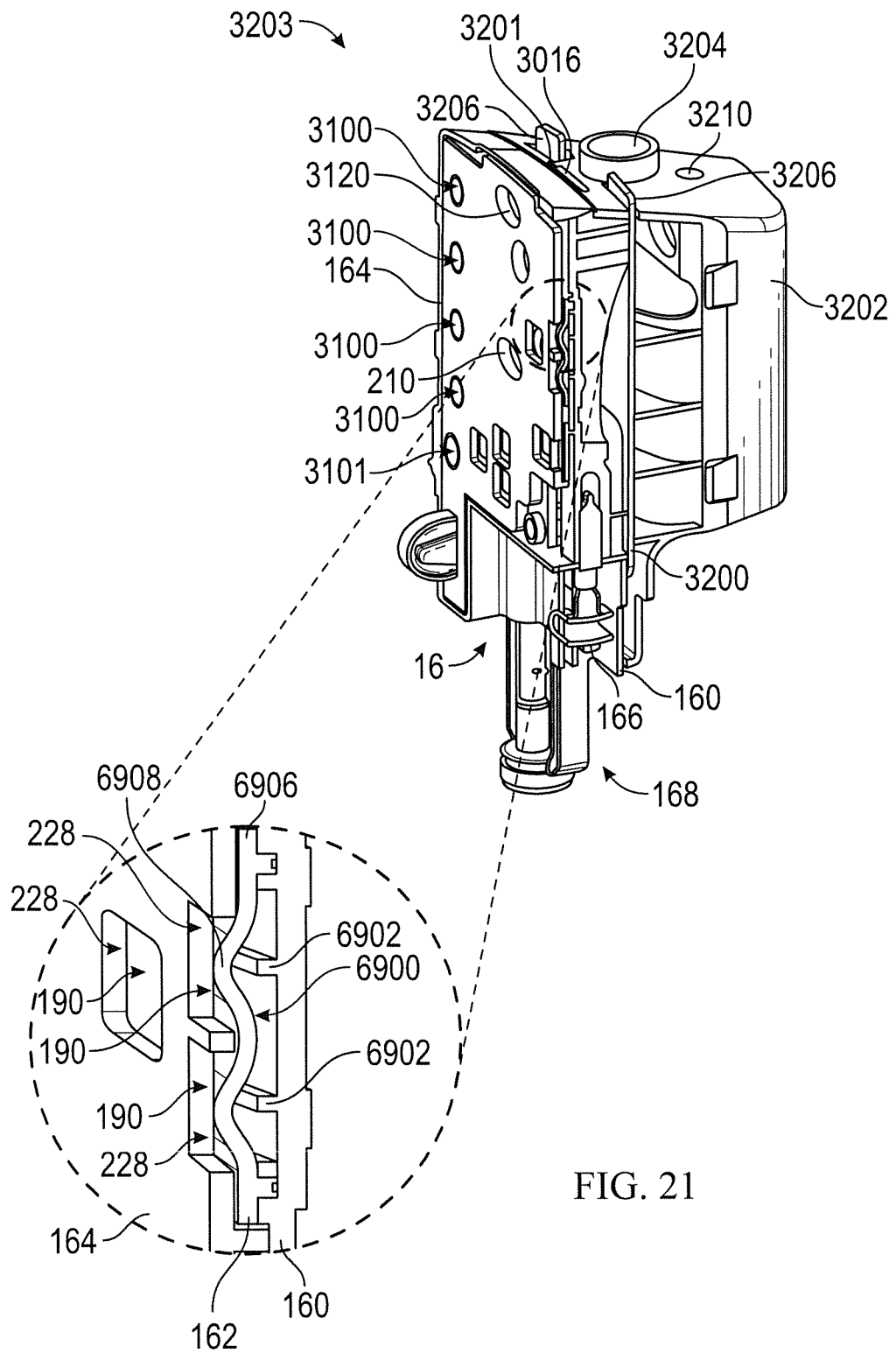
FIG. 21 illustrates a cross-sectional perspective view of the cartridge of FIG. 19 with an attached backpack in accordance with aspects of the present disclosure.

FIG. 21 is a cross-sectional perspective side view of an assembled cartridge 16 having a backpack 3202 (e.g., an implementation of backpack 2900 of FIG. 14) attached thereto to form a cartridge and backpack assembly 3203. As shown in FIG. 21, protrusion 3016 may extend into an opening 3201 in the backpack 3202 to latch the backpack to cartridge 16 at the top side. Additional latching structures at the bottom side will be described in further detail hereinafter. An additional structure 3200 may be disposed between backpack 3202 and cartridge 16. Structure 3200 may be substantially planar and may be shaped and positioned to latch cartridge and backpack assembly 3203 to carousel 14. For example, protrusions 3206 that extend from the top of the backpack 3202 may be actuatable to facilitate installation and removal of the cartridge and backpack assembly into and out of the carousel. For example, ramp structures on the carousel may compress protrusions 3206 when cartridge and backpack assembly 3203 is pushed into the carousel until protrusions 3206 snap up into a locked position to secure the cartridge and backpack assembly in the carousel. To remove cartridge and backpack assembly 3203 from the carousel for compounding operations, a bayonet 128 that extends into opening 210 may be turned to lower protrusions 3206 to release the cartridge and backpack assembly from the carousel. Further features of the coupling of cartridge and backpack assembly 3203 to the carousel will be described hereinafter.

Tubing (e.g., flexible tubing 38) for fluidly coupling cartridge 16 to a receiving container 32 may be housed within backpack 3202. For example, the tubing may be coupled at an output port 180 (e.g., a receiving container port—see, e.g., FIG. 20B) to cartridge 16, coiled within an internal cavity of backpack 3202, and extend through opening 3210 so that an end of the tubing can be pulled by an operator to extend the tubing for coupling to the receiving container. An additional opening 3204 may be provided within which a connector such as a Texium® connector coupled to the end of the tubing can be stored when the cartridge and backpack assembly is not in use. When instructed (e.g., by onscreen instructions on display 86) an operator may remove the connector from opening 3204, pull the tubing from within backpack 3202, and connect to the connector to a receiving container. For example, processing circuitry of the compounder system may provide instructions, using the display, to (a) remove a connector that is coupled to the tubing from an additional opening in the backpack, (b) pull the tubing from the backpack, and (c) connect the connector to the receiving container. In another embodiment, extension of the flexible tubing is automatic (e.g., software determines the precise moment the flexible tube should be extended, the pump head operates screw mechanism to extend the tubing, and a signal to the user to pull the ISO Luer out of the backpack opening is provided). Compounder 10 may include a sensor such as an optical sensor that determines whether the connector is present within opening 3204 (e.g., by viewing the connector through opening 3120).

Compounder 10 may determine, based on whether the connector is within opening 3204, whether and when to release the cartridge and backpack assembly from the pump head assembly. For example, following compounding operations, an operator may be instructed to remove the connector from the receiving container and return the connector into opening 3204. Backpack 3202 may include features and components for facilitating the storage and extraction of the tubing from within the internal cavity. When the connector is detected in opening 3204, the pump drive mechanism 20 may operate one or more coiling mechanisms within backpack 3202 to pull the extended tubing back into the backpack and may turn the bayonet to lower protrusions 3206 so that the cartridge and backpack assembly can be returned to the carousel.

FIG. 21 also shows an enlarged view of a portion of cartridge 16 with the cross-section taken through two of valves 190 within openings 228 in bezel 164. As shown in the enlarged view, each valve 190 may be formed from a raised portion 6908 of sealing membrane 162 that extends from a planar portion 6906 of sealing membrane 162 into a corresponding opening 228 in cartridge bezel 164. In the example shown in, for example, FIGS. 19-21, raised portion 6908 is a pyramid-shaped dome formed in opening 228. In a portion of the fluid path 6900 formed between sealing membrane 162 and frame 160 adjacent each valve 190, frame 160 may include a rib 6902 in spaced opposition to the raised portion 6908 of the sealing membrane for that valve. When raised portion 6908 is in a raised position, fluid and/or vapor can flow over rib 6902 through the open valve. In operation, a valve actuator 84 that extends from and is operable by pump head assembly 28 can extend through opening 228 to compress raised portion 6908 against rib 6902 to close the valve and prevent fluid from flowing therethrough.

Figure 22:
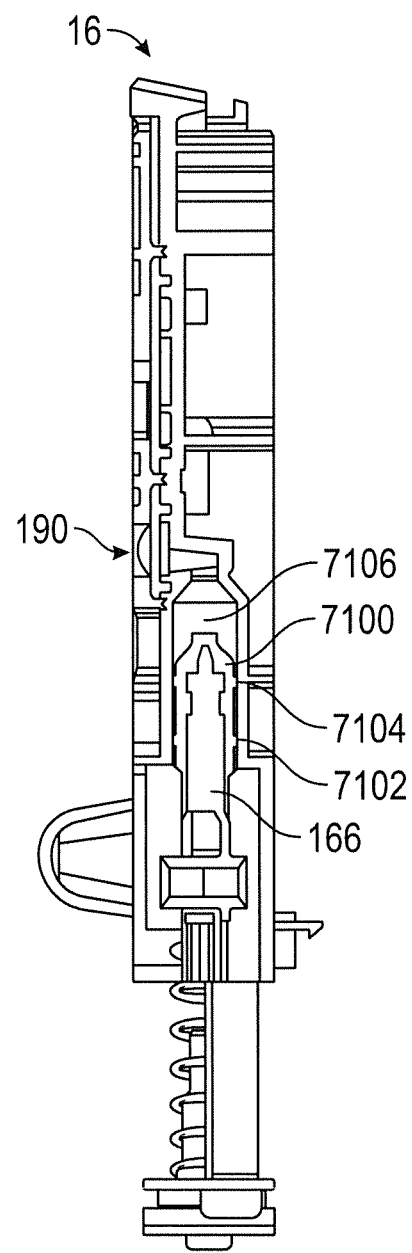
FIG. 22 illustrates a cross-sectional side view of the cartridge of FIG. 19 in accordance with aspects of the present disclosure.

FIG. 22 is a cross-sectional side view of the cartridge showing piston pump 166. As shown in FIG. 22, piston pump 166 may include a silicon boot 7100 having first and second seals 7102 and 7104. Forward seal 7104 may form a moving boundary of a pump chamber 6106. Rearward seal 7102 may prevent dust or other contaminants from contacting forward seal 7104. Pump chamber 7106 may be formed adjacent one or more valves 190 (e.g., a pair of valves may be disposed on opposing sides of the pump chamber to control fluid flow into and out of the pump chamber).

Figure 23:
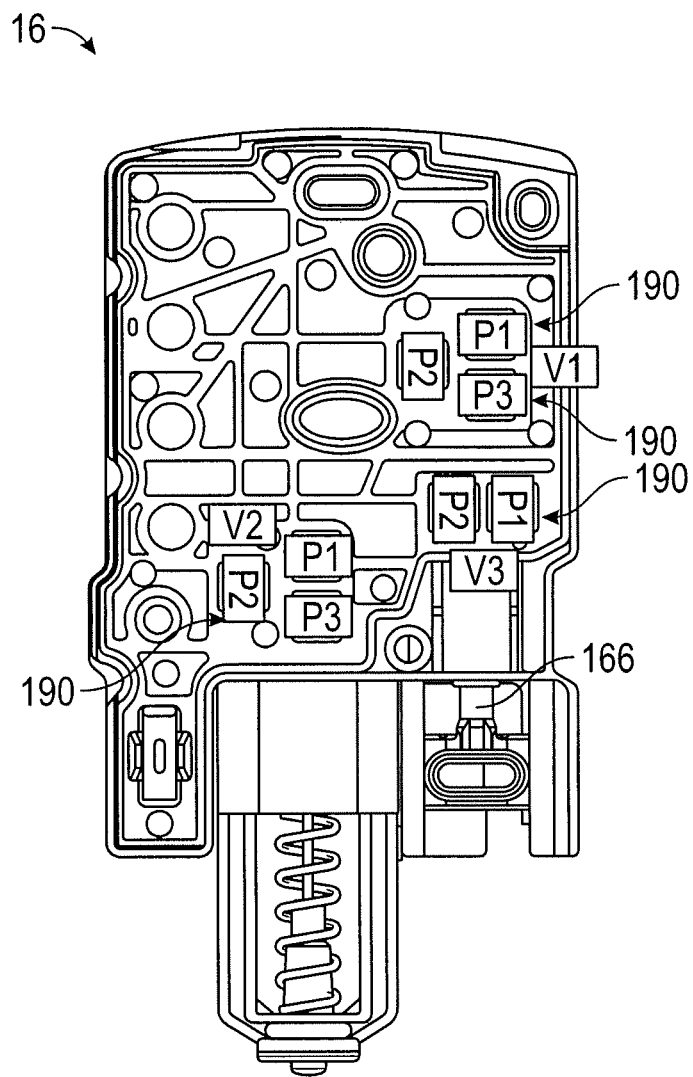
FIG. 23 illustrates the cartridge of FIG. 19 showing the valves and fluid flow paths in accordance with aspects of the present disclosure.

In FIG. 23, for purposes of discussion herein, valves 190 are labeled in three valve groups V1, V2, and V3. Valve group V1 may be a diluent valve group having three valves P1, P2, and P3. Valve group V2 may be a reconstitution valve group having three valves P1, P2, and P3. Piston pump valves P1 and P2 of valve group V3 (e.g., a piston pump valve group) may be operated alternately in cooperation with piston pump 166. For example, during a forward stroke of piston pump 166, valve V3/P1 may be closed and valve V3/P2 may be open and during a backward stroke of piston pump 166, valve V3/P1 may be open and valve V3/P2 may be closed to pump fluid in a first direction within the fluid pathways of cartridge 16. In another example, to pump fluid in an opposite, second direction within the fluid pathways of cartridge 16, during a forward stroke of piston pump 166, valve V3/P1 may be open and valve V3/P2 may be closed and during a backward stroke of piston pump 166, valve V3/P1 may be closed and valve V3/P2 may be open.

Figure 24:
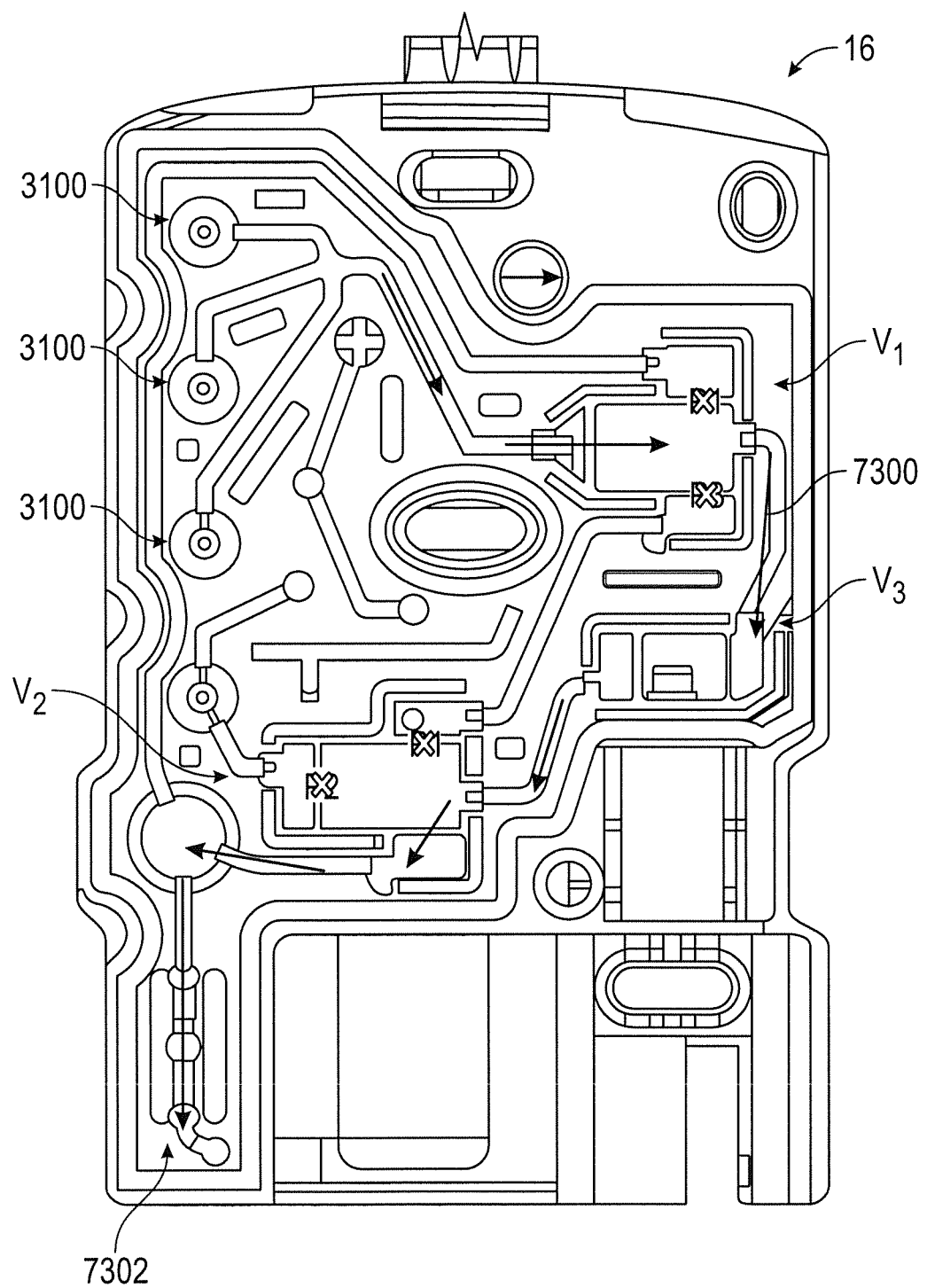
FIG. 24 illustrates the cartridge of FIG. 19 showing a valve configuration for a diluent to receiving container fluid path in accordance with aspects of the present disclosure.

FIGS. 24-27 show various examples of valve configurations for pumping fluids through cartridge 16 for various portions of a compounding operation using the valve labels shown in FIG. 23 for reference. In the example of FIG. 24, the valves of valve groups V1 and V2 are configured for pumping diluent from a diluent container directly to a receiving container (e.g., valves P1 and P3 of group V1 are closed, valve P2 of group V1 is open, valves P1 and P2 of group V2 are closed, and valve P3 of group V2 is open to form a fluid path 7300 from one of diluent ports 3100 to receiving container port 7302).

Figure 25:
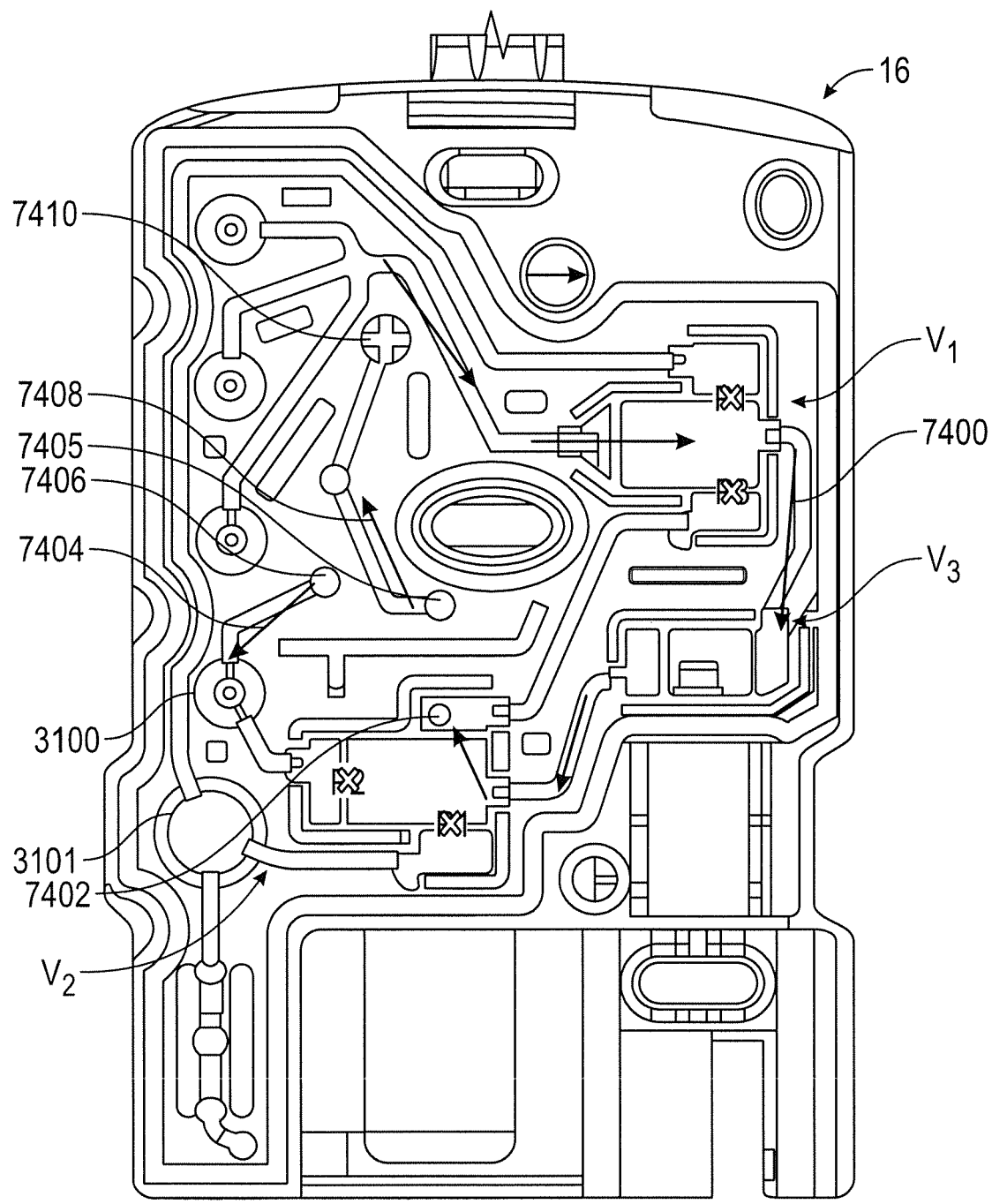
FIG. 25 illustrates the cartridge of FIG. 19 showing a valve configuration for a reconstitution fluid path through in accordance with aspects of the present disclosure.

In the example of FIG. 25, the valves of valve groups V1 and V2 are configured for pumping diluent from a diluent container to a vial for reconstitution operations (e.g., valves P1 and P3 of group V1 are closed, valve P2 of group V1 is open, valves P2 and P3 of group V2 are closed, and valve P1 of group V2 is open to form a fluid path 7400 from one of diluent ports 3100 to vial port 7402). As shown, during reconstitution operations, a hazardous vapor path 7404 may be formed from a vial waste port 7406 to waste port 3100 to be provided to waste container 44. In some embodiments, a non-hazardous waste path 7408 may be provided from a non-hazardous vial waste port 7405 to air filter port 7410. However, this is merely illustrative. In some embodiments, air filter port 7410 may be associated with air filter check valve structures 3004, 3004, and 3006 that prevent flow of any vapor waste along path 7408 and ensure that all vapor waste from vial 18 is moved along path 7404 through waste port 3100.

Figure 26:
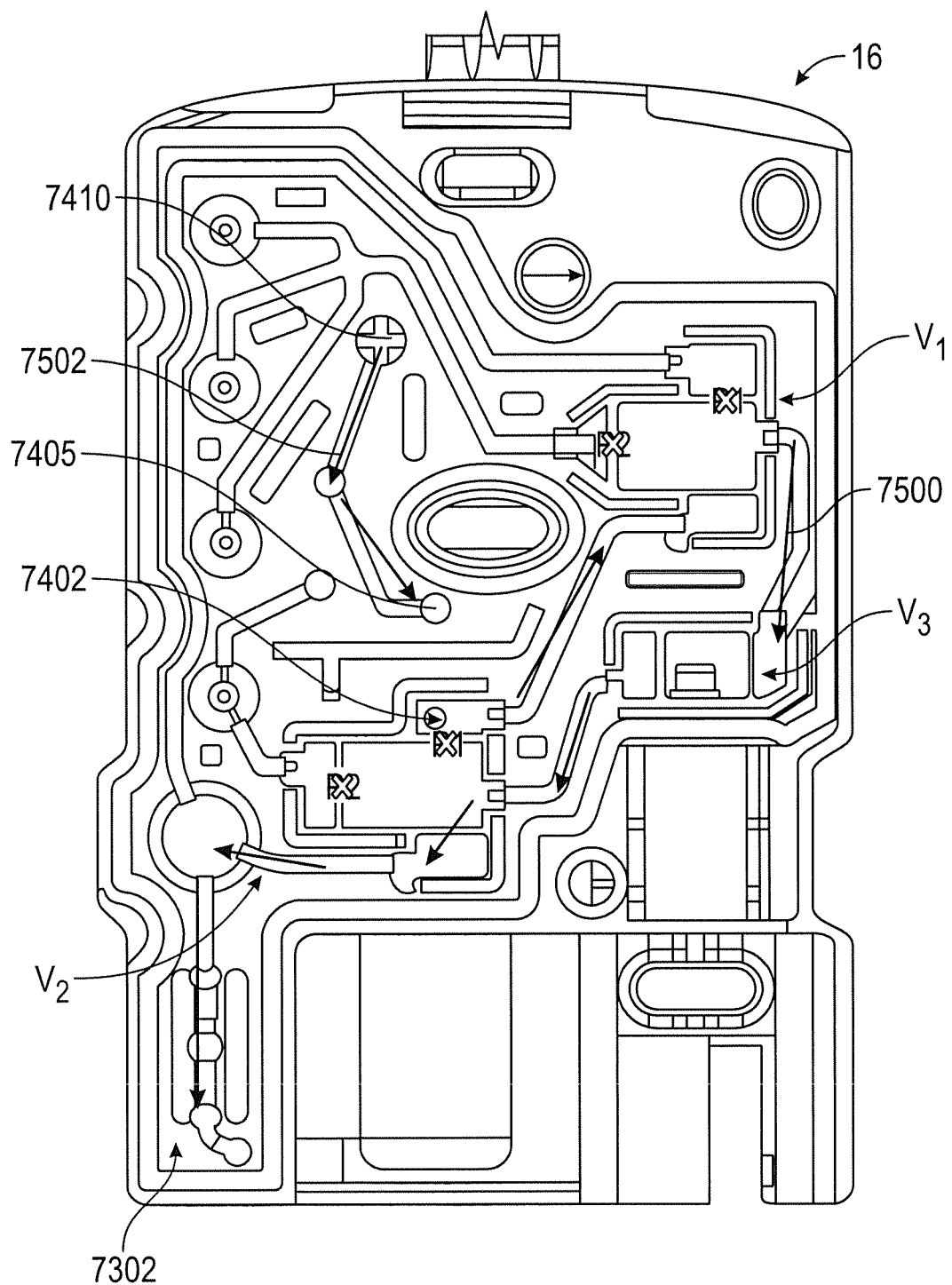
FIG. 26 illustrates the cartridge of FIG. 19 showing a valve configuration for a compounding fluid path from in accordance with aspects of the present disclosure.

In the example of FIG. 26, the valves of valve groups V1 and V2 are configured for pumping a reconstituted drug from a vial to a receiving container for compounding operations (e.g., valves P1 and P2 of group V1 are closed, valve P3 of group V1 is open, valves P1 and P1 of group V2 are closed, and valve P3 of group V2 is open to form a fluid path 7500 from vial port 7402 to receiving container port 7302). As shown, during compounding operations, a path 7502 may be formed from air filter port 7410 to non-hazardous vapor vial port 7405 to provide filtered, sterile air from outside cartridge 16 into the vial to prevent a vacuum from being generated when the drug is pumped from the vial.

Although the receiving container 32 is shown in, for example, FIGS. 1, 3, and 11, as an IV bag, in some scenarios, the receiving container 32 may be implemented as a syringe. For example, a Texium® connector coupled by tubing to an output port such as receiving container port 7302 may be connected to a needle free valve connector such as a SmartSite® connector, the SmartSite® connector being coupled by additional tubing to another needle free valve connector (e.g., another SmartSite® connector) that is connected to a syringe for receiving a reconstituted drug. In scenarios in which the receiving container is a syringe, it may be desirable, after pumping the drug from the vial into the syringe, to remove air or other vapors from the syringe.

Figure 27:
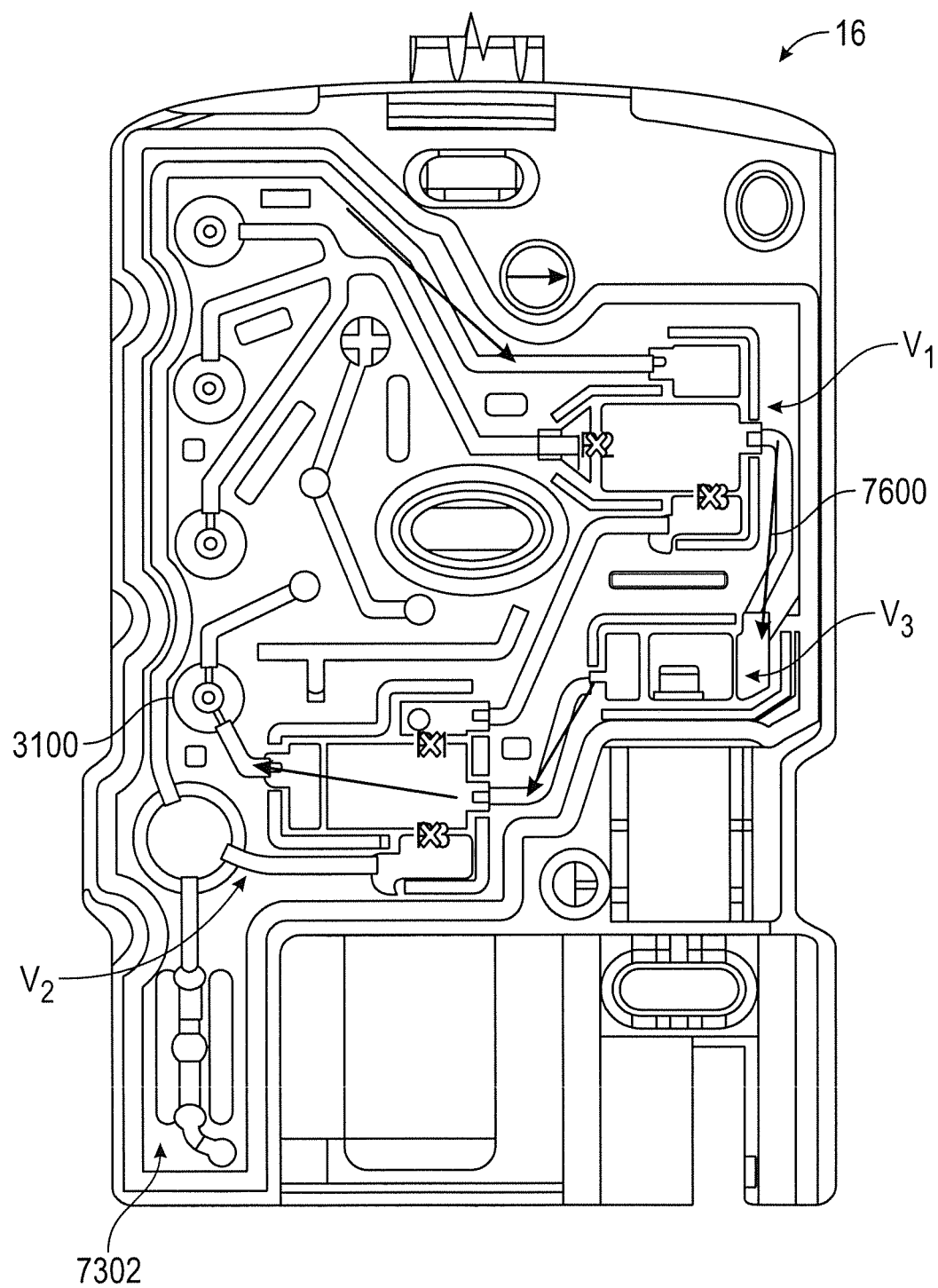
FIG. 27 illustrates the cartridge of FIG. 19 showing a valve configuration for an air removal fluid path in accordance with aspects of the present disclosure.

In the example of FIG. 27, the valves of valve groups V1 and V2 are configured for pumping air from a receiving container such as a syringe (e.g., valves P1 and P3 of group V1 are closed, valve P2 of group V1 is open, valves P2 and P3 of group V2 are closed, and valve P1 of group V2 is open to form a fluid path 7600 from receiving container port 4302 to waste port 3100). In some configurations, the valves P1 and P2 of group V3 may be alternately opened and closed in cooperation with the motion of piston pump 166 to move the desired fluid or vapor along the fluid pathways defined by valves 190.

FIG. 28 is a chart showing the position and operation of the valves 190 as labeled in FIG. 23 during various portions of a reconstitution/compounding process as described above in connection with FIGS. 24-27.

Figure 29A:
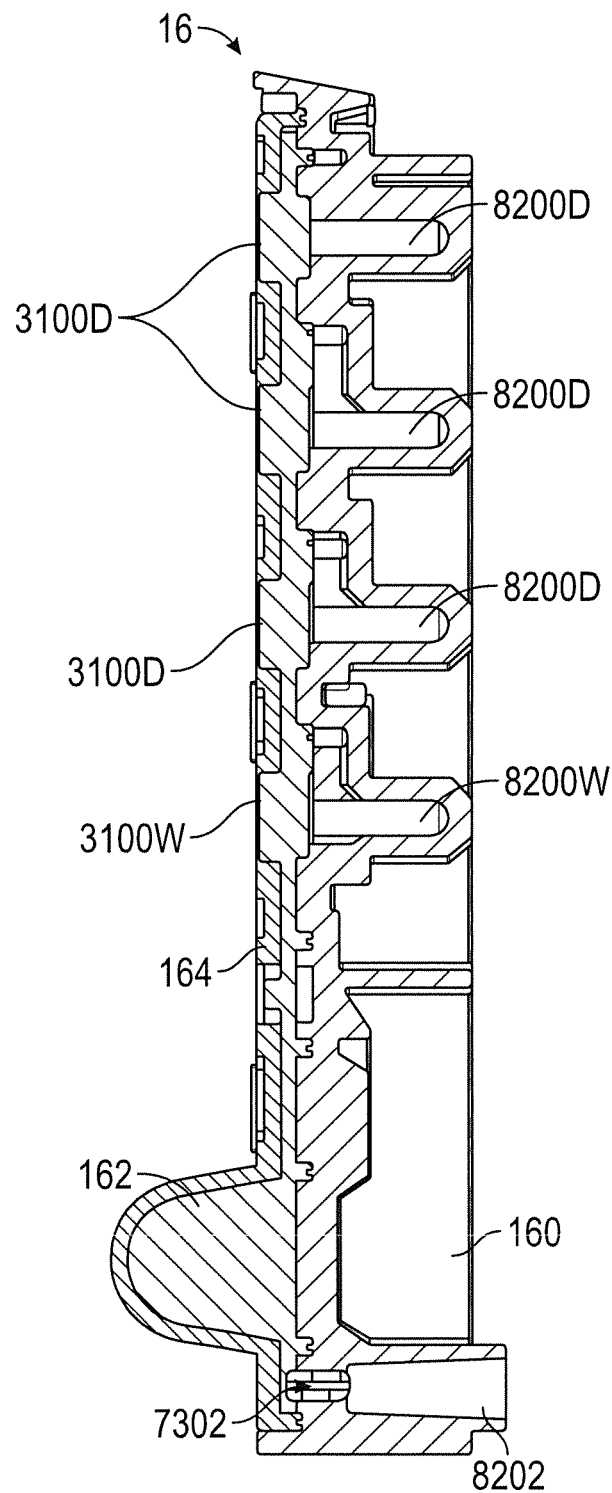
FIG. 29A illustrates a cross-sectional side view of the cartridge of FIG. 19 showing a plurality of ports in accordance with aspects of the present disclosure.

FIG. 29A is a cross-sectional side view of cartridge 16 with the cross section take through diluent ports 3100D, waste port 3100W, and receiving container port 7302. As shown in the example of FIG. 29A, each diluent port 3100D may be formed by a portion of membrane 162 that is formed within an opening in bezel 164 and adjacent to a diluent chamber 8200D. Waste port 3100W may be formed by a portion of membrane 162 that is formed within an opening in bezel 164 and adjacent to a vapor waste chamber 8200W. Receiving container port 7302 may be formed from an opening that leads to a receiving container chamber 8202 in which tubing that extends into backpack 3202 may be disposed to form a fluid path to the receiving container from cartridge 16.

Figure 29C:
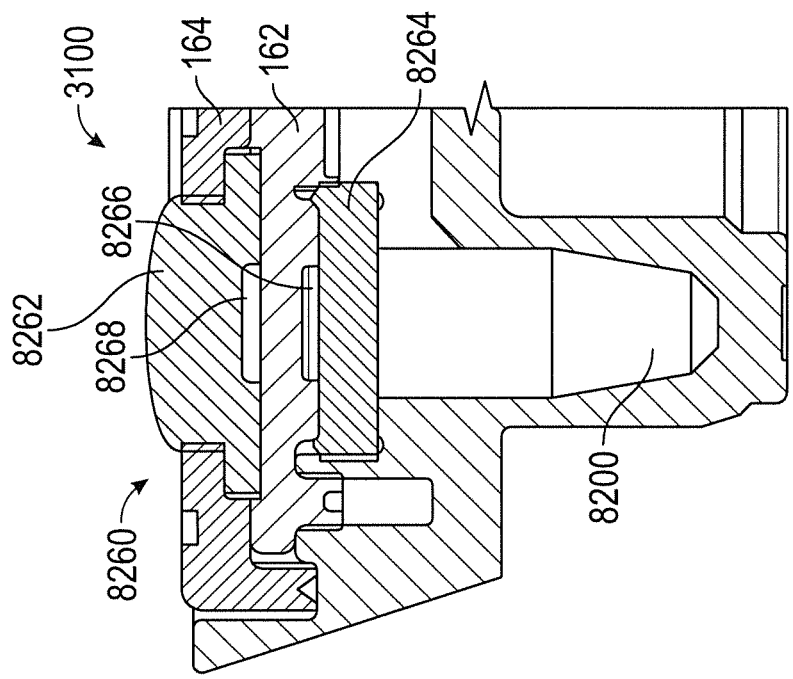
FIG. 29C illustrates a cross-sectional side view of a portion of the cartridge of FIG. 19 showing port seals formed by a plurality of sealing members in accordance with aspects of the present disclosure.
Figure 29B:
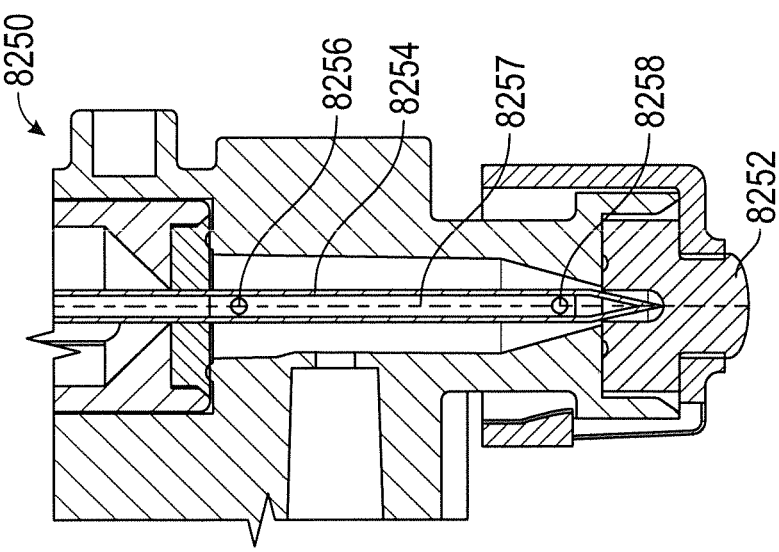
FIG. 29B illustrates a cross-sectional side view of a portion of a diluent manifold having a needle that may interface with one of the ports of FIG. 29A in accordance with aspects of the present disclosure.

When compressed by a sealing manifold membrane such as sealing manifold membrane 8252 of manifold 8250 of FIG. 29B, the portion of sealing membrane 162 that forms diluent and/or waste ports 3100 creates a drip-free connection between the manifold 8250 and the cartridge. A manifold needle 8254 of a selected diluent manifold 8250 and a manifold needle of a waste manifold can extend through the corresponding manifold membrane 8252 and the sealing membrane 162 in the respective diluent and waste port to form fluid paths through sealing membrane 162 (e.g., through opening 8256, central bore 8257, and opening 8258 of needle 8254) for diluents and waste vapors for reconstitution and compounding operations.

However, the example of FIG. 29A, in which the seal of ports 3100D and 3100W are formed solely by a portion of membrane 162 that extends into an opening in bezel 164 is merely illustrative. In some embodiments, in order to provide an improved drip-free seal, the seal of each of ports 3100D and port 3100W may be formed by a plurality of sealing members. In one example, three sealing members may be provided to form a port seal for cartridge 16.

FIG. 29C shows a cross-sectional view of a port of cartridge 16 in an implementation with three sealing members. As shown in FIG. 29C, a port 3100 (e.g., one of diluent port 3100D or waste port 3100W) may be formed from a portion of membrane 162 that is disposed between an outer sealing member 8262 (formed in an opening 8260 in bezel 164) and an inner sealing member 8264. Inner sealing member 8264 may be disposed between membrane 162 and chamber 8200.

As shown in FIG. 29C, outer sealing member 8262 may include a portion that extends through opening 8260 and may also include a recess 8268 on an interior surface adjacent to membrane 162. Membrane 162 may also include a recess 8266 on an interior surface adjacent to inner sealing member 8264. Providing a port 3100 with multiple sealing members such as the three sealing members (i.e., member 8262, member 8264, and the portion of membrane 162 formed between members 8262 and 8264) may provide an enhanced wiping of needle 8254 to provide an improved dry disconnect in comparison with implementations with a single sealing member. However, this is merely illustrative. In various embodiments, one, two, three, or more than three sealing members for each port may be provided. Similarly, interstitial spaces formed from recesses 8266 and 8268 may further increase the efficiency of the wiping of needle 8254, however, in various embodiments, sealing members may be provided with or without recesses 8266 and/or 8268.

Figure 29D:
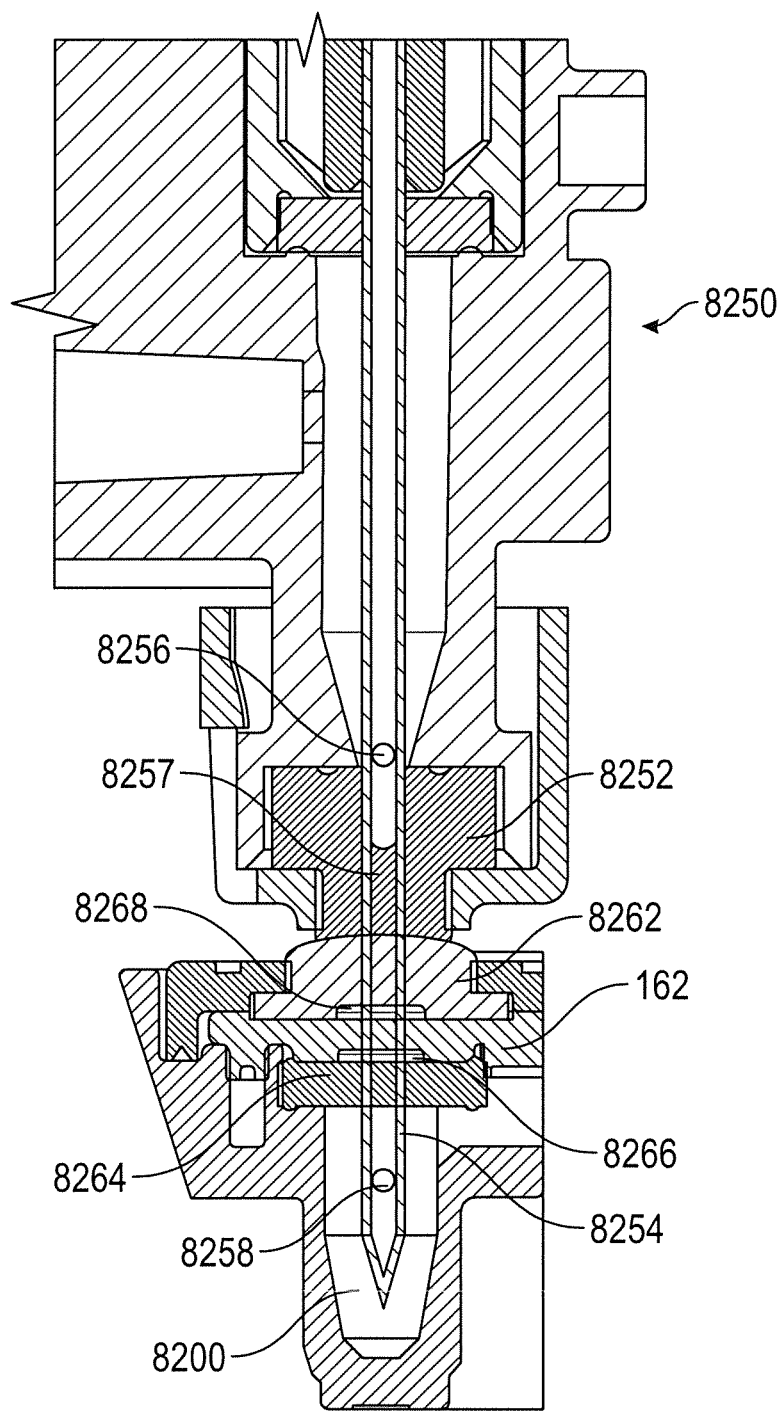
FIG. 29D illustrates a cross-sectional side view of the portion of the manifold of FIG. 29B compressed against the portion of the cartridge of FIG. 29C in accordance with aspects of the present disclosure.

FIG. 29D shows the manifold 8250 of FIG. 82B with manifold sealing member 8252 compressed against outer sealing member 8262 of port 3100 of FIG. 82C. As shown in FIG. 29D, needle 8254 is extended from manifold 8250 through sealing members 8252 and 8262, through interstitial space 8268, through membrane 162, through interstitial space 8266, and through inner sealing member 8264 such that openings 8256 and 8258 and central bore 8257 form a fluid pathway between cartridge 16 and manifold 8250.

In the example of FIG. 29A, the portion of membrane 162 that extends into the openings in bezel 164 in ports 3100 may be compressed (e.g., compressed by 10% radially) to cause a wiping effect on the diluent needles that are extended therethrough and withdrawn therefrom so that when the diluent needles are retracted into the manifold, no liquid is left on the diluent needle or one the outer surfaces of the cartridge or the membrane.

In the example of FIGS. 29C and 29D, the portion of sealing member 8262 that extends into the openings in bezel 164 in ports 3100 may be compressed (e.g., compressed by 10% radially) to cause a wiping effect on the diluent needles that are extended therethrough and withdrawn therefrom so that when the diluent needles are retracted into the manifold, no liquid is left on the diluent needle or one the outer surfaces of the cartridge or the membrane. The multiple sealing members of FIGS. 29C and 29D may be arranged to each provide a wiping effect on needle 8254 that complements the wiping effect of the other sealing members (e.g., by providing, with each member, a peak wiping force on the needle at locations angularly spaced with respect to the peak wiping force of other members).

Figure 30:
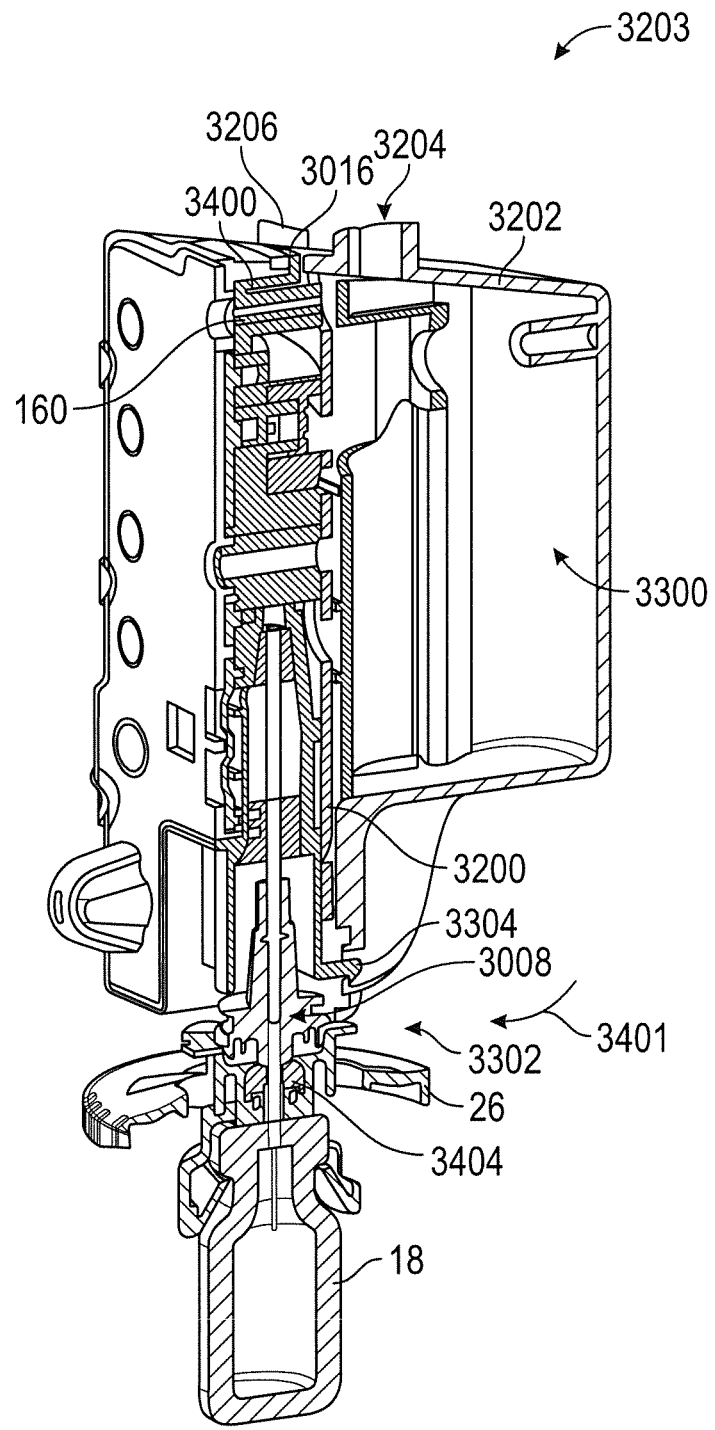
FIG. 30 illustrates a cross-sectional perspective view of the cartridge disposed adjacent a vial in accordance with aspects of the present disclosure.

FIG. 30 is cross-sectional perspective side view of cartridge and backpack assembly 3203 in which protrusion 3016 and protrusion 3304 of cartridge frame 160 can be seen cooperating to couple cartridge 16 to backpack 3202 to form cartridge and backpack assembly 3203. To install backpack 3202 onto cartridge 16, opening 3201 of backpack 3202 can be positioned over protrusion 3016 and backpack 3202 can be rotated (e.g., in a direction 3401) to push latching features 3302 of backpack 3202 against latching protrusion 3304 until latching protrusion 3304 snaps into position between latching features 3302. As shown, protrusion 3016 may be formed on an additional latching structure of cartridge 16 such as a flexible arm 3400. Flexible arm 3400 may allow backpack 3202 to be pulled downward by a small distance when backpack 3202 is rotated to press latching feature 3302 onto protrusion 3304. Flexible arm 3400 may be resilient to maintain an upward force the holds latching features 3302 in a latched position against protrusion 3304.

In the example of FIG. 30, a vial 18 and vial puck 26 are positioned adjacent to cartridge and backpack assembly 3203 with needle assembly 170 extended into the vial through sealing member 3402 of cartridge 16 and sealing member 3404 of vial puck 26 which may provide a drip free seal and allow fluid to be provided into and/or removed from vial 18. Sealing member 3402 may be, for example, an implementation of sealing member 3008. As shown, when the needle assembly 170 is extended into the vial, portions of the vial puck 26 may be located adjacent to latching features 3302 of backpack 3202.

Figure 31:
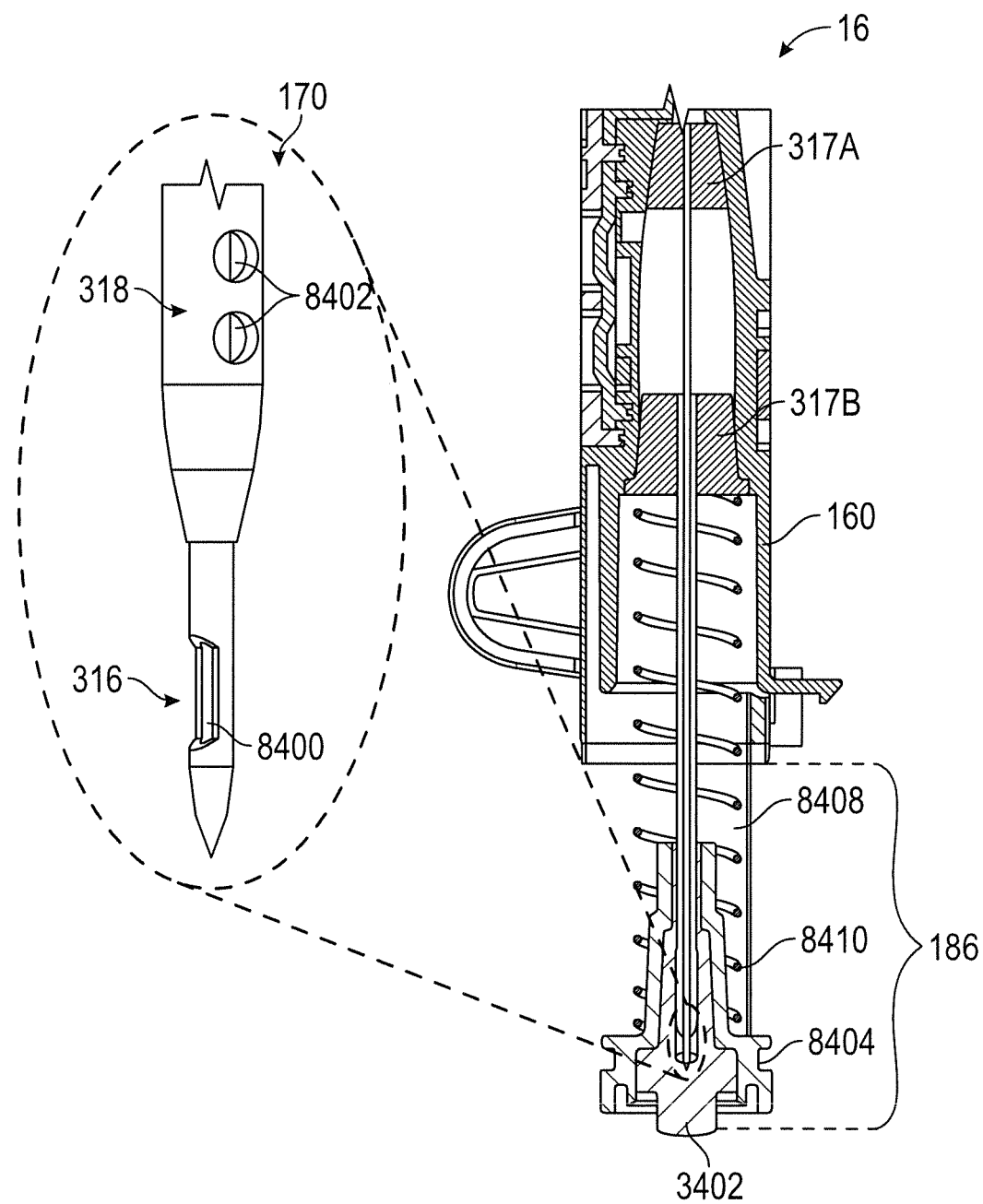
FIG. 31 illustrates a cross-sectional side view of a portion of the cartridge of FIG. 19 in the vicinity of a dual lumen needle in accordance with aspects of the present disclosure.

FIG. 31 shows a cross-sectional view of a portion of cartridge 16 along with an enlarged view of a portion of needle assembly 170. As shown in FIG. 31, needle housing 186 may include a sealing membrane 3402 formed within an annular housing member 8404 that is attached to cartridge frame 160 via one or more housing arms 8408. A spring 8410 may be provided that extends from needle housing 317B into needle housing 186 such that compression of spring 8410 is necessary to extend needles 316 and 318 through sealing membrane 3402. In this way, a user handling cartridge 16 is prevented from being injured by access to needle assembly 170. In operation, a vial puck may be pressed against annular housing member 8404 to compress spring 8410 such that needle assembly 170 extends through sealing membrane 3402 and through a sealing membrane of the vial puck into the vial.

Dual lumen needles 316 and 318 may be respectively provided with openings 8400 and 8402 that provide fluid access to central bores of the needles. Needle 316 may, for example, be a 24 gauge needle held in cartridge frame 160 by a high density polyethylene (HDPE) overmold 317A, the needle having an opening 8400 for venting the drug vial. Opening 8400 may be formed using a slot cut as shown to reduce coring of the sealing membranes as the needle is inserted and retracted. Needle 318 may, for example, be an 18 gauge needle held in cartridge frame by a high density polyethylene (HDPE) overmold 317B with one or more openings 8402 for fluid flow into and/or out of the vial. Openings 8402 may include two drilled holes configured to reduce coring and to allow up to, for example, 60 mL/min of fluid flow.

In this way, during reconstitution operations, diluent may be provided into the vial via openings 8402 of needle 318 and vapor waste may be simultaneously extracted from the vial via opening 8400 in needle 316. During compounding operations, a reconstituted drug may be pulled from the vial via openings 8402 of needle 318 and sterile air may be provided into the vial via opening 8400 of needle 316.

Although various implementations of cartridge 16 have been described in which a a linearly oscillating piston pump (see, e.g., piston 166 of FIG. 21) is operated, in combination with finger-operated valves to move and direct fluid and/or gasses through cartridge 16 and from diluent containers and to a receiving container, in other implementations, one or more rotary piston pump/valves may be used to move fluid and/or gasses through the various fluid flow pathways of cartridge 16. For example, cartridge 16 may be provided with a dedicated rotary piston pump/valve for each process (e.g., reconstitution, compounding, etc.) of compounder 10 that moves fluid and/or gas through cartridge 16.

Implementations of cartridge 16 having rotary piston pump/valves may reduce component costs and complexity for cartridge 16, since the same device can be used both as a pump and as a shutoff valve. For example, in a rotary piston pump/valve, when turning, the rotary piston pump/valve acts as a pump and when the rotary piston pump/valve stops turning, it effectively acts as a shutoff valve, preventing any fluid flow. A cartridge implemented with rotary piston pump/valves may also use reduced power to turn a motor (e.g., a simple stepper or direct-current motor) for the rotary piston pump/valves, in comparison with other implementations. Implementations of cartridge 16 having rotary piston pump/valves may provide other benefits include preventing diluent lines from being exposed to pressure and preventing waste lines from being exposed to a vacuum.

FIG. 32 shows an illustrative implementation of a rotary piston pump/valve. As shown in FIG. 32, rotary pump/valve 13200 includes a housing 13201 within which a rotary piston 13204 is disposed. Rotary piston 13204 includes a cavity 13206 and is coupled to a gear 13202. Gear 13202 may interface with a corresponding gear of the pump head assembly for rotation, by the pump head assembly, to rotate the gear and thereby rotate cavity 13206. Gear 13202 may have a cam surface. Housing 13201 may include an input port 13208 and an output port 13210.

As shown in FIG. 32, when gear 13202 and rotary piston 13204 are rotating, and positioned such that cavity 13206 is adjacent input port 13208, fluid (e.g., diluent, waste fluid, or reconstituted drug) is drawn into cavity 13206 by cam action on gear 13202 that causes piston 13204 and cavity 13206 to actuate downward during an intake stroke. As shown in FIG. 33, following the intake stroke, gear 13202 and rotary piston 13204 are rotated, with fluid disposed within cavity 13206, to a transition position in which cavity 13206 is rotationally between input port 13208 and output port 13210. As shown in FIG. 34, following the transition, gear 13202 and rotary piston 13204 are rotated, with fluid disposed within cavity 13206, to a position in which cavity 13206 is rotationally aligned with output port 13210 so that fluid within cavity 13206 is ejected through output port 13210, by cam action on gear 13202 that causes piston 13204 and cavity 13206 to actuate upward in an ejection stroke.

Figure 35:
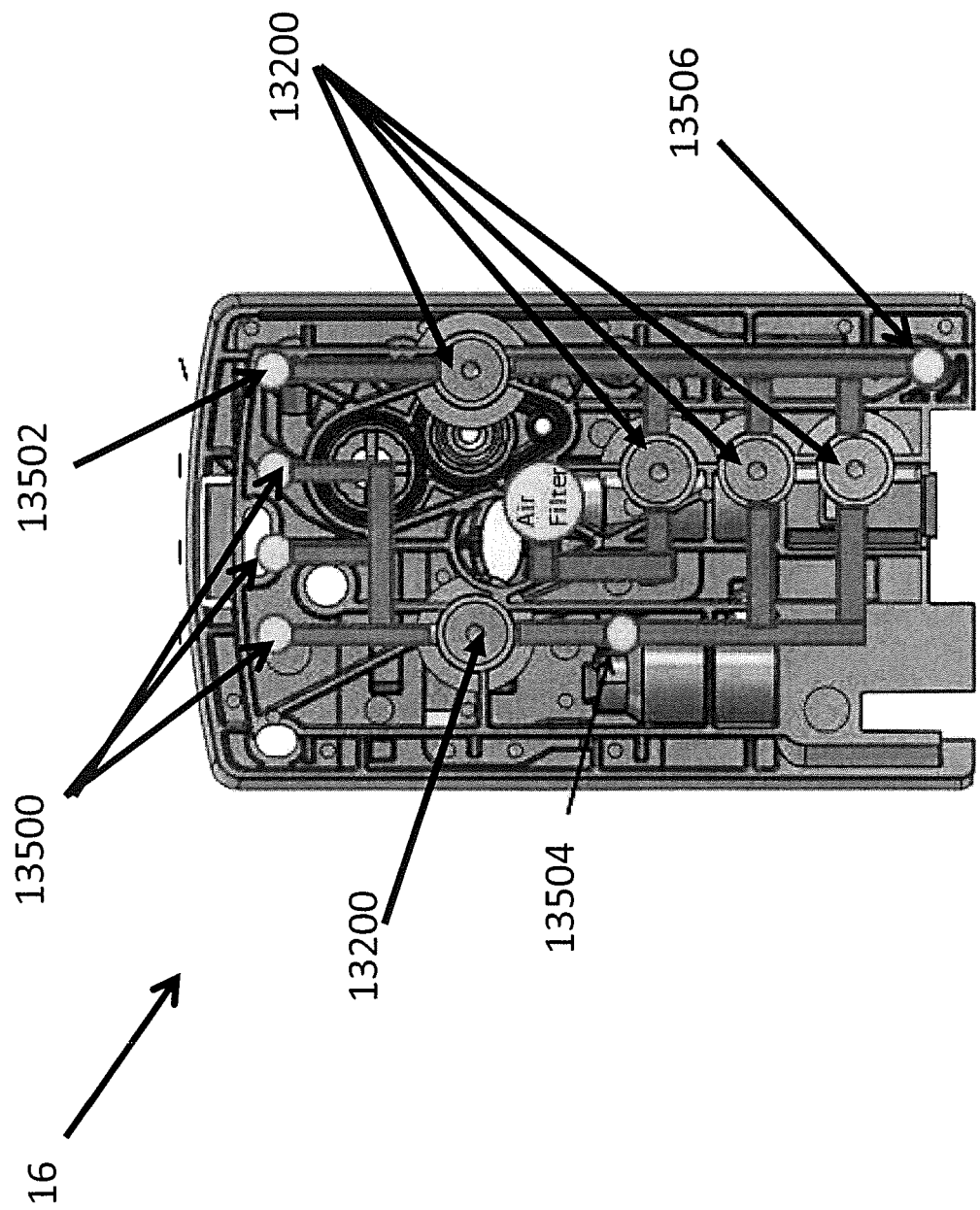
FIG. 35 illustrates a face-on view of a compounder cartridge having rotary piston pump/valves in accordance with aspects of the present disclosure.

FIG. 35 shows a face-on view of cartridge 16, in an implementation in which the cartridge is provided with a series of rotary piston pump/valves 13200 that are actuated by the compounder. As shown in FIG. 35, cartridge 16 may include as many as, or more than, five rotary piston pump/valves 13200, each disposed within an associated fluid pathway of cartridge 16 to move, or prevent movement of, fluid through that associated fluid pathway. Rotary piston pump/valves 13200 may be operated individually, or in combination, to move fluid from one or more of diluent ports 13500 to output port 13506, from a syringe input/output port 13504 to or from output port 13506, from output port 13506 or syringe input/output port 13504 to waste port 13502, from output port 13506 to an air filter, and/or between any other ports of cartridge 16 as desired for compounder operations.

As described above in connection with FIGS. 32-34, as each rotary piston pump/valve 13200 in cartridge 16 turns, there is a translation movement of the piston in the downward direction that pulls fluid into the rotary piston pump/valve 13200 from a portion of an associated fluid pathway in cartridge 16. As the rotary piston continues to turn, cam action forces the piston up and forces the fluid in the chamber thru the output port to another portion of the associated fluid pathway in cartridge 16. This rotary piston pump/valve is unique in that, when the rotary motion stops, it prevents fluid flow through the rotary piston pump/valve which then effectively acts as a shutoff valve.

Figure 36:
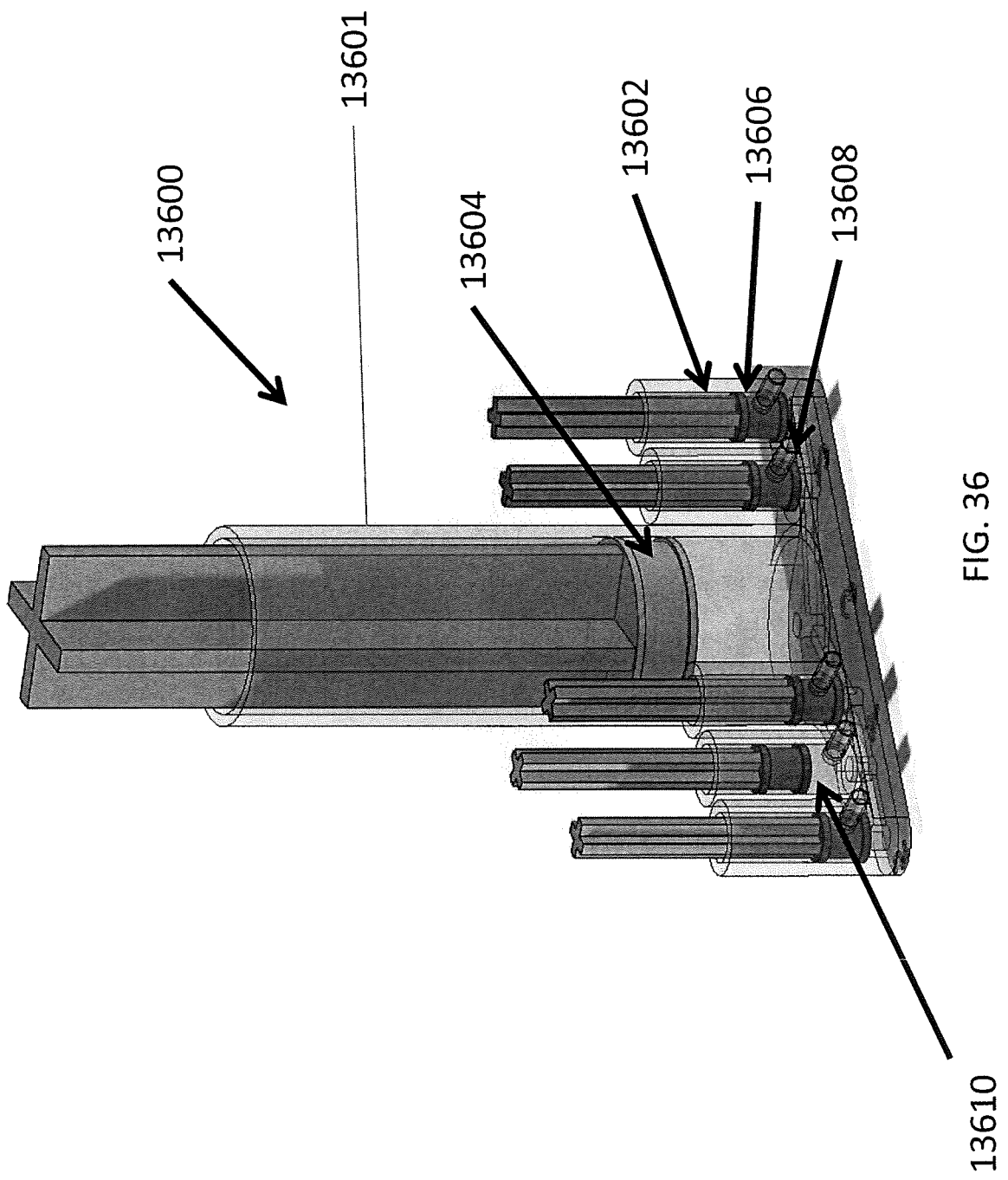
FIG. 36 illustrates a perspective view of a syringe pump/syringe valve apparatus in accordance with aspects of the present disclosure.

In some implementations, instead of (or in addition to) a linearly oscillating piston pump with finger valves and/or a rotary piston pump as described above, cartridge 16 may be provided with a syringe pump with syringe valves. FIG. 36 shows an example of a syringe pump/syringe valve apparatus that may be provided to control movement of fluid and/or gasses through cartridge 16. As shown in FIG. 36, syringe pump/syringe valve apparatus 13600 may include housing 13601 for syringe pump 13604 and multiple syringe valves 13602. Syringe pump 13604 may be actuated by the pump head assembly to push or pull fluid through apparatus 13600. The direction and input and output locations of the flow of fluid through apparatus 13600 may be controlled by the positioning of one or more of syringe valves 13602. A plunger 13606 of each of syringe valves 13602 can be raised or lowered to open or close a corresponding port 13608. In the example of FIG. 36, four of five syringe valves 13602 are closed and one syringe valve plunger is raised to create a cavity 13610 that forms a pathway to a corresponding port 13608.

Figure 37:
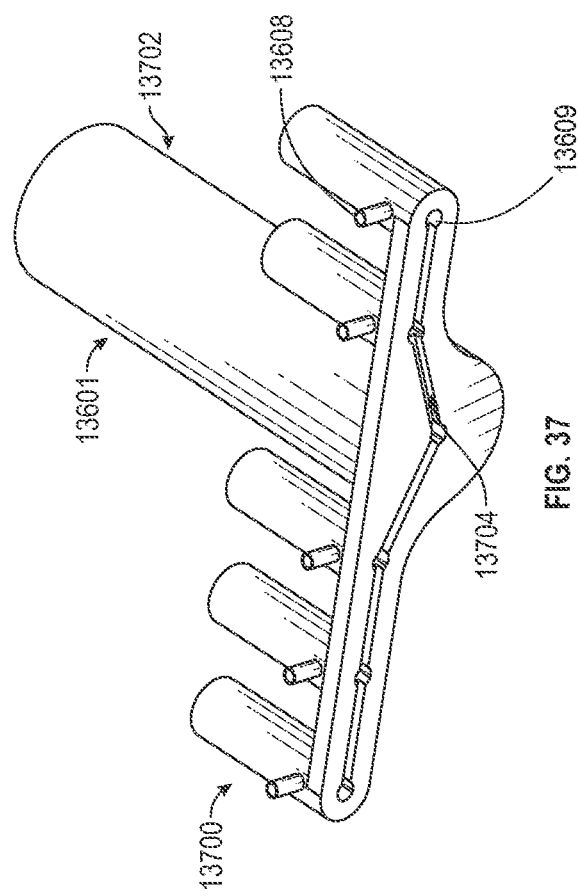
FIG. 37 illustrates a perspective view of a housing for a syringe pump/syringe valve apparatus in accordance with aspects of the present disclosure.
Figure 38:
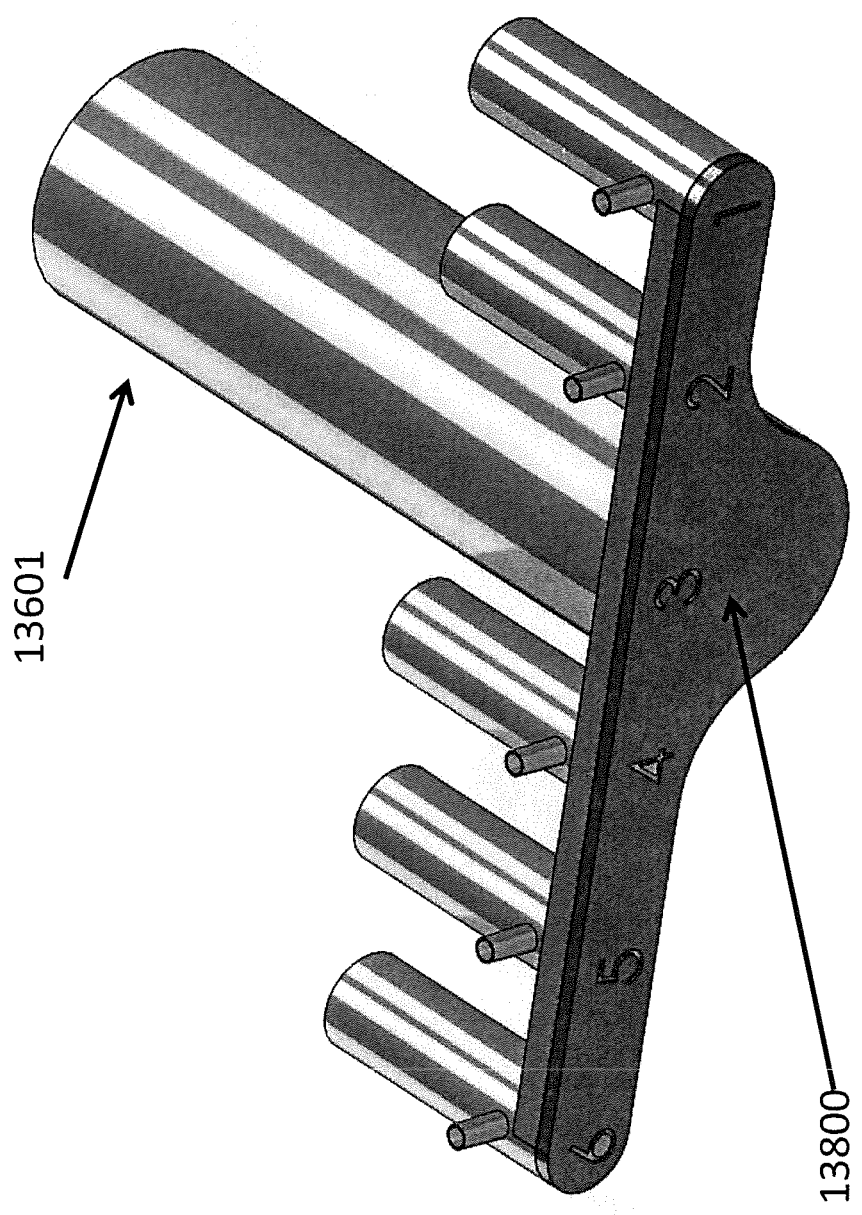
FIG. 38 illustrates a perspective view of a housing and a base plate for a syringe pump/syringe valve apparatus in accordance with aspects of the present disclosure.

FIG. 37 shows a perspective view of housing 13601 in which a flow passage 13704 between a main cylinder 13702 for syringe pump 13604 and a plurality of valve cylinders 13700 can be seen. As shown in FIG. 38, a bottom or base plate 13800 can be attached (e.g., welded) to housing 13601 to enclose fluid passages (e.g., fluid pathway 13704) within the housing.

Figure 40:
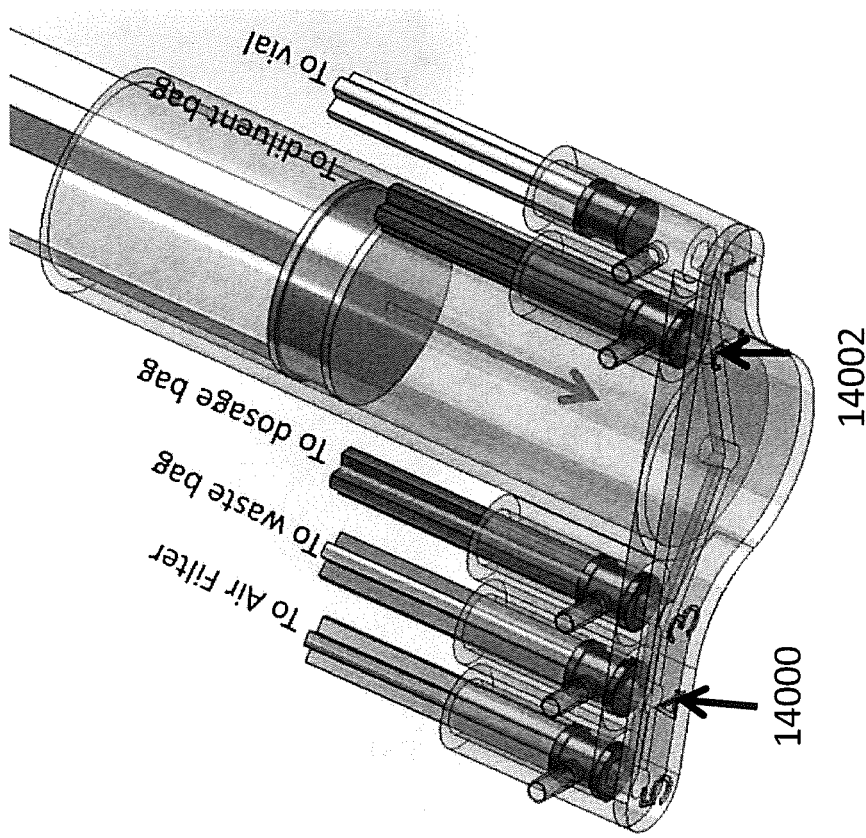
FIGS. 39 and 40 illustrate configurations of a syringe pump/syringe valve apparatus during a reconstitution operation in accordance with aspects of the present disclosure.
Figure 39:
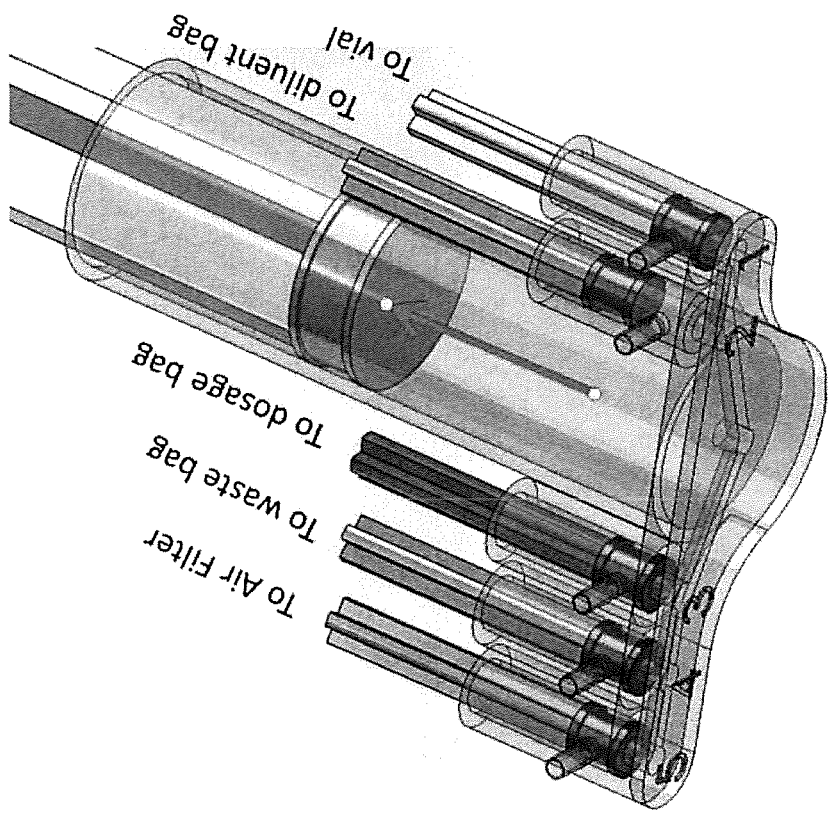

FIGS. 39-46 show various configurations of syringe valves 13602 and motions of syringe pump 13604 for various operations of compounder 10. The examples of FIGS. 39 and 40 show valve and piston operations for reconstitution operations. In the example of FIG. 39, a plunger of syringe piston 13604 is being raised while a syringe valve 13602 coupled to a diluent bag is open, to draw diluent into the syringe piston. In the example of FIG. 40, the syringe valve 13602 coupled to the diluent bag is closed, a syringe valve 13602 coupled to vial 18 is open, and the plunger of syringe piston 13604 is being lowered to push the diluent therein to the vial. As indicated in FIG. 40, apparatus 13600 may include redundant check valves 14000 and 14002 to prevent unwanted flow (e.g., from a waste container or to a diluent bag).

Figure 42:
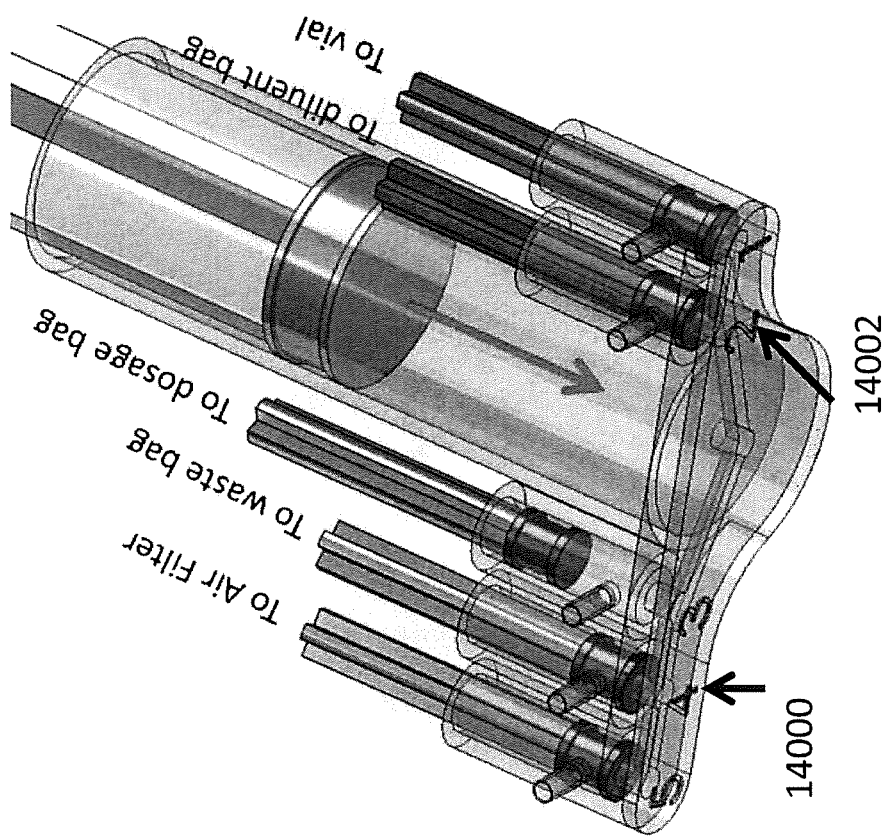
FIGS. 41 and 42 illustrate configurations of a syringe pump/syringe valve apparatus during a compounding operation in accordance with aspects of the present disclosure.
Figure 41:
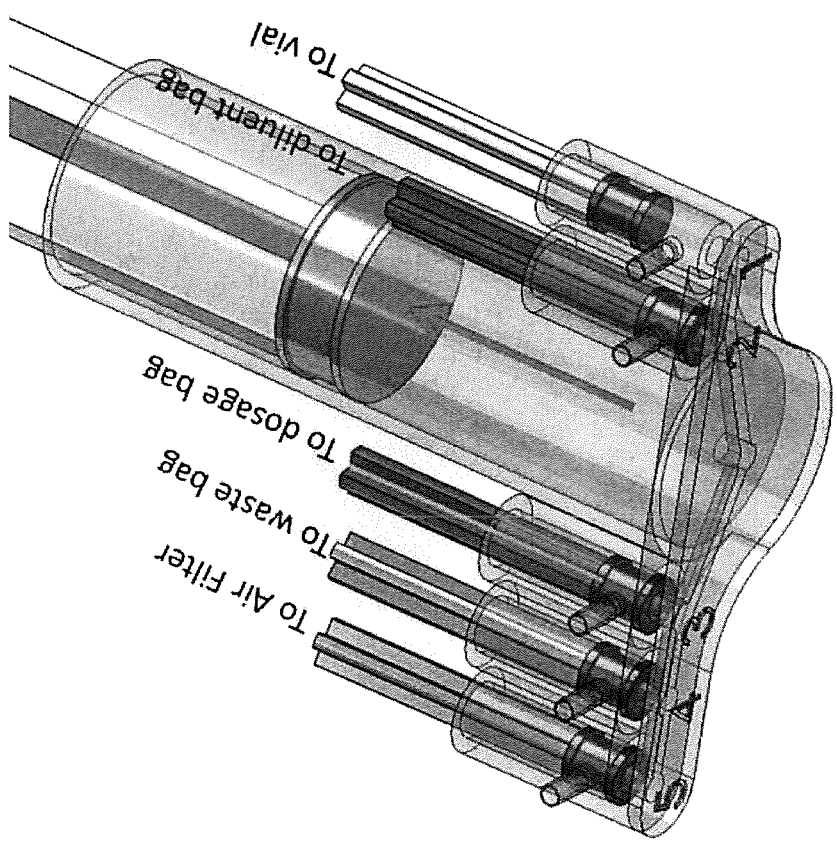

The examples of FIGS. 41 and 42 show valve and piston operations for compounding operations. In the example of FIG. 41, the plunger of syringe piston 13604 is being raised while a syringe valve 13602 coupled to vial 18 is open, to draw reconstituted drug into the syringe piston from the vial. In the example of FIG. 42, the syringe valve 13602 coupled to vial 18 is closed, a syringe valve 13602 coupled to receiving container 32 (e.g., a dosage bag) is open, and the plunger of syringe piston 13604 is being lowered to push the reconstituted drug therein to the receiving container.

Figure 44:
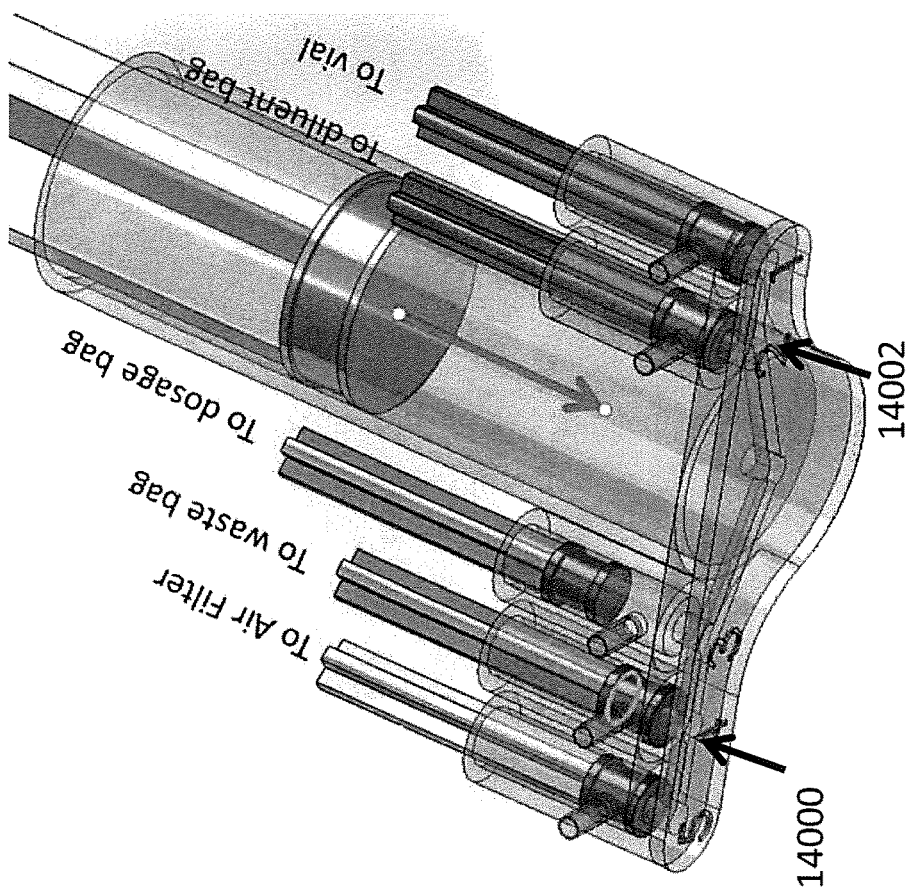
FIGS. 43 and 44 illustrate configurations of a syringe pump/syringe valve apparatus during an air purge operation in accordance with aspects of the present disclosure.
Figure 43:
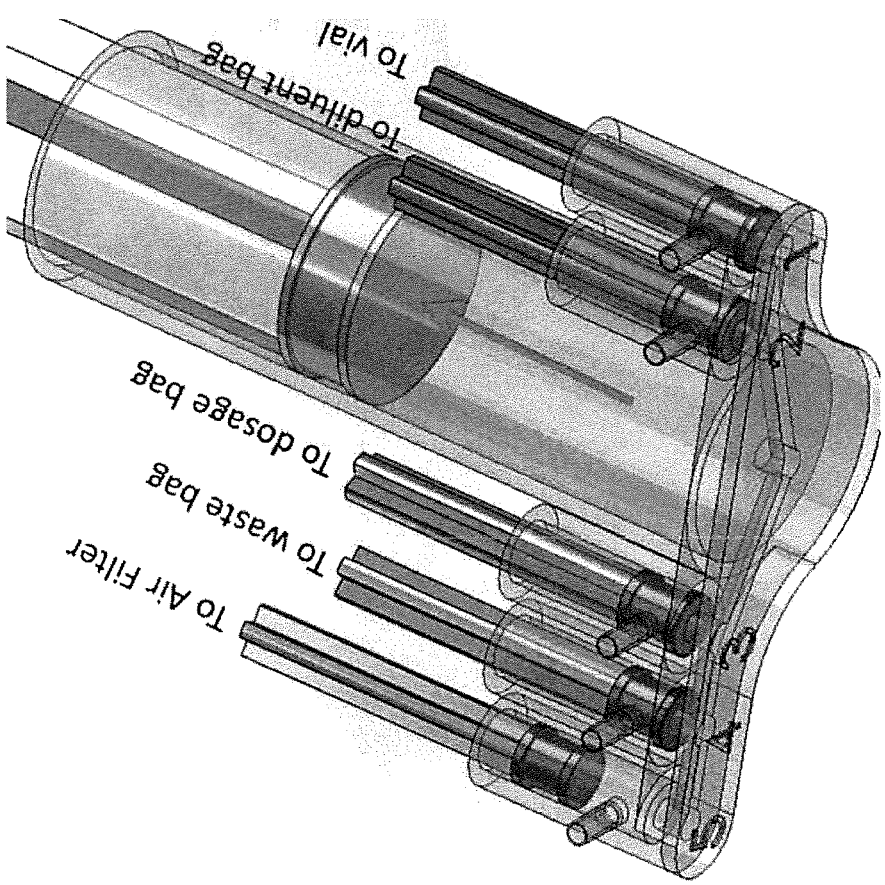

The examples of FIGS. 43 and 44 show valve and piston operations for air purge operations. In the example of FIG. 43, the plunger of syringe piston 13604 is being raised while a syringe valve 13602 coupled to an air filter (e.g., an air filter between an ambient air port and apparatus 13600) is open, to draw filtered air into the syringe piston from ambient. In the example of FIG. 44, the syringe valve 13602 coupled to the air filter is closed, a syringe valve 13602 coupled to receiving container 32 (e.g., a dosage bag) is open, and the plunger of syringe piston 13604 is being lowered to push the filtered air therein to the receiving container (e.g., via tubing such as "pigtail" tubing between cartridge 16 and the receiving container).

Figure 46:
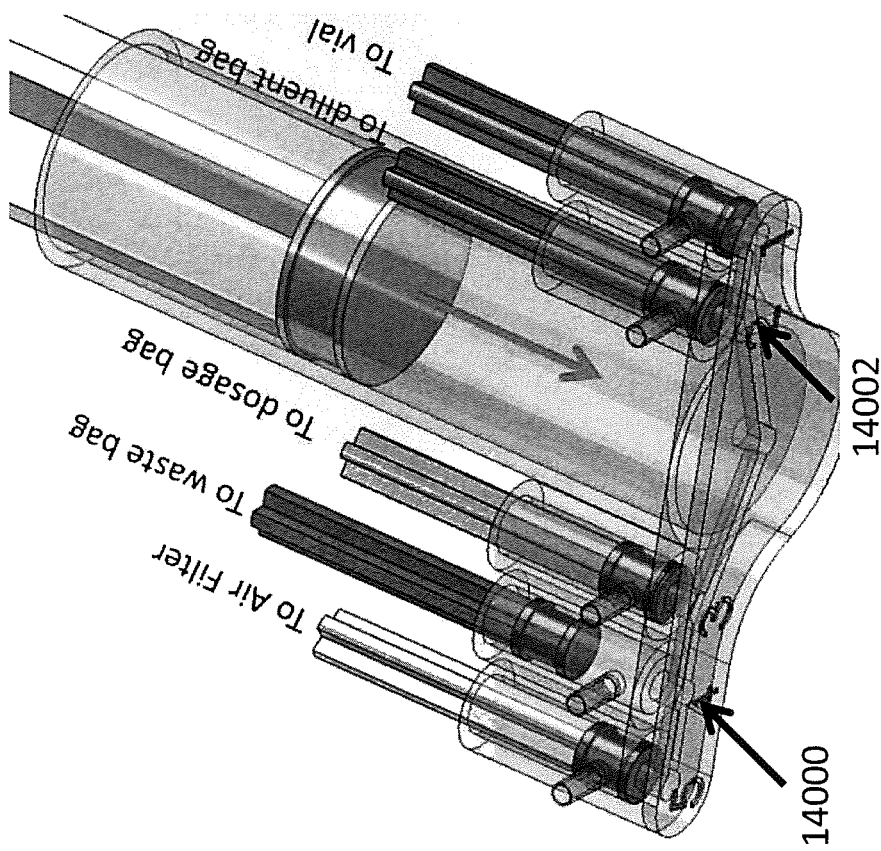
FIGS. 45 and 46 illustrate configurations of a syringe pump/syringe valve apparatus during a waste gas removal operation in accordance with aspects of the present disclosure.
Figure 45:
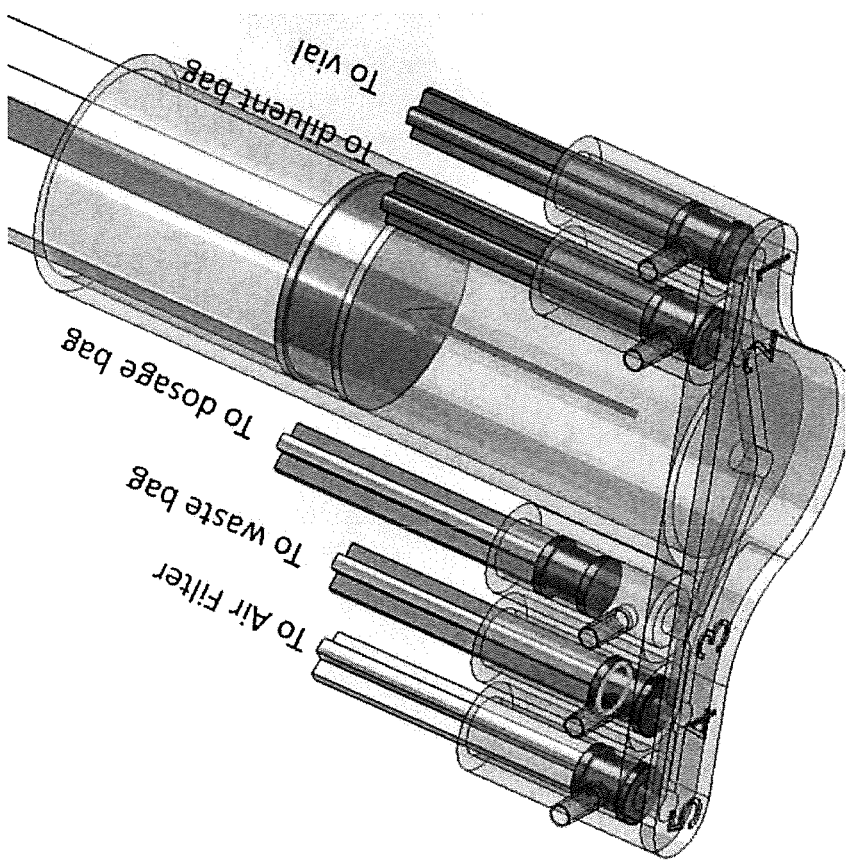
Figure 47:
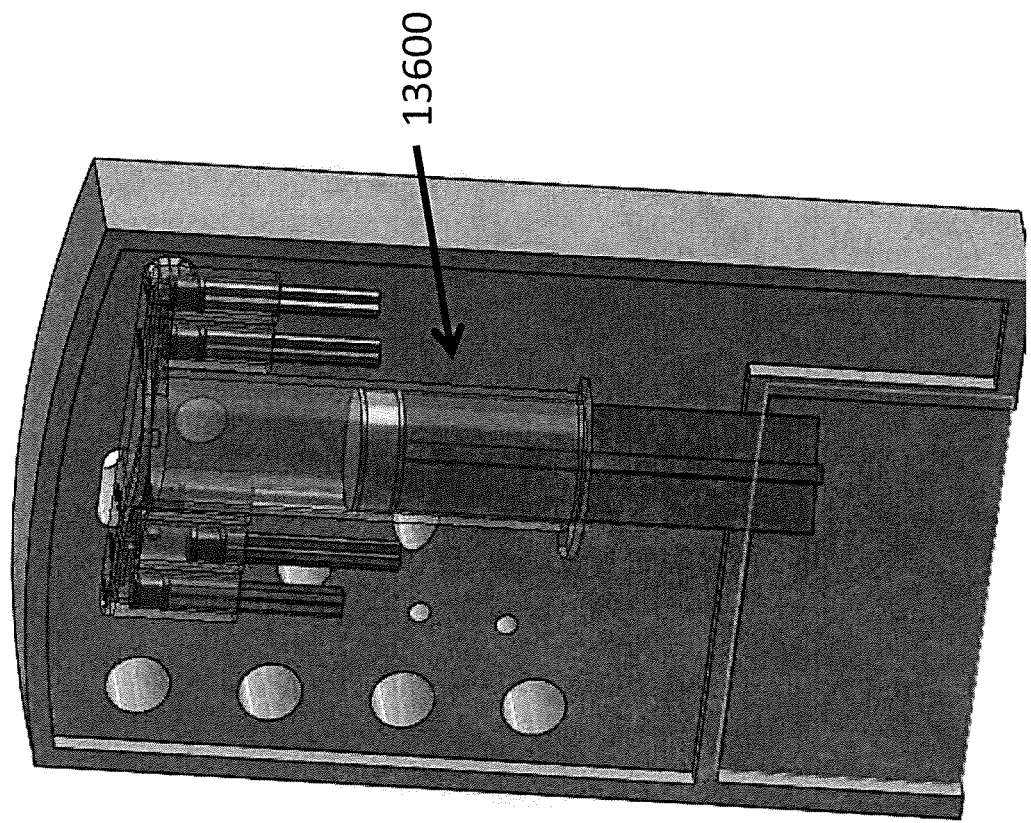
FIG. 47 illustrates a syringe pump/syringe valve apparatus attached to a compounder cartridge in accordance with aspects of the present disclosure.

The examples of FIGS. 45 and 46 show valve and piston operations for vacuum operations. In the example of FIG. 45, the plunger of syringe piston 13604 is being raised while a syringe valve 13602 coupled to receiving container 32 is open, to draw waste gas into the syringe piston from the receiving container. In the example of FIG. 46, the syringe valve 13602 coupled to the receiving container is closed, a syringe valve 13602 coupled to waste container 44 is open, and the plunger of syringe piston 13604 is being lowered to push the waste gases therein to the waste container. FIG. 47 shows apparatus 13600 coupled to cartridge 16 in a position in which the syringe plungers of the syringe piston and the syringe pump can be operated by the pump head assembly to control the flow of fluid and gasses through cartridge 16 (e.g., as described above in connection with FIGS. 39-46).

In the examples of FIGS. 36-47, one large syringe style pump provides the pumping action for compounder 10 and the valves to control the various processes are syringe type valves. Syringe type valves may be used for reliability and simplicity. As described above in connection with FIGS. 39-46, each of the different processes of compounder 10 can be assigned to a syringe valve and in many cases, only one syringe valve will be open at any one time. For example, during the reconstitution process, the syringe valve to the diluent bag will be opened as the syringe pump is pulling fluid into the syringe pump. Once the syringe pump chamber is full, the diluent bag syringe valve will close and the vial syringe valve will open. Once the vial syringe valve is open, the syringe pump will push the diluent fluid into the vial. Similar processes of syringe pump and valve operation can repeated for all the different processes of compounder 10.

In some implementations, instead of (or in addition to) a linearly oscillating piston pump with finger valves, a rotary piston pump, or a syringe piston pump/valve apparatus, as described above, cartridge 16 may be provided with a syringe pump and one or more rotary valves. FIG. 48 shows an example of a syringe pump/rotary valve apparatus that may be provided to control movement of fluid and/or gasses through cartridge 16. As shown in FIG. 48, syringe pump/rotary valve apparatus 14800 may include a syringe pump 14802 having an actuatable plunger 14804 and valve bank 14806 having output ports 14808. Each output port 14808 may be selectively fluidly coupled (by operation of valves internal to valve bank 14806) to a chamber within syringe pump 14802.

Figure 51:
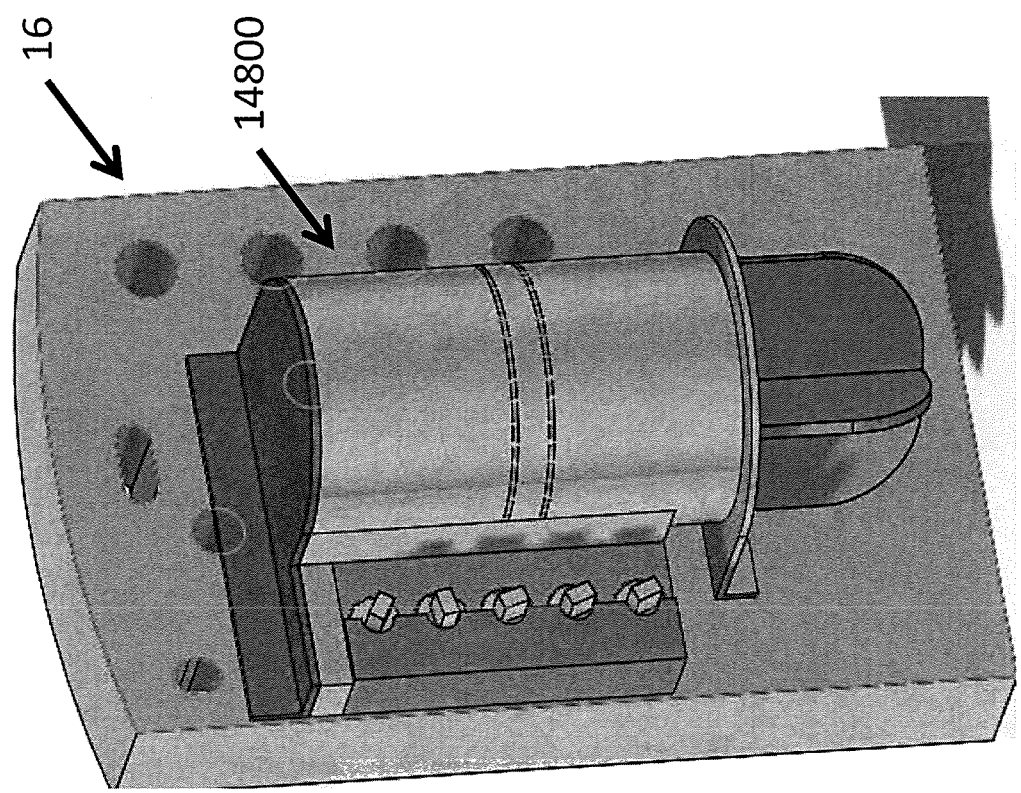
FIG. 51 illustrates a syringe pump/rotary valve apparatus attached to a compounder cartridge in accordance with aspects of the present disclosure.

FIG. 49 shows a front perspective view of syringe pump/rotary valve apparatus 14800 with a housing thereof shown in partial transparency so that a seal 14902 on plunger 14804, an internal fluid pathway 14904, and internal valve features of rotary valves 14900 in valve bank 14806 can be seen. As shown, fluid pathway 14904 may fluidly couple a chamber of syringe pump 14802 to rotary valves 14900, each of which can be rotated by the pump head assembly to couple pathway 14904 to ports 14808 during actuation of plunger 14804. FIG. 50 shows a front perspective view of syringe pump/rotary valve apparatus 14800 with an opaque housing, through which valve handles 15000 protrude for rotary operation of valves 14900 by the pump head assembly. FIG. 51 shows syringe pump/rotary valve apparatus 14800 coupled to cartridge 16 in a position in which the syringe plunger of the syringe piston rotary valves 14900 can be operated by the pump head assembly to control the flow of fluid and gasses through cartridge 16.

Figure 52:
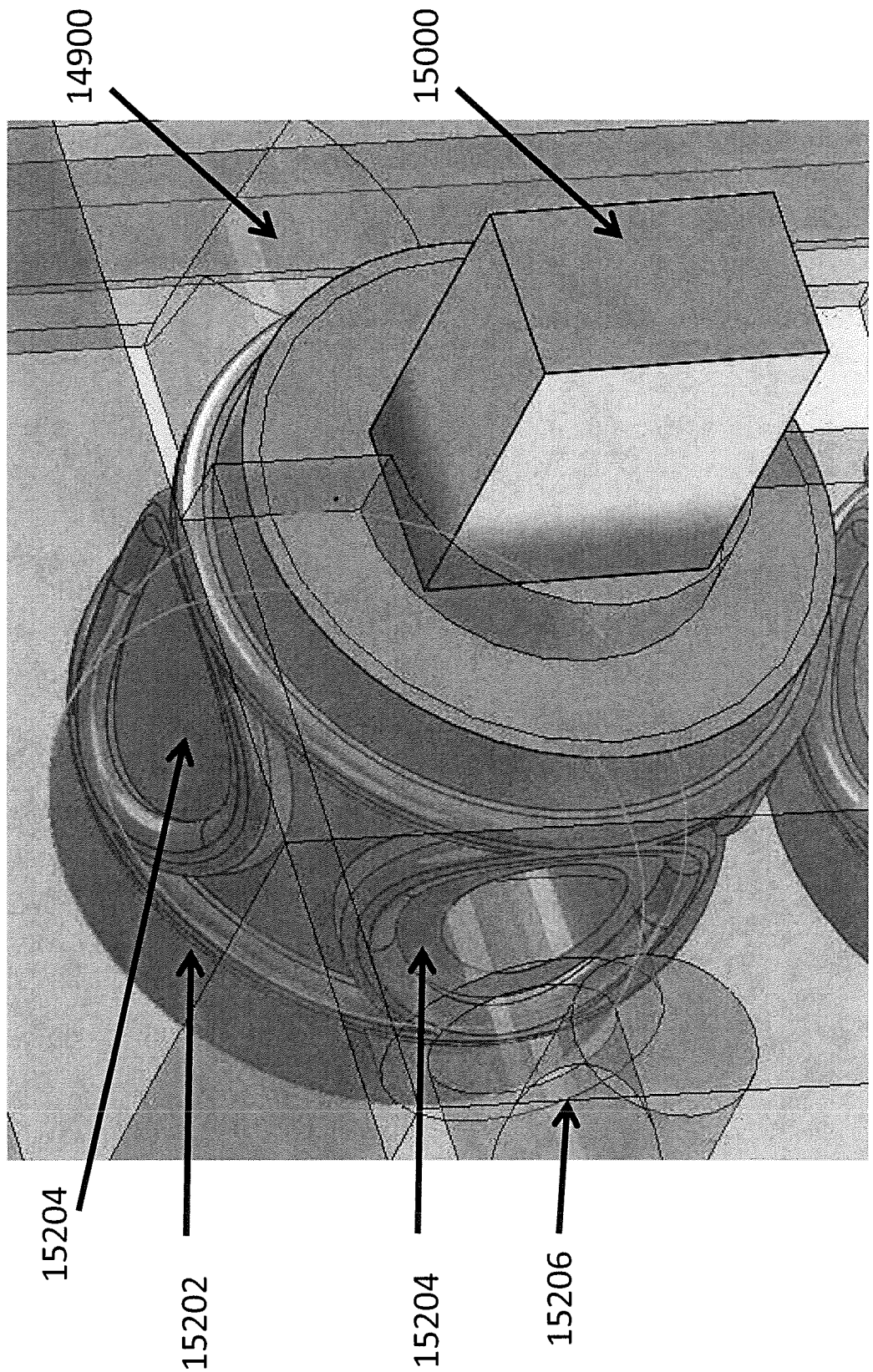
FIG. 52 illustrates a perspective view of a rotary valve of a syringe pump/rotary valve apparatus in accordance with aspects of the present disclosure.

FIG. 52 shows a perspective view of one of rotary valves 14900 in an embodiment in which the rotary valve is implemented as a stopcock rotary valve. As shown in FIG. 52, rotary valve 14900 includes openings 15204 disposed around a perimeter of a cylindrical internal valve member 15202 that is rotatable by valve handle 15000. Rotating valve handle 15000 rotates the positions of openings 15204 relative to fluid pathways 15206 of apparatus 14800 to open and close the valve.

In the examples of FIGS. 48-52, cartridge 16 has one large syringe-style pump and the valves to control the various processes are rotary stopcock style valves. Rotary valves may be used for their reliability and simplicity. Each of the different processes performed by compounder 10 may be performed using an assigned rotary valve and in many scenarios, only one rotary valve will be open at any one time. For example, during a reconstitution process, a rotary valve that controls a fluid pathway to the diluent bag will be opened as the syringe pump is pulling fluid into the syringe pump. Once the syringe pump chamber is full, the diluent bag valve will close and a vial rotary valve will open. Once the vial rotary valve is open, the syringe pump will push the diluent fluid into the vial. Similar processes of syringe pump and rotary valve operation can be repeated for all the different processes of compounder 10.

Figure 53:
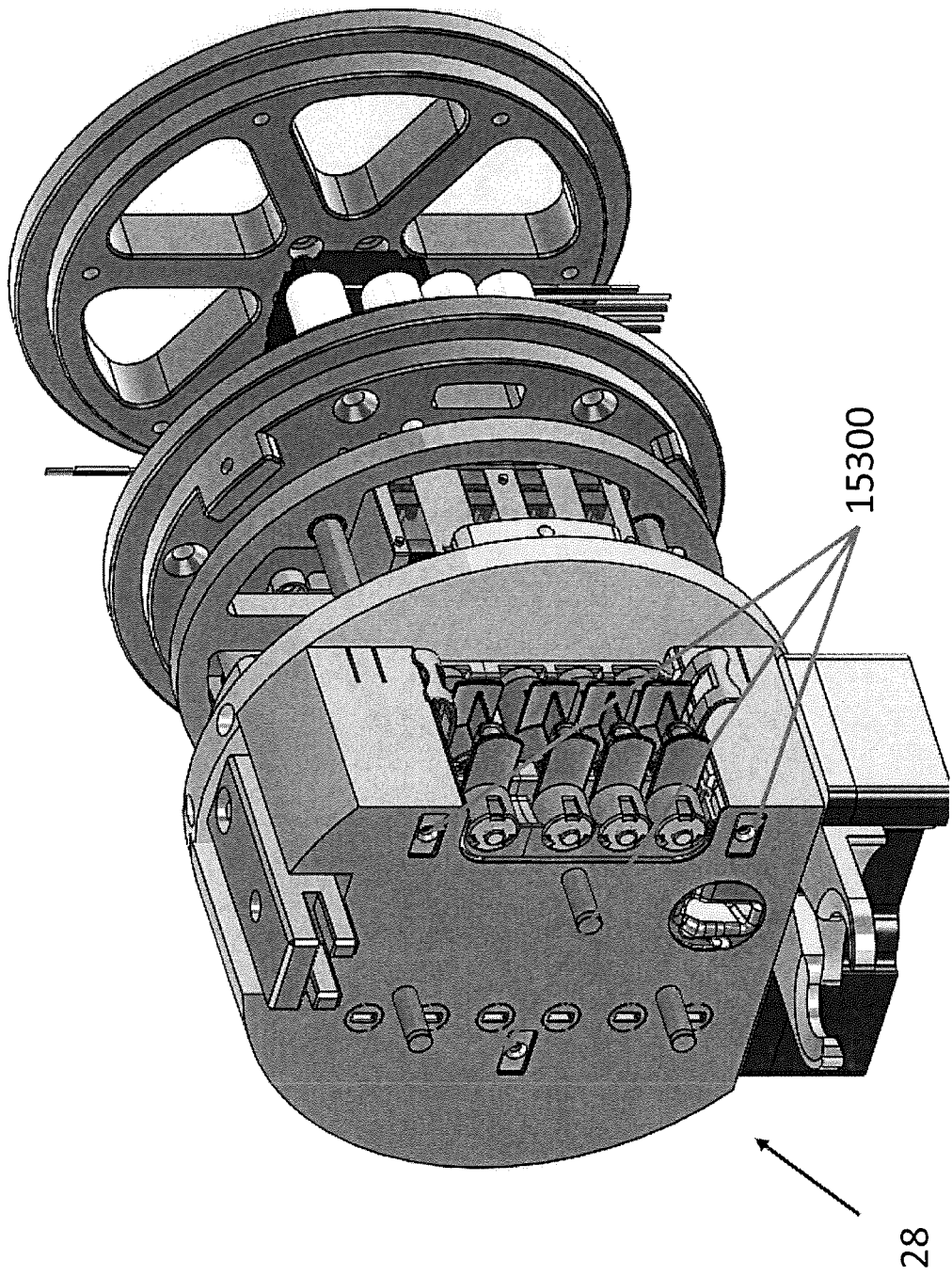
FIG. 53 illustrates a perspective view of a pump head assembly having magnets for attaching a compounder cartridge thereto in accordance with aspects of the present disclosure.

Various examples have been described herein in which cartridge 16 is coupled to the pump head assembly 28 by a bayonet or other positive latching mechanism operated by the pump head assembly. However, a positive latching mechanism such as a bayonet may be operated using a stepper or a direct-current motor to actuate the latching mechanism, which can add cost and complexity to the compounder. Accordingly, it should be appreciated that, in some embodiments, pump head assembly 28 may be provided with one or more magnets 15300 (see FIG. 53) for electromagnetically attaching cartridge 16 to pump head assembly 28.

Magnets 15300 may be active or passive magnets configured to temporarily attach the cartridge to the compounding arm. Magnets 15300 may be mounted to the face of the arm on the compounder in locations that correspond with respective metal plates or other ferromagnetic members attached to cartridge 16. As cartridge 16 is moved toward the face of the arm, the magnets are activated to attract and attach the cartridge to the face of the arm. When the cartridge is to be returned to the carousel, the magnets may be deactivated (e.g., once the cartridge is docked into the carousel). The magnetic coupling can be used independently or in conjunction with a positive mechanical latching mechanism.

The various features described herein in connection with, for example, FIGS. 32-53 may be used, alone or in combination with each other and/or the features described in connection with FIGS. 1-31 to help provide simple high flow fluid paths and/or simple rotary valving, to facilitate reducing or eliminating the need for priming and/or air flush of tubing such as "pigtail" tubing, to help provide flow paths with easy to check for leakage during production, to provide a slow motion syringe pump that helps reduce or eliminate frothing and/or damaging of the drug, to facilitate use of a common cartridge for micro and regular dosing, to help reduce the interactions between the pump head assembly (pump arm) and the cartridge, to help facilitate use of a single-dose waste container, to help facilitate use of a single vial needle, to provide individual, independent valve control for flexibility in controlling processes, to facilitate use of an air in-line sensor in tubing such as "pigtail" tubing to a receiving container, and/or to reduce tolerances with respect to some of the features described in connection with FIGS. 1-31 and/or in existing systems.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

The subject technology is illustrated, for example, according to various aspects described above. Various examples of these aspects are described as numbered concepts or clauses (1, 2, 3, etc.) for convenience. These concepts or clauses are provided as examples and do not limit the subject technology. It is noted that any of the dependent concepts may be combined in any combination with each other or one or more other independent concepts, to form an independent concept. The following is a non-limiting summary of some concepts presented herein:

Concept 1. A compounder system, comprising:
  a cartridge having:
    a plurality of controllable fluid pathways fluidly coupled to at least one diluent port, a waste port, and a receiving container port; and
    a syringe pump/syringe valve apparatus having a plurality of syringes operable to control movement of one or more fluids through the plurality of controllable fluid pathways.
  Concept 2. The compounder system of Concept 1 or any other Concept, wherein the syringe pump/syringe valve apparatus comprises a housing having a syringe pump cylinder with a syringe pump plunger, a plurality of syringe valve cylinders, and a fluid flow pathway between the syringe pump cylinder and the plurality of syringe valve cylinders.
Concept 3. The compounder system of Concept 2 or any other Concept, wherein each of the syringe valve cylinders comprises a port and a syringe plunger actuatable to open and close the port.
Concept 4. The compounder system of Concept 3 or any other Concept, wherein the plurality of syringe valve cylinders comprises a diluent cylinder having a diluent port configured to be coupled to a diluent container and a vial cylinder having a vial port configured to be coupled to a vial containing a drug.
Concept 5. The compounder system of Concept 4 or any other Concept, further comprising a pump head that includes one or more actuable components configured to:
  open the diluent port by moving the syringe plunger in the diluent cylinder; and
  move the syringe pump plunger in a first direction within the syringe pump cylinder, to pull diluent into the syringe pump cylinder via the diluent port.
Concept 6. The compounder system of Concept 5 or any other Concept, wherein the actuable components are further configured to:
  close the diluent port by moving the syringe plunger in the diluent cylinder;
  open the vial port by moving the syringe plunger in the vial cylinder; and
  move the syringe pump plunger in a second direction, to push the diluent from the syringe pump cylinder through the vial port.

Concept 7. The compounder system of Concept 6 or any other Concept wherein the actuable components are further configured to:
- move the syringe pump plunger in the first direction within the syringe pump cylinder, to pull a medication into the syringe pump cylinder via the vial port;
- close the vial port by moving the syringe plunger in the vial cylinder;
- open an output port by moving a syringe plunger in an output cylinder of the plurality of syringe valve cylinders; and
- move the syringe pump plunger in the second direction, to push the medication from the syringe pump cylinder through the output port.

Concept 8. The compounder system of Concept 3 or any other Concept, wherein the fluid flow pathway is coupled to each of the syringe valve cylinders by a corresponding coupling cylinder 13609 in the housing, wherein each of the coupling cylinders 13609 extends from a corresponding one of the plurality of syringe valve cylinders in a first direction, and wherein the port of each of the syringe valve cylinders extends from that syringe valve cylinder in a second direction that is perpendicular to the first direction.

Concept 9. A compounder system, comprising:
- a cartridge having:
  - a plurality of controllable fluid pathways fluidly coupled to at least one diluent port, a waste port, and a receiving container port; and
- a syringe pump/rotary valve apparatus having a syringe and a plurality of rotary valves operable to control movement of one or more fluids through the plurality of controllable fluid pathways.

Concept 10. The compounder system of Concept 9 or any other Concept, wherein at least one of the rotary valves is a stopcock rotary valve.

Concept 11. The compounder system of Concept 9 or any other Concept, further comprising a pump head assembly, wherein each of the rotary valves comprises an external valve handle, and wherein the pump head assembly is configured to actuate the syringe and to rotate one or more of the external valve handles to control motion of the one or more fluids through the controllable fluid pathways.

Concept 12. The compounder system of Concept 11 or any other Concept, wherein each of the rotary valves is rotatable by the external valve handle of that rotary valve to selectively couple a port corresponding to that rotary valve with a chamber of the syringe.

Concept 13. The compounder system of Concept 12 or any other Concept, wherein the port corresponding to each rotary valve extends into the cartridge.

Concept 14. The compounder system of Concept 11 or any other Concept, wherein each rotary valve comprises first and second openings disposed around a perimeter of a cylindrical internal valve member that is rotatable by the external valve handle of that rotary valve.

Concept 15. The compounder system of Concept 14 or any other Concept, wherein:
- in a first rotational position for each cylindrical internal valve member, the first and second openings of that cylindrical internal valve member align with corresponding fluid pathways in the syringe pump/rotary valve apparatus to allow fluid flow through that cylindrical internal valve member; and
- in a second rotational position for each cylindrical internal valve member, at least one of the first and second openings of that cylindrical internal valve member is angularly separated from both of the corresponding fluid pathways in the syringe pump/rotary valve apparatus to prevent fluid flow through that cylindrical internal valve member.

Concept 16. A compounder system, comprising:
- a cartridge having:
  - a plurality of controllable fluid pathways;
  - a syringe pump; and
  - a plurality of valves operable to selectively couple the syringe pump to one or more of the plurality of controllable fluid pathways.

Concept 17. The compounder system of claim 16 or any other Concept, wherein the plurality of valves comprise at least one syringe valve.

Concept 18. The compounder system of Concept 17 or any other Concept, further comprising a common housing for the syringe pump and the at least one syringe valve, the common housing comprising a fluid pathway between syringe pump and the at least one syringe valve.

Concept 19. The compounder system of Concept 16 or any other Concept, wherein the plurality of valves comprise at least one rotary valve.

Concept 20. The compounder system of Concept 19 or any other Concept, wherein the at least one rotary valve comprises a stopcock rotary valve.

One or more aspects or features of the subject matter described herein may be realized in digital electronic circuitry, integrated circuitry, specially designed ASICs (application specific integrated circuits), computer hardware, firmware, software, and/or combinations thereof. For example, infusion pump systems disclosed herein may include an electronic system with one or more processors embedded therein or coupled thereto. Such an electronic system may include various types of computer readable media and interfaces for various other types of computer readable media. Electronic system may include a bus, processing unit(s), a system memory, a read-only memory (ROM), a permanent storage device, an input device interface, an output device interface, and a network interface, for example.

Bus may collectively represent all system, peripheral, and chipset buses that communicatively connect the numerous internal devices of electronic system of an infusion pump system. For instance, bus may communicatively connect processing unit(s) with ROM, system memory, and permanent storage device. From these various memory units, processing unit(s) may retrieve instructions to execute and data to process in order to execute various processes. The processing unit(s) can be a single processor or a multi-core processor in different implementations.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

As used herein, the phrase "at least one of" preceding a series of items, with the term "or" to separate any of the items, modifies the list as a whole, rather than each item of the list. The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, or C" may refer to: only A, only B, or only C; or any combination of A, B, and C.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that the specific order or hierarchy of steps, or operations in the processes or methods disclosed are illustrations of exemplary approaches. Based upon implementation preferences or scenarios, it is understood that the specific order or hierarchy of steps, operations or processes may be rearranged. Some of the steps, operations or processes may be performed simultaneously. In some implementation preferences or scenarios, certain operations may or may not be performed. Some or all of the steps, operations, or processes may be performed automatically, without the intervention of a user. The accompanying method Concepts present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the Concepts. Moreover, nothing disclosed herein is intended to be dedicated to the public regardless of whether such disclosure is explicitly recited in the Concepts. No Concepts element is to be construed under the provisions of 35 U.S.C. § 112 (f) unless the element is expressly recited using the phrase "means for" or, in the case of a method Concepts, the element is recited using the phrase "step for." Furthermore, to the extent that the term "include," "have," or the like is used, such term is intended to be inclusive in a manner similar to the term "comprise" as "comprise" is interpreted when employed as a transitional word in a Concepts.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the Concepts. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each Concepts. Rather, as the following Concepts reflect, inventive subject matter lies in less than all features of a single disclosed configuration or operation. The following Concepts are hereby incorporated into the Detailed Description, with each Concept standing on its own as a separately disclosed subject matter.

The Concepts are not intended to be limited to the aspects described herein, but are to be accorded the full scope consistent with the language Concepts and to encompass all legal equivalents. Notwithstanding, none of the Concepts are intended to embrace subject matter that fails to satisfy the requirement of 35 U.S.C. § 101, 102, or 103, nor should they be interpreted in such a way.

What is claimed is:

1. A compounder system, comprising:
   a carousel assembly;
   a cartridge coupled to the carousel assembly, the cartridge having:
      a diluent port;
      a waste port;
      a receiving container port; and
      a plurality of controllable fluid pathways fluidly coupled to the diluent port, the waste port, and the receiving container port, the plurality of controllable fluid pathways configured to be coupled to a vial, one or more diluents, a receiving container and a waste container; and
   a syringe pump/rotary valve apparatus coupled to the cartridge and having a syringe and a plurality of rotary valves operable to control movement of one or more fluids through the plurality of controllable fluid pathways,
   wherein each of the diluent port, the waste port and the receiving container port are coupled to a separate rotary valve of the plurality of rotary valves to individually control fluid flow through the coupled port.

2. The compounder system of claim 1, wherein at least one of the rotary valves is a stopcock rotary valve.

3. The compounder system of claim 1, further comprising a pump head assembly, wherein each of the rotary valves comprises an external valve handle, and wherein the pump head assembly is configured to actuate the syringe and to rotate one or more of the external valve handles to control motion of the one or more fluids through the controllable fluid pathways.

4. The compounder system of claim 3, wherein each of the rotary valves is rotatable by the external valve handle of that rotary valve to selectively couple a port corresponding to that rotary valve with a chamber of the syringe.

5. The compounder system of claim 4, wherein the port corresponding to each rotary valve extends into the cartridge.

6. The compounder system of claim 3, wherein each rotary valve comprises first and second openings disposed around a perimeter of a cylindrical internal valve member that is rotatable by the external valve handle of that rotary valve.

7. The compounder system of claim 6, wherein:
- in a first rotational position for each cylindrical internal valve member, the first and second openings of that cylindrical internal valve member align with corresponding fluid pathways in the syringe pump/rotary valve apparatus to allow fluid flow through that cylindrical internal valve member; and
- in a second rotational position for each cylindrical internal valve member, at least one of the first and second openings of that cylindrical internal valve member is angularly separated from both of the corresponding fluid pathways in the syringe pump/rotary valve apparatus to prevent fluid flow through that cylindrical internal valve member.

* * * * *